(12) United States Patent
Fukada et al.

(10) Patent No.: US 7,074,614 B2
(45) Date of Patent: Jul. 11, 2006

(54) CLOCK GENE BMAL2

(75) Inventors: Yoshitaka Fukada, Tokyo (JP); Toshiyuki Okano, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 268 days.

(21) Appl. No.: 10/467,721

(22) PCT Filed: Aug. 23, 2001

(86) PCT No.: PCT/JP01/07197

§ 371 (c)(1),
(2), (4) Date: Aug. 11, 2003

(87) PCT Pub. No.: WO02/064785

PCT Pub. Date: Aug. 22, 2002

(65) Prior Publication Data

US 2004/0058366 A1    Mar. 25, 2004

(30) Foreign Application Priority Data

Feb. 13, 2001    (JP) ............................... 2001-35743

(51) Int. Cl.
*C12N 5/10*    (2006.01)
*C07H 21/04*    (2006.01)

(52) U.S. Cl. ..................... 435/349; 536/23.5

(58) Field of Classification Search ............ None
See application file for complete search history.

(56) References Cited

FOREIGN PATENT DOCUMENTS

WO    WO 99/28464 A2    6/1999
WO    WO 00/09657 A2    2/2000

OTHER PUBLICATIONS

Abdrakhmanov et al., "A Large Database of Chicken Bursal ESTs as a Resource for the Analysis of Vertebrate Gene Function," Genome Research, vol. 10, No. 12, pp. 2062-2069 (2000).*
Gekakis, N. et al. "Role of the CLOCK protein in the mammalian circadian mechanism," Science, 1998, vol. 280, pp. 1564-1569.
Hogenesch, J.B. et al. "Characterization of a subset of the basic-helix-loop-helix-PAS superfamily that interacts with components of the dioxin signaling pathway." J. Biol. Chem., 1997, vol. 272, p. 8581-8593.

* cited by examiner

*Primary Examiner*—Robert A. Wax
(74) *Attorney, Agent, or Firm*—Morgan & Finnegan, L.L.P.; Kenneth H. Sannenfeld; Michael A. Willis

(57) ABSTRACT

The present invention provides novel clock proteins BMAL2 (Brain-Muscle-Arnt-Like protein2), which is crucial for the clock oscillation mechanism including photic-input pathway and output pathway, novel clock genes encoding the proteins, a screening method using the proteins to screen a promoter or a suppressor of the promoter transactivation, and the like.

Genes for cCLOCK, cPER2, cBMAL1 were isolated from the chicken pineal gland which is a material suitable for studying circadian clock, then cDNA encoding the novel clock protein cBMAL2 having homology with cBMAL1 was isolated and sequenced. Further, BMAL2 cDNAs in human, mouse and rat were isolated respectively from the human embryonic kidney cell line, the mouse mid brain and the rat early fibroblast, and sequences of these cDNAs were determined. BMAL2 forms a heterodimer with CLOCK or BMAL1, etc. and it also forms a homodimer.

7 Claims, 12 Drawing Sheets

FIG. 1

```
MDCIEVRGFY SSTEEQNPEQ QADISENISS LFSLKEQQKM SEYSGLASNH SQMIAEDSEI  60
QPKPEHSPEV LQEDIEMSSG SSGNDFSGNE TNENYSSGHD SHGHESDENG KDSAMLMESS 120
DCHKSSSSNA FSLMIANSEH NQSSSGCSSE QSTKAKTQKE LLKTLQELKA HLPAEKRIKG 180
KSSVLTTLKY ALKSIKQVKA NEEYYQLLMI NESQPSGLNV SSYTVEEVET ITSEYIMKNA 240
                PAS-A
DMFAVAVSLI TGKIVYISDQ AAAILRCKRS YFKNAKFVEL LAPQDVSVFY TSTTPYRLPS 300
WNICSRAESS TQDCMEEKSF FCRISAGKER ENEICYHPFR MTPYLIKVQD PEVAEDQLCC 360
                                                PAS-B
VLLAEKVHSG YEAPRIPPDK RIFTTTHTPT CLFQDVDERA VPLLGYLPQD LIGTPVLVHL 420
                                                    CLD
HPNDRPLMLA IHKKILQYGG QPFDYSPIRF CTRNGDYITM DTSWSSFINP WSRKVSFIIG 480
RHKVRTGPLN EDVFAAPNYT EDRILHPSVQ EITEQIYRLL LQPVHNSGSS GYGSLGSNGS 540
HEHLMSVASS SDSTGNNNDD TQKDKTISQD ARKVKTKGQH IFTENKGKLE YKREPSAEKQ 600
NGPGGQVKDV IGKDTTATAA PKNVATEELA WKEQPVYSYQ QISCLDSVIR YLESCNVPGT 660
AKRKCEPSSS VNSSVHEQKA SVNAIQPLGD STVLKSSGKS SGPPVVGAHL TSLALPGKPE 720
SVVSLTSQCS YSSTIVHVGD KKPQPELEMI EDGPSGAEVL DTQLPAPPPS STHVNQEKES 780
FKKLGLTKEV LAVHTQKEEQ SFLNKFKEIK RFNIFQSHCN YYLQDKPKGR PGERGGRGQR 840
NGTSGMDQPW KKSGKNRKSK RIKPQESSDS TTSGTKFPHR FPLQGLNTTA WSPSDTSQAS 900
YSAMSFPTVM PAYPLPVFPA AAGTVPPAPE TSVSGFNQLP DSGNTCSMQP SQFSAPLMTP 960
VVALVLPNYV YPEMNNSLPQ TLYHSQANFP THPAFSSQTV FPAQPPFTTP SPFPQQAFFP 1020
MQPFHYNPPA EIERVPVTET RNEPSRSCTP QSVGPQDQAS PPLFQSRCSS PLNLLQLEEN 1080
TKTVESGAPA GLHGALNEEG TIGKIMTTDA GSGKGSLPAE SPMDAQNSDA LSMSSVLLDI 1140
LLQEDACSGT GSASSGSGVS AAAESLGSGS NGCDMSGSRT GSSETSHTSK YFGSIDSSEN 1200
HHKTKMKAEI EESEHFIKYV LQDPIWLLMA NTDDTVMMTY QLPSRDLETV LKEDKLKLKQ 1260
MQKLQPKFTE DQKRELIEVH PWIQQGGLPK TVANSECIFC EDNIQSNFYT SYDEEIHEMD 1320
LNEMIEDSGE NNLVPLSQVN EEQT                                      1344
```

FIG. 2

| Homology (%) | N-terminal region | PAS | | CLD | C-terminal region | Whole region |
| --- | --- | --- | --- | --- | --- | --- |
| | | A | B | | | |
| mPER1 | 31 | 67 | 52 | 84 | 86 | 32 | 32 |
| mPER2 | 46 | 69 | 71 | 88 | 87 | 46 | 46 |
| mPER3 | 14 | 54 | 46 | 78 | 67 | 22 | 22 | cPER2: 1 — PAS (A, B) — CLD — 1344

[sequence alignment of mBMAL1b', cBMAL1b', cBMAL2, hBMAL2a showing bHLH, PAS-A, and PAS-B domains]

CLOCK GENE BMAL2

This application is a national stage application, filed under 35 USC 371, of PCT/JP01/07197, filed Aug. 23, 2001, which claims priority to Japanese application 2001-35743, filed Feb. 13, 2001.

TECHNICAL FIELD

The present invention relates to novel proteins BMAL (Brain-Muscle-Arnt-Like protein) 2 which are involved in circadian rhythm, their genes, and their use.

BACKGROUND ART

Life activity is connaturally accompanied with various cyclic changes ranging from the behavior at the individual level to the biochemical phenomena at the cellular level. These rhythmic life activities occurring at certain cycles are called biorhythm and a periodic length of these phenomena which are repeated in cycles is often close to a periodic fluctuation of the environment such as a year, a month or a day. Sleep-wake rhythm and hormonal-secretion rhythm for such as melatonin and the adrenal cortex hormone are among those representing circadian rhythms repeated by an approximately 24-hour cycle, a daily unit. The circadian rhythms as mentioned have been observed in almost all the biological species and tissues and are regulated by the biological clock (Annu. Rev. Physiol. 55, 16–54, 1993). The suprachiasmatic nucleus (SCN) in the vertebrate central nervous system, pineal gland, specific neuronal tissues such as retina, etc. are known as tissues conforming circadian rhythm (Science 203, 1245–1247, 1979, Science 203, 656–658, 1979, Proc. Natl. Acad. Sci. USA 76, 999–1003, 1979, Brain Res. 245, 198–200, 1982, Neuron 10, 573–577, 1993, Science 272, 419–421, 1996).

As in the case of the mammalian suprachiasmatic nucleus (SCN), non-mammalian vertebrate pineal glands produce melatonin in response to circadian rhythm and light stimuli and play a central role in the physiological circadian regulation (Science 203, 1245–1247, 1979, Science 203,656–658, 1979, Proc. Natl. Acad. Sci. USA 76, 999–1003, 1979, Proc. Natl. Acad. Sci. USA 77, 2319–2322, 1980, Proc. Natl. Acad. Sci. USA 80, 6119–6121, 1983, J. Neurosci. 9, 1943–1950, 1989). The oscillation mechanism of the above-mentioned circadian rhythm is said to be characterized by the system wherein oscillation occurs at the gene level, is then amplified at the cellular level and finally reaches the individual level (Cell 96, 271–290, 1999). Oscillation at the gene level is brought by a group of genes called clock genes. Recent studies on the rodent clock genes have revealed that the circadian oscillator genes in mammals are positive and negative elements which form the transcription/translation-based negative feedback loop (Cell 96, 271–290, 1999, Annu. Rev. Neurosci. 23, 713–742, 2000). In mice, the negative elements include three period gene homologs; Per1 (Cell 90, 1003–1011,1997, Nature 389,512–516,1997), Per2 (Cell 91, 1055–1064, 1997, Neuron 19, 1261–1269, 1997, Genes Cells 3, 167–176, 1998) and Per3 (EMBO J. 17, 4753–4759, 1998, Neuron, 20, 1103–1110, 1998) and two cryptochrome homologs; Cry1 and Cry2 (Cell 98, 193–205, 1999, Nature 398, 627–630, 1999).

As for positive elements, BMAL1, CLOCK and the like which are basic helix-loop-helix (bHLH)-PAS (Per-Arnt-Sim) transcription elements are known. A CLOCK-BMAL1 complex is known to activate transcription through an E-box sequence (E-box: CACGTG) which is found not only in the negative element Per1 (Science 280, 1564–1569, 1998) but also in clock-controleed genes such as vasopressin (Cell 96, 57–68, 1999) and in the albumin D-site binding protein gene (Genes Dev.14, 679–689, 2000). When a protein level of a negative element mentioned above is increased, its own transactivation for a promoter induced by a positive element is suppressed, the mRNA and protein levels of the negative element are down-regulated, and the molecular cycle is recommenced concomitant with the transactivation of the negative element gene. Therefore, the protein and mRNA levels of a negative element display a marked circadian oscillation. In addition to fluctuations in these clock genes, Per1 and Per2 expressions are induced by light (Cell 91, 1055–1064, 1997, Neuron 19, 1261–1269, 1997, Cell 91, 1043–1053, 1997) and at least photo synchronization of an oscillatorisinducedbyPer1 (J. Neurosci. 19,1115–1121,1999). Further, it has been revealed that mRNA levels of a positive element Bmal1 also exhibit circadian oscillation in antiphase to those of negative elements (Biochem. Biophys. Res. Commun. 250, 83–87, 1998, Biochem. Biophys. Res. Commun. 253, 199–203, 1998). Since its transcriptional rhythm is close to that of the *Drosophila* dClock (Science 286, 766–768, 1999), Bmal1 is thought to be involved in feedback loop of the negative elements (Science 286, 2460–2461, 1999, Science 288, 1013–1019, 2000).

On the other hand, the chicken (chick) pineal gland has been known that it retains the circadian oscillator as well as photic-input pathway and melatonin-output pathway in the pineal cell and that these properties can readily be retained under culturedconditions (Science 203, 1245–1247, 1979, Science 203, 656–658, 1979, Proc. Natl. Acad. Sci. USA 77, 2319–2322, 1980, Brain Res.438, 199–215, 1988, Recent Prog. Horm. Res. 45, 279–352, 1989, Nature 372, 94–97, 1994, Proc. Natl. Acad. Sci. USA 94, 304–309, 1997, Brain Res. 774, 242–245, 1997). On the basis of these observations, the chick pineal cell is thought to be a prominent model for the study of the vertebrate circadian clock systems at the cellular level (Recent Prog. Horm. Res. 45, 279–352, 1989).

It is known that the biological clock is an auto-oscillatory system which oscillates autonomically without any exogenous stimulation and which, at the same time, has a property of being reset by the exogenous light-stimulation. It is also known that the vertebrate biological clock (circadian clock) which autonomically oscillates in a period close to a day is driven by the auto-feedback-loop consisting of a negative element and a positive element. Many things, however, still remain unknown with regard to the molecular clock system and the like including photic-input and output pathways. The object of the present invention is to provide novel proteins BMAL2 (Brain-Muscle-Arnt-Like protein 2) crucial in the clock oscillation mechanism including photic-input and output pathways, genes encoding the proteins, a method for screening a promoter or a suppressor of the promoter transactivation using the proteins, and the like.

DISCLOSURE OF THE INVENTION

The present inventors have made a keen study to solve the object mentioned above, and isolated cCLOCK, cPER2 and cBMAL1 genes from the chicken pineal gland which is a material suitable for the study of circadian clock, and further isolated cDNA encoding the novel clock protein cBMAL2 which was homologous with cBMAL1 and sequenced it. The inventors have also isolated the human, mouse and rat BMAL2 cDNAs respectively from the human embryonic kidney cell line, the mouse mid brain and the rat early fibroblast and sequenced them. In the pull-down assay, these novel clock proteins BMAL2 were found to form heterodimers with CLOCK, BMAL1 or the like, and to form homodimers among themselves (BMAL2). Besides, in the luciferase assay, BMAL2 were observed not only to form heterodimers with CLOCK and activate transcription via E-box but also to form homodimers and bind to E-box to cooperatively suppress transcription. Here the present invention is accomplished.

The present invention relates to: DNA encoding a protein (a) or (b) below,
(a) a protein comprising an amino acid sequence shown by Seq. ID No. 2, 4, 6 or 8,
(b) a protein which comprises an amino acid sequence wherein one or a few amino acids are deleted, substituted or added in the amino acid sequence shown by Seq. ID No. 2, 4, 6 or 8 and which has the BMAL2 activity (claim 1); DNA containing a base sequence shown by Seq. ID No. 1, 3, 5 or 7 or its complementary sequence and part or whole of these sequences (claim 2); DNA which hybridizes with DNA of claim 2 under a stringent condition and which encodes a protein having the BMAL2 activity (claim 3); DNA encoding a protein (a) or (b) below,
(a) a protein comprising an amino acid sequence shown by Seq. ID No. 10,
(b) a protein which comprises an amino acid sequence wherein one or a few amino acids are deleted, substituted or added in the amino acid sequence shown by Seq. ID No. 10 and which has the BMAL2 activity (claim 4); DNA containing a base sequence shown by Seq. ID No. 9 or its complementary sequence and part or whole of these sequences (claim 5); DNA which hybridizes with DNA of claim 5 under a stringent condition and which encodes a protein having the BMAL2 activity (claim 6); DNA encoding a protein (a) or (b) below,
(a) a protein comprising an amino acid sequence shown by Seq. ID No. 12 or 14,
(b) a protein which comprises an amino acid sequence wherein one or a few amino acids are deleted, substituted or added in the amino acid sequence shown by Seq. ID No. 12 or 14 and which has the BMAL2 activity (claim 7); DNA containing a base sequence shown by Seq. ID No. 11 or 13 or its complementary sequence and part or whole of these sequences (claim 8); DNA which hybridizes with DNA of claim 8 under a stringent condition and which encodes a protein having the BMAL2 activity (claim 9); DNA encoding a protein (a) or (b) below,
(a) a protein comprising an amino acid sequence shown by Seq. ID No. 16, 18 or 20,
(b) a protein which comprises an amino acid sequence wherein one or a few amino acids are deleted, substituted or added in the amino acid sequence shown by Seq. ID No. 16, 18 or 20 and which has the BMAL2 activity (claim 10); DNA containing a base sequence shown by Seq. ID No. 15, 17 or 19 or its complementary sequence and part or whole of these sequences (claim 11); and DNA which hybridizes with DNA of claim 11 under a stringent condition and which encodes a protein having the BMAL2 activity (claim 12).

The present invention further relates to: a protein comprising an amino acid sequence shown by Seq. ID No. 2, 4, 6 or 8 (claim 13); a protein which comprises an amino acid sequence wherein one or a few amino acids are deleted, substituted or added in the amino acid sequence shown by Seq. ID No. 2, 4, 6 or 8 and which has the BMAL2 activity (claim 14); a protein comprising an amino acid sequence shown by Seq. ID No. 10 (claim 15); a protein which comprises an amino acid sequence wherein one or a few amino acids are deleted, substituted or added in the amino acid sequence shown by Seq. ID No. 10 and which has the BMAL2 activity (claim 16); a protein comprising an amino acid sequence shown by Seq. ID No. 12 or 14 (claim 17); a protein which comprises an amino acid sequence wherein one or a few amino acids are deleted, substituted or added in the amino acid sequence shown by Seq. ID No. 12 or 14 and which has the BMAL2 activity (claim 18); a protein comprising an amino acid sequence shown by Seq. ID No. 16, 18 or 20 (claim 19); a protein which comprises an amino acid sequence wherein one or a few amino acids are deleted, substituted or added in the amino acid sequence shown by Seq. ID No. 16, 18 or 20 and which has the BMAL2 activity (claim 20); and a peptide which comprises part of the protein of any of claims 13–20 and which has the BMAL2 activity (claim 21).

The present invention still further relates to: a fusion protein or a fusion peptide wherein the protein of any of claims 13–20 or the peptide of claim 21 is bound with a marker protein and/or a peptide tag (claim 22); an antibody which specifically binds to the protein of any of claims 13–20 or to the peptide of claim 21 (claim 23); the antibody according to claim 23, wherein the antibody is a monoclonal antibody (claim 24); a recombinant protein or peptide to which the antibody of claim 23 or 24 specifically binds and which has the BMAL2 activity (claim 25); a host cell comprising an expression system capable of expressing the protein of any of claims 13–20 or the peptide of claim 21 (claim 26); the host cell according to claim 26, wherein the host cell is further capable of expressing CLOCK and/or BMAL1 (claim 27); the host cell according to claim 26 or 27, wherein the expression system at least comprises a promoter having an E-box sequence (CACGTG) (claim 28); the host cell according to claim 28, wherein the promoter having an E-box sequence (CACGTG) is a promoter of Per gene, Tim gene, Cry gene, vasopressin gene or the albumin D-site binding protein gene (claim 29); a non-human animal which, on its chromosome, is deficient in the gene function to encode the protein of any of claims 13–20 or the peptide of claim 21 or which over-expresses the protein of any of claims 13–20 or the peptide of claim 21 (claim 30); and the non-human animal according to claim 30, wherein the non-human animal is a mouse or a rat (claim 31).

The present invention also relates to: a method for screening a promoter or a suppressor for the expression of the protein of any of claims 13–20/the peptide of claim 21 or a promoter or a suppressor of the Bmal2 activity, wherein a cell expressing the protein or peptide and a test substance are used (claim 32); the method for screening a promoter or a suppressor for the expression of the protein/peptide or a promoter or a suppressor of the Bmal2 activity according to claim 32, wherein the cell expressing the protein of any of claims 13–20 or the peptide of claim 21 is the host cell of any of claims 26–29 (claim 33); a method for screening a promoter or a suppressor for the expression of the protein of any of claims 13–20/the peptide of claim 21 or a promoter or a suppressor of the Bmal2 activity, wherein the non-human animal of claim 30 or 31 and a test substance are used (claim 34); an expression promoter of the protein of any of claims 13–20 or the peptide of claim 21, wherein the expression promoter is obtained by the screening method according to any of claims 32–34 (claim 35); an expression suppressor for the protein of any of claims 13–20 or the peptide of claim 21, wherein the expression promoter is obtained by the screening method according to any of claims 32–34 (claim 36); a promoter of the Bmal2 activity obtained by the screening method according to any of claims 32–34 (claim 37); and a suppressor for the Bmal2 activity obtained by the screening method according to any of claims 32–34 (claim 38).

The present invention further relates to: a method for screening a promoter or a suppressor for the promoter transactivation, wherein a cell which expresses the protein of any of claims 13–20 or the peptide of claim 21 and which contains a promoter having an E-box sequence (CACGTG) and a test substance are used (claim 39); the method for screening a promoter or a suppressor for the promoter transactivation according to claim 39, wherein the cell which expresses the protein of any of claims 13–20 or the peptide of claim 21 and which contains a promoter having an E-box sequence (CACGTG) is thehost cellof claim 28 or 29 (claim 40); amethodfor screening a promoter or a suppressor for the transactivation for a promoter having an E-box sequence (CACGTG) in the non-human animal of claim 30 or 31, wherein the non-human animal and a test substance are used (claim 41); a promoter of the promoter transactivation obtained by the screening method according to any of claims 39–41 (claim 42); a suppressor for the promoter transactivation obtained by the screening method according to any of claims 39–41 (claim 43); and a method for diagnosing diseases associated with the expression or the activity of BMAL2, wherein the DNA sequence encoding BMAL2 in a sample is compared with the DNA sequence encuding the protein of claim 13 or 14 (claim 44).

BRIEF DESCRIPTION OF DRAWINGS

FIG. 1 shows the amino acid sequence of cPER2.

FIG. 2 shows the results of the amino acid homologies in domains among cPER2 and three mouse PER proteins (mPER1–3).

BEST MODE OF CARRYUNG OUT THE INVENTION

Figures 3, 4:
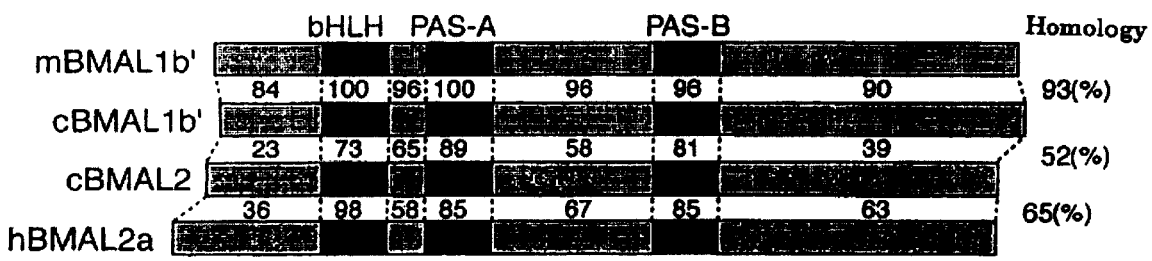
FIG. 3 shows the comparison among the amino acid sequences of various BMALs.
FIG. 4 shows the results of the amino acid homologies in domains among various BMAL proteins.

Proteins of the present invention are exemplified by novel proteins with BMAL2 activity including: human BMAL2 shown by Seq. ID No. 2, 4, 6 or 8; chicken BMAL2 shown by Seq. ID No. 10; mouse BMAL2 shown by Seq. ID No. 12 or 14; rat BMAL2 shown by Seq. ID No. 16, 18 or 20; a protein comprising an amino acid sequence wherein one or a few amino acids are deleted, substituted or added in the amino acid sequence shown by Seq. ID No. 2, 4, 6, 8, 10, 12, 14, 16, 18 or 20, and having BMAL2 activity; and the like. Here the BMAL2 activity is taken to mean an activity to form a heterodimer with a transcription-promoting element to promote transcription via E-box in the promoter of a clock oscillator gene, and to form a homodimer to bind to E-box to competitively suppress transcription. Any peptide comprising part of the above-mentioned proteins and having BMAL2 activity may serve as a peptide as an object of the present invention, however, a peptide having a basic helix-loop-helix (bHLH) structure or a PAS (Per-Arnt-Sim) domain is preferable. Proteins and peptides as objects of the present invention and the recombinant proteins and peptides to which the antibodies, specifically binding to these proteins and peptides, bind specifically may collectively be referred to as "the present proteins/peptides" hereinafter. The present proteins/peptides can be prepared in accordance with known methods base on their DNA sequence information or the like and there should be no limitation as to the origin of the proteins/peptides.

Any DNA may be an object of the present invention as long as the DNA encodes the present proteins/peptides mentioned above and the specific examples include DNA encoding human BMAL2 shown by Seq. ID No. 2, 4, 6 or 8, DNA encoding chicken BMAL2 shown by Seq. ID No. 10, DNA encoding mouse BMAL2 shown by Seq. ID No. 12 or 14, DNA encoding rat BMAL2 shown by Seq. ID No. 16, 18 or 20; DNA encoding a protein comprising an amino acid sequence wherein one or a few amino acids are deleted, substituted or added in the amino acid sequence shown by Seq. ID No. 2, 4, 6, 8, 10, 12, 14, 16, 18 or 20 and having BMAL2 activity; and DNA containing the base sequence shown by Seq. ID No. 1, 3, 5, 7, 9, 11, 13, 15, 17 or 19 or its complementary sequence and part or whole of these sequences. These can be prepared by known methods from, for instance, a gene library or cDNA library and the like of human, chicken, mouse, rat, etc., based on their DNA sequence information or the like.

DNA encoding a protein having BMAL2 activity of the interest which has the same effect as human BMAL2, chicken BMAL2, mouse BMAL2, rat BMAL2, etc. can be obtained by hybridization with various DNA libraries under a stringent condition by using as a probe the base sequence shown by Seq. ID No. 1, 3, 5, 7, 9, 11, 13, 15, 17 or 19 or its complementary sequence and part or whole of these sequences, and by subsequent isolation of DNA which hybridized with the probe. DNAs thus obtained are also within the scope of the present invention. One example of a hybridization condition for obtaining DNA of the present invention is hybridization at 42° C. and washing at 42° C. in a buffer solution containing 1×SSC, 0.1% SDS, and more preferable example is hybridization at 65° C. and washing at 65° C. in a buffer solution containing 0.1×SSC, 0.1% SDS. There are number of factors other than the temperature condition mentioned above that affect the hybridization stringency and those skilled in the art can actualize the same stringency as that for the hybridization referred to in the above by appropriately combining various factors.

Any fusion protein and fusion peptide may be used as a fusion protein and a fusion peptide for the present invention as long as the present proteins/peptides are bound with marker proteins and/or peptide tags. As for a marker protein, there is no limitation as long as it is a conventionally known marker protein and the specific examples include alkaline phosphatase, the Fc region of an antibody, HRP, GFP, etc. Conventionally known peptide tags including Myc tag, V5 tag, HA tag, His tag, FLAG tag, S tag, etc. are the specific examples of a peptide tag for the use in the present invention. Such fusion protein can be generated according to ordinary protocols and is useful for the following: purification of the various BHAL2 or the like by using affinity of Ni-NTA and His tag; detection of a protein which interacts with various BMAL2; quantification of an antibody against various BMAL2 or the like; and use as a laboratory reagent in this field of art.

Antibodies that specifically bind to the aforementioned proteins and peptides of the present invention can be particularly exemplified by immune-specific antibodies including monoclonal antibodies, polyclonal antibodies, chimeric antibodies, single-stranded antibodies, humanized antibodies, etc. These antibodies can be generated according to ordinary protocols by using the above-mentioned various BMAL2 proteins or the like, or part of these proteins as an antigen. However, monoclonal antibodies are more preferable than the other sorts of antibodies mentioned because of their specificity. Antibodies such as the monoclonal antibodies are useful not only for diagnosis and treatment, such as missile therapy, for the circadian rhythm sleep disorders or the like including delayed sleep phase syndrome, non-24-hour sleep-wake syndrome, advanced sleep phase syndrome, time zone change syndrome, shift work sleep disorder, etc, but for elucidating the molecular mechanism of the circadian oscillation system.

Antibodies of the present invention are created by administering to an animal (preferably non-human) the present proteins/peptides, their fragments containing epitopes, or the cells expressing the proteins/peptides on the membrane surface, according to the conventional protocols. The monoclonal antibodies can be prepared, for instance, by any optional method that provides antibodies produced by cultured materials of continuous cell line such as a hybridoma method (Nature 256, 495–497, 1975), atriomamethod, ahumanB-cellhybridomamethod (Immunology Today 4, 72, 1983), and an EBV-hybridoma method (MONOCLONAL ANTIBODIES AND CANCER THERAPY, pp. 77–96, Alan R. Liss, Inc., 1985).

The preparation method for a single chain antibody (U.S. Pat. No. 4,946,778) can be adopted to prepare single-stranded antibodies to, the present proteins/peptides of the present invention mentioned above. Transgenic mice, other mammals, etc. can be used for expressing humanized antibodies. Clones expressing the present proteins/peptides can be isolated/identified using the antibodies mentioned above, and their polypeptides can be purified by affinity chromatography. Antibodies to the present proteins/peptides or to peptides containing their antigenic epitopes can possibly be used for diagnosis and therapy for circadian rhythm sleep disorders or the like including delayed sleep phase syndrome, non-24-hour sleep-wake syndrome, advanced sleep phase syndrome, time zone change syndrome, shift work sleep disorder, etc, and are useful for elucidating the molecular mechanism of the circadian oscillation system. Furthermore, recombinant proteins or peptides to which these antibodies specifically bind are also covered by the present proteins/peptides of the present invention as described earlier.

The functions of the present proteins/peptides can be analyzed by using, for example, antibodies such as the aforementioned monoclonal antibodies labeled with fluorescent materials including FITC (Fluorescein isothiocyanate), tetramethylrhodamine isothiocyanate, etc., radioisotopes including $^{125}I$, $^{32}P$, $^{14}C$, $^{35}S$, $^{3}H$, etc., or enzymes including alkaline phosphatase, peroxidase, β-galactosidase, phycoerythrin, etc., or fused with fluorescent proteins such as Green Fluorescent Protein (GFP), BFP, CFP, YFP, RFP, etc. to serve as fusion proteins. As for immunological detection methods using the antibodies of the present invention, RIA method, ELISA method, fluorescent-antibody method, plaque method, spot method, haemagglutination, Ouchterlony method, etc. are exemplified.

There is no particular limitation as to a host cell of the present invention as long as the host cell comprises an expression system capable of expressing the present proteins/peptides. However, a preferable host cell is such in which the genes encoding CLOCK and/or BMAL1 are incorporated so that the two proteins can be simultaneously expressed in the host cell. Even more preferably, the host cell is incorporated with a DNA fragment which at least contains a promoter having E-box sequence (CACGTG), e.g. promoters of Per gene, Tim gene, Cry gene, vasopressin gene, the albumin D-site binding protein gene, etc., or a promoter introduced with E-box sequence (CACGTG) or the like. Although there is no particular limitation as to the above-mentioned DNA fragment so far as the fragment contains a promoter having E-box sequence (CACGTG), it is preferable for readily detecting and measuring the promoter activity that the DNA fragment is linked with a reporter gene including chloramphenicol acetyltransferase (CAT) gene, luciferasegene, etc., ageneencodingafluorescent protein including a short-lived green fluorescent protein (d1EGFP), etc. or with a fusion of GFP gene and a clock oscillator gene, and the like, to the down-stream of the promoter. Further, as to a promoter introduced with E-box sequence (CACGTG), any promoter may be adopted as long as its promoter activity can be regulated by a promoting element including the present proteins/peptides, CLOCK, BMAL1, etc. or by a suppressing element including PER, TIM, CRY, etc. These promoters are exemplified by RSV promoter, trp promoter, lac promoter, recA promoter, λPL promoter, lpp promoter, SPO1 promoter, SPO2 promoter, penP promoter, PHO5 promoter, PGK promoter, GAP promoter, ADH promoter, SRα promoter, SV40 promoter, LTR promoter, CMV promoter, HSV-TK promoter, etc., but the promoters will not be limited to these exemplifications alone.

The present proteins/peptides and genes such as CLOCK and BMAL1 can be introduced into host cells by methods described in many standard laboratory manuals such as a manual of Davis et al. (BASIC METHODS IN MOLECULAR BIOLOGY, 1986), of Sambrook et al. (MOLECULAR CLONING: A LABORATORY MANUAL, 2nd Ed., Cold Spring Harbor Laboratory Press, Cold Spring Harbor, N.Y., 1989) and the like. The methods include calcium-phosphate transfection, DEAE-dextran-mediated transfection, transvection, microinjection, cationic lipid-mediated transfection, electroporation, transduction, scrape loading, ballistic introduction, infection, etc. The examples of host cells include bacterial prokaryotic cells such as *E. coli, Streptomyces, Bacillus subtilis, Streptococcus, Staphylococcus*, etc., eukaryotic cells such as yeast, *aspergillus*, etc., insect cells such as *Drosophila* S2, *Spodoptera* Sf9, etc., animal cells such as L cell, CHO cell, COScell, HeLacell, C127 cell, BALB/c3T3 cell (includingmutant strains deficient in dihydrofolate reductase, tymidine kinase, etc.), BHK21 cell, HEK293 cell, Bowes malignant melanoma cell, etc. and plant cells or the like.

There is no limitation to an expression system as long as the expression system is capable of expressing the present proteins/peptides described above in a host cell and the examples include chromosome-, episome- and virus-derived expression systems, for instance, vectors derived from bacterial plasmid, yeast plasmid, papovavirus such as SV40, vaccinia virus, adenovirus, fowlpox virus, pseudorabies virus and retrovirus, and vectors derived from bacteriophage, transposon and from the combination of these two, e.g. vectors derived from genetic factors of plasmid and bacteriophage such as cosmid and phagemid. Such expression system is not only for raising the expression and it may contain a regulatory sequence to regulate the expression.

Host cells comprising the above-mentioned expression systems and the present proteins/peptides obtained by culturing the cells can be used in a screening method of the present invention as described below. Further, the known methods can be adopted to collect and purify the present proteins/peptides from the cell culture, where the methods include ammonium sulfate- or ethanol-precipitation, acid extraction, anion- or cation-exchange chromatography, phosphocellulose chromatography, hydrophobic interaction chromatography, affinity chromatography, hydroxyapatite chromatography and lectin chromatography, and the high performance liquid chromatography is preferably used. As a column especially used for affinity chromatography, for instance, columns to which antibodies to the present proteins/peptides are bound are used, and when common peptide tags are added to the present proteins/peptides mentioned above, columns to which substances having affinity with the peptide tags are bound are used, in order to obtain the present proteins/peptides. The purification methods for the present proteins/peptides mentioned above may also be employed for peptide synthesis.

In the present invention, a non-human animal whose gene function to encode the present proteins/peptides mentioned above is deficient on its chromosome means a non-human animal part or whole of whose gene on its chromosome encoding the present proteins/peptides is inactivated by gene mutations such as destruction, deletion, substitutions, etc. and thus whose function to express the present proteins/peptides is lost. Further, a non-human animal which overexpresses the present proteins/peptides is specifically represented by a non-human animal which produces larger amount of the present proteins/peptides than a wild-type non-human animal does. Specific examples of non-human animals in the present invention include non-human animals such as rodents including mice, rats, etc., osteichthyes such as zebra fish, medaka fish, etc., arthropods such as *Drosophila*, silkworm, etc., the non-human animals should not be limited only to these examples.

Homozygous non-human animals that are born according to Mendel's Law include the deficient type or the over-expressing type for the present proteins/peptides as well as their wild type littermates. By using the deficient type animals or the over-expressing type animals of these homozygous non-human animals together with their wild-type littermates at the same time, accurate comparative experiments can be actualized out on the individual level. Therefore in performing screening of the present invention described below, it is, preferable to use wild type non-human animals, i.e. animals of the same species as, or even better the littermates of, non-human animals whose gene function to encode the present proteins/peptides is deficient or overexpressed on their chromosomes, in parallel with the deficient or over-expressed type animals. The method of generating a non-human animal whose gene function to encode the present proteins/peptides is deficient or over-expressed on its chromosome is now explained in the following with reference to a BMAL2 knockout mouse and a BMAL2 transgenic mouse.

A mouse, for instance, whose gene function to encode BMAL2 protein is deficient on its chromosome, i.e. a BMAL2 knockout mouse is generated by the following steps. A gene encoding mouse BMAL2 is screened by using a gene fragment obtained by a method such as PCR from a mouse gene library. A gene thus screened which encodes mouse BMAL2 is subcloned with a viral vector or the like and is identified by means of DNA sequencing. Then whole or part of a gene encoding BMAL2 among this clone is substituted with a pMC1 neo gene cassette or the like and then a gene such as a diphtheria toxin A fragment (DT-A) gene, a herpes simplex virus tymidine kinase (HSV-tk) gene, etc. is introduced onto either or both of 5'- or 3'-end, and thus a targeting vector is constructed.

The targeting vectors thus constructed are linearlized and introduced into ES cells by electroporation or the like to cause homologous recombination. Among the homologous recombinants, ES cells in which homologous recombination have occurred are selected by the use of antibiotics such as G418, ganciclovir (GANC), etc. It is preferable to confirm whether the ES cells selected are the recombinants of the interest by Southern blotting or the like. A clone of the ES cells thus confirmed is microinjected into a mouse blastocyst and which blastocyst is placed back to the recipient mouse to generate a chimeric mouse. A heterozygous mouse can be obtained by intercrossing the chimeric mouse and a wild type mouse. By further intercrossing the heterozygous mice, a BMAL2 knockout mouse of the present invention can be generated. Whether the ability of expressing BMAL2 is lost in the BMAL2 knockout mouse is examined by Northern blotting upon isolating RNA from the mouse obtained by the above-described method, and by Western blotting or the like in which the BMAL2 expression in the mouse can be directly examined.

A BMAL2 transgenic mouse is created by the following steps. A promoter such as chicken β-actin, mouse neurofilament, SV40, etc. and poly (A) such as rabbit β-globin, SV40, etc. or introns are fused with cDNA encoding BMAL2 derived from chicken, mouse, human, rat, etc., to construct a transgene. This transgene is microinjected into the pronucleus of a mouse fertilized egg. After the obtained egg cell is cultured, it is transplanted to the oviduct of the recipient mouse which was bred thereafter. Neonatal mice having the aforementioned cDNA were selected from among all the mice born and thus the transgenic mice are created. Neonatal mice having the cDNA can be selected by extracting crude DNA from the mice tails or the like and then by performing a dot hybridization method using a gene encoding the introduced BMAL2 as a probe and by PCR method or the like using a specific primer.

Genes or DNAs encoding the present proteins/peptides, the present proteins/peptides, fusion proteins in which the present proteins/peptides and marker proteins and/or peptide tags are bound, antibodies to the present proteins/peptides, host cells comprising expression systems capable of expressing the present proteins/peptides, CLOCK, BMAL1, etc., non-human animals whose gene function to encode the present proteins/peptides is deficient on their chromosome, non-human animals which over-express the present proteins/peptides and the like make it possible to elucidate the molecular mechanism of the circadian oscillation system. In addition to that, these can be used to screen a promoter or a suppressor for expression of the present proteins/peptides, a promoter or a suppressor for the Bmal2 activity, and a promoter or a suppressor for the promoter transactivation of the clock oscillator genes or the like. Some among the substances obtained by these screening methods may possibly be used for therapy of the circadian rhythm sleep disorders or the like including delayed sleep phase syndrome, non-24-hour sleep-wake syndrome, advanced sleep phase syndrome, time zone change syndrome, shift work sleep disorder, etc.

As for a screening method for a promoter or a suppressor for expression of the present proteins/peptides, or for a promoter or a suppressor for the Bmal2 activity of the present invention, methods are exemplified that use: cells expressing the present proteins/peptides and a test substance; and a non-human animal deficient in a gene function to encode the present proteins/peptides on its chromosome or a non-human animal overexpressing the present proteins/peptides and a test substance. A screening method using cells expressing the present proteins/peptides and a test substance, as mentioned above, can be exemplified by a method wherein a test substance is made to contact or introduced into, for instance, the cells expressing the present proteins/peptides, e.g. cells obtained from wild-type non-human animals, host cells of the present invention, cells obtained from transgenic non-human animals of the present invention, etc. and wherein the Bmal2 activity and changes in the expression levels of the present proteins/peptides are measured and assessed, but the methods should not be limited to these examples alone.

As for a screening method wherein a non-human animal whose gene function to encode the aforementioned present proteins/peptides is deficient on its chromosome or a non-human animal which over-expresses the present proteins/peptides is used along with a test substance, the examples specifically include: a method wherein a non-human animal whose gene function to encode the aforementioned present proteins/peptides is deficient on its chromosome or a non-human animal which over-expresses the present proteins/peptides, as mentioned above, is administered with a test substance and subsequently the Bmal2 activity and changes in the expression levels of the present proteins/peptides in the cells obtained from the non-human animal are measured and assessed; or a method wherein a non-human animal whose gene function to encode the aforementioned present proteins/peptides is deficient on its chromosome or a non-human animal which over-expresses the present proteins/peptides mentioned above is administered with a test substance and subsequently the Bmal2 activity and changes in the expression levels of the present proteins/peptides in the non-human animal are measured and assessed.

An example of a screening method of the present invention for a promoter or a suppressor of the promoter transactivation is a method wherein a test substance and a cell expressing either the present proteins/peptides or the present proteins/peptides along with CLOCK and/or BMAL1 and containing a promoter which has E-box sequence (CACGTG), more specifically a method in which a test substance is made to contact or introduced into the aforementioned cell and the promoter activity mediated by E-box is then measured and assessed. Another example is a method wherein a test substance is applied to a non-human animal whose gene function to encode the present proteins/peptides is deficient on its chromosome or to a non-human animal which over-expresses the present proteins/peptides to measure and assess the change in the promoter activity mediated by E-box. In addition, it is preferable to have reporter genes or the like, such as chloramphenicol acetyltransferase (CAT) gene or luciferase gene, linked to the downstream of a promoter having E-box sequence (CACGTG), in order to readily analyze the promoter activity.

The present invention also relates to a diagnostic method for diseases associated with the activity or expression of BMAL2 protein wherein the method comprises comparing the DNA sequence encoding BMAL2 protein in a sample with the DNA sequence encoding BMAL2 protein of the present invention. Mutants of DNA encoding BMAL2 protein can be detected by finding individuals with gene mutations at the DNA level, and such detection is effective for diagnosing with diseases developed by underexpression, overexpression or mutated expression of BMAL2 protein. Specific examples of samples used for the detection include cells of a subject, for example, genomic DNA obtainable biopsy of blood, urine, saliva, tissue, etc., or RNA or CDNA. The samples, however, should not be limited to these exemplifications and the amplified products of PCR or the like may also be employed in using the samples. Deletions or insertion mutations of a base sequence can be detected through the changes in size of the amplified products when compared to that of the normal gene type. Point mutation can be identified by hybridizing the amplified DNA with a gene encoding a labeled BMAL2 protein. As described in the above, the circadian rhythm sleep disorders or the like including delayed sleep phase syndrome, non-24-hour sleep-wake syndrome, advanced sleep phase syndrome, time zone change syndrome, shift work sleep disorder, etc. can be diagnosed or judged by detecting mutation in a gene which encodes BMAL2 protein.

The present invention is now further described specifically with reference to the examples, however, the scope of the invention should not be limited to these examples alone.

EXAMPLE 1

Cloning and Sequencing 1-1 (Cloning and sequencing of cClock cDNA)

cClock cDNA was amplified with the chicken pineal cDNA library (λZAPII, 5×10$^5$ pfu) as a template by PCR using LA-Taq polymerase (Takara) and a pair of primers [sense primer 1: 5'-ACTAGTCGACTTATGTTTTTTAC-CATAAGCACC-3' (Seq. ID No. 21), antisense primer 1: 5'-GTCGACCTGCGCTACTGTGGCTGAGCTTTG-3' (Seq. ID No. 22); Each of the primers has a SalI site on its 5'-terminal] which were designed on the basis of the sequences of cClock genes deposited in GenBank (GenBank accession nos. AF132531 and AF144425). The above-mentioned PCR method was performed for different times and the sequences of the five clones obtained were determined. One clone with no PCR error was selected (GenBank accession no. AF246959). The program for thermal cycles was as follows: degeneration for 1 min at 94° C. only for the first time, followed by 5 repetitive cycles each consisting of thermal degeneration for 30 sec at 94° C., annealing for 30 sec at 55° C. and extension for 3.5 min at 72° C.; followed by 15 repetitive cycles each consisting of thermal degeneration for 30 sec at 94° C., annealing fur 30 sec at 65° C. and extension for 3.5 min at 72° C.; and finally extension for 6.5 min at 72° C.

1–2 (Cloning and sequencing of cPer2 cDNA)

A 273 bp fragment of cPer2 cDNA was obtained from a chicken pineal cDNA library by PCR using Taq-Gold polymerase (PE applied biosystems) and a pair of degenerate primers [per-F, 5'-CAGCAGAT(C/G)A(A/G)CTG(C/T)IT(C/G)IGACAG(C/T)(A/G)TC(A/C)TCAG-3' (Seq. ID No. 23) and per-R, 5'-GCT(A/G)CACTG(A/G)CTG(A/G)TG(A/C)(C/G)IGAC(A/G)CCAC(A/G)CTC-3' (Seq. ID No. 24)] which were designed based on the nucleotide sequences of dPer and mammalian Per genes. A longer cDNA fragment (P2–5; 886bp) was amplified from a chicken pineal cDNA library by the subsequent PCR using cPer2-R1 primer [5'-TTGCTGTACCAGGCACATTACAAC-3' (Seq. ID No. 25)] synthesized from the base sequence of the above-obtained fragment, a degenerate primer [YK-F1; 5'-(A/G)TICA(C/T)TCIGGITA(C/T)CA(A/G)GCICCI(A/C)GIAT-ICC-3' (Seq. ID No. 26)] and LA-Taq polymerase. This fragment was used as a hybridization probe for the screening of the chicken pineal cDNA library (λZAPII, 5×10⁵ pfu) to isolate a clone Pa (3584 bp) encoding a larger part of cPER2 (Met$^1$-Arg$^{1014}$). This clone and the cDNA clone obtained by 3'-RACE were ligated together to generate a full-length clone for cPER2 (Met$^1$-Thr $^{1344}$; GenBank accession no. AF246956). The result is shown in FIG. 1 in which the DNA sequence and the amino acid sequence are shown as Seq. ID Nos. 27 and 28 respectively. The bars above the sequence in FIG. 1 indicate the PAS domains (PAS-A and PAS-B) and the cytoplasmic localization domain (CLD). FIG. 2 shows the amino acid homologies in domains between cPER2 obtained as above and three mouse PER proteins (mPER1–3). The programming for thermal cycles of the above was as follows: degeneration for 1 min at 94° C. only for the first time; followed by 35 repetitive cycles each consisting of thermal degeneration for 30 sec at 94° C., annealing for 60 sec at 52° C. and extension for 1 min at 72° C.; and finally extension for 9 min at 72° C.

1–3 (Cloning and sequencing of cBmal cDNA)

cDNA clones encoding part of cBMAL1 or cBMAL2 were respectively obtained from the chicken pineal cDNA library by PCR using LA-Taq polymerase with degenerate primers [BMAL-F, 5'-GTGCT(A/C)(A/C)GGATGGC(A/T)GT(G/T)CAGC-3' (Seq. IDNO. 29) and BMAL-R, 5'-GCG(C/T)CC(A/G)ATTGC(A/C/G)AC(A/G)AGGCAG-3' (Seq. ID No. 30)] which were designed based on nucleotide sequences of Bmal1 of mouse, rat and human and dCycle of Drosophila. Each amplified fragment and a cDNA clone of the each amplified fragment obtained by 5'-RACE were used as probes for screening the chicken pineal cDNA library (λZAPII, 3.5×10⁵ pfu) and cDNA clones containing the coding regions for cBMAL1b' (GenBank accession no. AF246957) and cBMAL2 (GenBank accession no. AF246958) were respectively isolated and sequenced (FIG. 3). The bars above the sequences in FIG. 3 indicate the basic helix-loop-helix region (bHLH) and PAS domains (PAS-A and PAS-B). PCR for the above was performed using a thermal cycler (Perkin-Elmer) as follows: thermal degeneration for 1 min at 94° C. only for the first time; followed by 35 repetitive cycles each consisting of thermal degeneration for 30 sec at 94° C., annealing for 1 min at 50° C. and the extension reaction for 1 min at 72° C.; and finally extension for 9 min at 72° C.

The initiation methionine of cBMAL1b' was predicted by comparing the cBMAL1b' sequence mentioned above and the BMAL1 sequences of other animal species. The initiation methionine of the aforementioned cBMAL2 was predicted by the following three criteria; (i) A nonanucleotide sequence (CCGCCATGG), the 97–105 base sequence of cBmal2 shown as Seq. ID No. 9, fully matched the Kozak's translation initiation consensus sequence (Nucleic Acids Res. 12. 857–872, 1984). (ii) The above-mentioned Bmal2 cDNA clone (3.4 kb) and mRNA (3.0, 3.8 kb) were similar in size to each other. (iii) A promoter region predicted from its genomic analysis contained the upstream inframe stop codons.

Figures 5, 6:
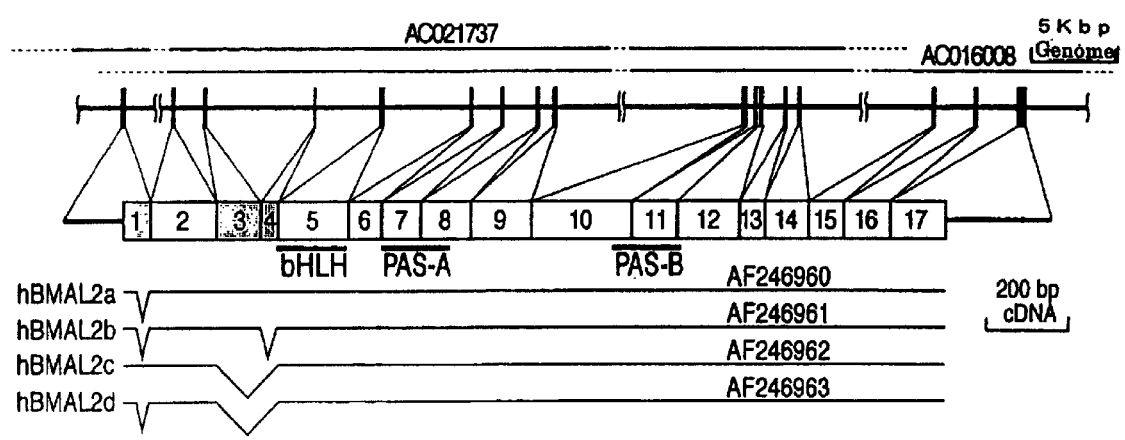
FIG. 5 shows the phylogenetic tree of ARNT-BMAL proteins and their amino acid homologies with cBMAL2 or hBMAL2.
FIG. 6 shows the genomic structure of hBMAL2 gene of the present invention.

Next, the amino acid homologies in domains among mBMAL1b' and three novel BMAL proteins (cBMAL1b', cBMAL2 and hBMAL2a) were analyzed and a phylogenetic tree of ARNT and BMAL proteins was constructed according to Neighbor-joining method using PHYLIP, v.3.572 as described in the literature (Felsenstein, J., PHYLIP, Version 3.572, University of Washington, Seattle, 1996). These results are respectively shown in FIGS. 4 and 5. In FIG. 5, since amino acids in cBMAL2 in the amino-terminal region (Met$^1$-Arg$^{104}$) and carboxy-terminal region (Gly$^{459}$-Leu$^{622}$) differ in number among animal species, a part corresponding to this region was omitted from each protein before calculating the amino acid homologies among the proteins, and then the phylogenetic tree was constructed. These results demonstrate that cBMAL1b' is 93% homologous to mBMAL1b' to show they are close to one another (FIGS. 3 and 4), while cBMAL2 (ARNT4) is not particularly close to BMAL1 (70%; FIG. 5) nor to ARNT1 (41%; FIG. 5) nor to ARNT2 (40%; FIG. 5) and hence that cBMAL2 is a novel protein having bHLH-PAS (FIG. 4).

1–4 (Cloning and sequencing of hBmal2 cDNA)

A partial sequence information of hBmal2 was obtained from two human EST clones (GenBank accession nos. AA577389 and AI218390) by in silico screening using cBmal2 as a probe (data as of October 1999). Several cDNA clones containing the 5'-untranslated region of hBmal2 gene were isolated from cDNA of 293EBNA cell (a human embryonic kidney cell line) by 5'-RACE. Then full-length-clones were amplified by PCR using hB2F1 and hB2R1primers [hB2F1, 5'-GACCAAGTGGCTCCTGC-GAT-3' (Seq. ID No. 31) and hB2R1, 5'-GCTAGAGGGTC-CACTGGATG (Seq. ID No. 32)]. To eliminate PCR errors, 17 full-length cDNA clones obtained were sequenced, and all the DNA sequences encoding hBMAL2a–d (GenBank accession nos. AF246960-AF246963), which were consistent with the human genomic sequences (GenBank accession nos. AC021737 and AC016008), were determined. The programming for the PCR thermal cycles mentioned above was as follows: degeneration for 1 min at 94° C. only for the first time; followed by 20 repetitive cycles each consisting of thermal degeneration for 30 sec at 94° C., annealing for 60 sec at 60° C. and extension for 2 min at 72° C.; and finally extension for 8 min at 72° C. These results are shown in FIGS. 3, 4 and 5. The arrowheads below the sequences in FIG. 3 indicate the insertion sites of introns in hBmal2 gene.

cDNA sequences encoding 4 variants of hBAML2 (hBMAL2a–d) and obtained from 293EBNA cells as described above, were compared with the genome sequences registered at GenBank (accession nos. AC021737 and AC016008). Then the cDNA sequences were divided into 17 exons as in the case of mBmal1 (Biochem. Biophys. Res. Commun. 260, 760–767, 1999) to examine the genomic organization of hBmal2. The results are shown in FIG. 6. Bars with GenBank accession numbers in FIG. 6 represent genomic and CDNA clone regions and shaded parts are the spliced regions in the isolated mutants. These results show that the cDNA clone of hBMAL2b is devoid of Exon 4 (corresponding to $Val^{96}$-$Arg^{109}$ in hBMAL2a) and that of hBMAL2c is devoid of both Exons 3 and 4 (corresponding to $Gln^{75}$-$Arg^{109}$ in hBMAL2a) and having Exon 1 to which DNA encoding the amino acid sequence of 11 amino acid residues (GEVAGGEATAP) added in-between $Gly^{10}$ and $Gly^{11}$ in hBMAL2a is extended. hBMAL2d was revealed to be the shortest mutant which is devoid of both Exon 1 (as in hBMAL2a/b) and Exons 3/4 (as in hBMAL2c) in cDNA.

1–5 (Cloning and sequencing of mBmal2 cDNA)

Figure 7:
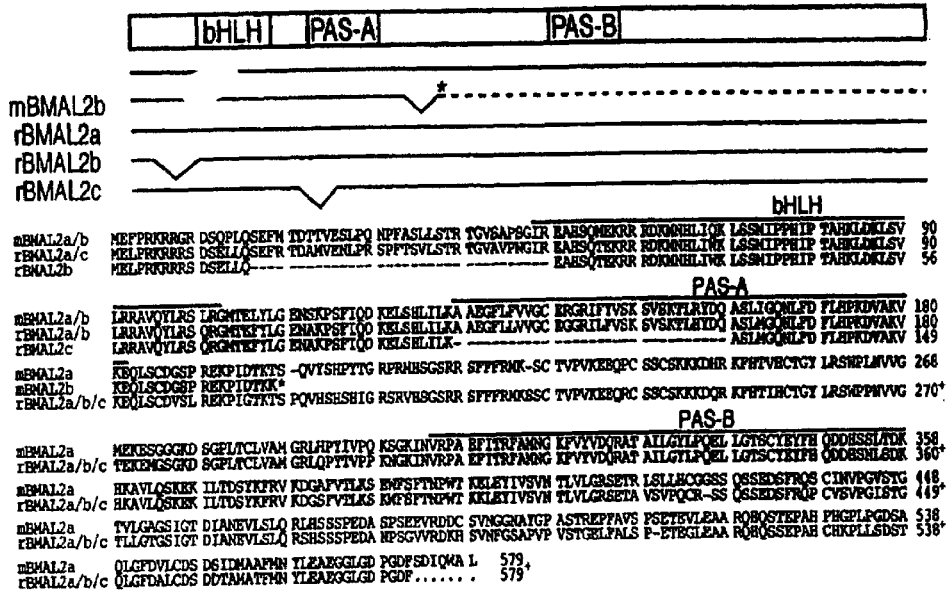
FIG. 7 shows the basic structure of mouse BMAL2 and rat BMAL2 of the present invention.

To identify the mouse Bmal2 ortholog (mBmal2) expressed in the suprachiasmatic nuclei (SCN), a 629 bp fragment CDNA was obtained by RT-PCR for total RNA extracted from the mouse mid-brain, by using LA-Taq polymerase (Takara) and two primers synthesized according to the hBmal2 sequence; hBMAL2-F4: 5'-GTGCTGGTAG-TATTGGAACAGATATTG-3' (Seq. ID No. 33) and hBMAL2-R1: 5'-GCTAGAGGGTCCACTGGATG-3' (Seq. IDNo. 34). Subsequently, several cDNA clones were isolated which contain 5'- or 3'-untranslated region of mBmal2 cDNA by the method of 5'- and 3'-rapid amplification of cDNA ends. Based on these sequence information, two primers [mBMAL2-F1: 5'-GGTCGACCACCATG-GAGTTTTCCAAGGAAACG-3' (Seq. ID No. 35), mBMAL2-R1: 5'-GCTAGAGTGCCCACTGGATGTCAC-3' (Seq. ID No. 36)] were designed that were capable of amplifying full-length clones covering the total coding sequence of mBMAL2a or mBMAL2b (FIG. 7; GenBank accession nos. AY005163 and AY014836). Another RT-PCR was performed using these primers and LA-Taq polymerase to obtain mBMAL2a comprising 579 amino acid residues. This amino acid sequence contained bHLH, PAS-A and PAS-B domains and was homologous to hBMAL2 by 74%, cBMAL2 by 63% and zBMAL2 by 48%. On the contrary, mBMAL2b consists of amino acid residues that are about one third of those of mBMAL2a (199 amino acid residues) and is devoid of PAS-B domain (FIG. 7). Although this form of mutation is similar to that previously found in hBMAL1c (a BMAL1 mutant devoid of the C-terminal half in the BMAL1 comprising a long chain; Biochem. Biophys. Res. Commun. 233, 258–264, 1997), its physiological meaning is yet unknown.

1–6 (Cloning and sequencing of rBmal2 cDNA)

Next, cDNA clone of rat Bmal2 (rBmal2) covering almost a total coding region was isolated from the rat early fibroblast rat-1 cells by RT-PCR using two primers [mBMAL2-F1 and mBMAL2-R1]. Three clones isolated, rBMAL2a–c, were determined for the amino acid sequences (FIG. 7; respectively registered to GenBank under GenBank accession nos. AF327071, AY014837, AY014838). The amino acid sequence at the amino-terminal in rBmal2 (corresponding to the position of mBMAL2-F1 primer) was obtained from the in silico screening (GenBank accession no. AA944306). These results demonstrate that rBMAL2a comprising the longest sequence among the clones obtained is most similar to mBMAL2a in its structure. In FIG. 7, dots at the end of the rBMAL2 sequence indicate the position corresponding to mBMAL2-R1, a PCR primer. The asterisk indicates the position of the in-frame stop codon of mBMAL2b and the number at the end of each line (with "+" on the right shoulder) indicates the number of amino acid residues for rBMAL2a.

Figure 8:
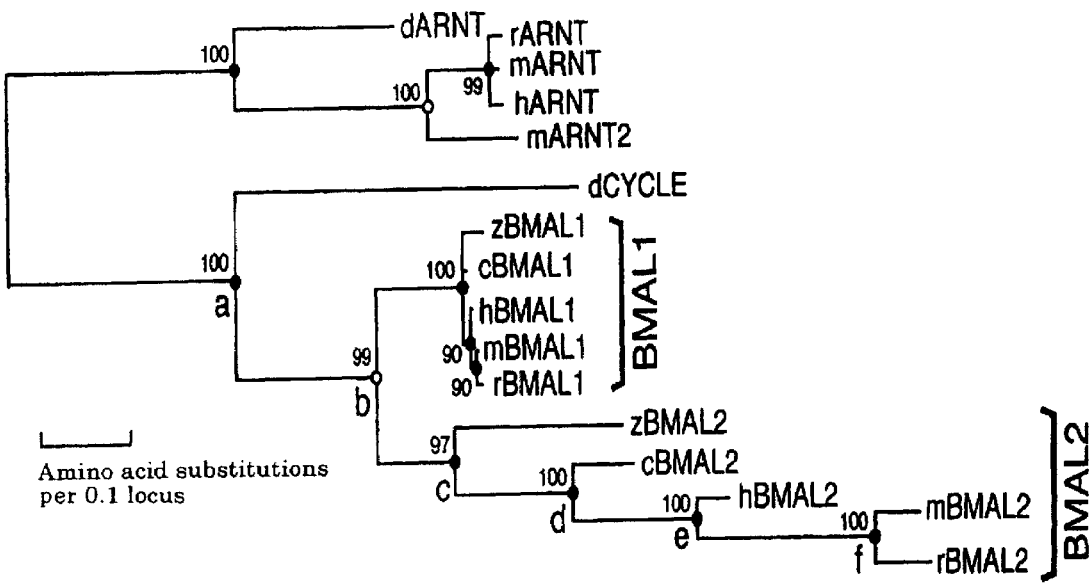
FIG. 8 shows the phylogenetic tree of the BMAL-ARNT family proteins.

Next, the phylogenetic tree for the BMAL-ARNT family was constructed according to the amino acid homologies among various proteins (FIG. 8). Before constructing the phylogenetic tree, several amino acid sequences of BMAL-ARNT proteins that were obtained from GenBank were aligned with Gene Works (Ver.2.55, clustal V), then some regions with gaps were omitted. Since the length of amino acids in amino- and carboxyl-terminal regions (corresponding to the 1–59 amino acid sequence and the 413–579 amino acid sequence of mBMAL2a) differ among mutants, these regions were also omitted. Then the Neighbor-joining tree was constructed using a PHYLIP 3.572 software package (Felsenstein, J., PHYLIP, Version 3.572, University of Washington, Seattle, 1996) (FIG. 8), and the topology of the phylogenetic tree obtained as above was analyzed by PROTML 2.3 program which adopts a local rearrangement method for the maximum likelihood analysis and JTT-F model for the amino acid substitution (Adachi, J. and Hasegawa, M., MOLPHY: Programs for molecular phylogenetic based on maximum likelihood, Version 2.3, Institute of Statistical Mathematics, Tokyo, 1996). Further, in order to assess the reliability of that phylogenetic tree, a boot strap test was carried out and the boot strap probabilities of over 70% were respectively shown near the diversion points in FIG. 8. The diversion points shown by closed circles indicate the divergence of species and those shown by open circles indicate gene duplications in FIG. 8.

When the above result is taken into account together with the fact that there is only a single copy of dCyc gene, a Bmal1/2-like gene, in the Drosophila genome, Bmal1 and Bmal2 genes are likely to be generated from the gene duplication occurred in their ancestral vertebrates (Diversion point b in FIG. 8). Besides, branches at the divergence among the members in the BMAL2 cluster are much longer than those of BMAL1, meaning that the phylogenetic tree topology in the BMAL2 cluster reflects the phylogenetic development of vertebrates. It can therefore be concluded from these facts that these Bmal2 genes are in orthologous relationships with each other and have developed from a highly frequent amino acid substitution. This conclusion can also be supported by the fact that no m/r/c/z Bmal2 orthologs other than hBmal2 can be found in the human gene data base (the htgs database was searched on $9^{th}$ Dec., 2000). Diversion point a in FIG. 8 probably indicates divergence between ancestors of vertebrates and arthropods and diversion points c–f indicate divergence among vertebrate species. Besides, the above-mentioned phylogenetic tree had the same topology as phylogenetic trees obtained by Parsimony and Neighbor-joining methods.

Comparison of substitution rates in amino acids among the members of BMAL1/2 clusters revealed that the amino acid substation rate of BMAL2 is higher than that of BMAL1 by about 20-fold. This shows that the selective pressure in BMAL2 after gene duplication is lower than that in BMAL1. What is important is that there is no any specific region in which the total amino acid homology among BMAL2 proteins is decreased. Highly conserved structure of BMAL1 protein which has a higher selective pressure is thought to include some unrecognized function which has been lost in BMAL2. BMAL1 is thought to interact with several essential regulatory factors that have not yet been characterized, because both BMAL proteins interact with CLOCK which is a functional heterodimer partner with BMAL proteins (Science 280, 1564–1569, 1998, Proc. Natl. Acad. Sci. USA 97, 4339–4344, 2000, J. Neurosci. 20, RC83, 2000, J. Biol. Chem. 275, 36847–36851, 2000, Proc. Natl. Acad. Sci. USA 95, 5474–5479, 1998, Biochem. Biophys. Res. Commun. 248, 789–794, 1998), with a neuron PAS domain protein 2 (NPAS2 or MOP4) (J. Neurosci. 20, RC83, 2000, Proc. Natl. Acad. Sci. USA 95, 5474–5479, 1998), with a hypoxia-inducing factor 1α(HIF1α) (J. Neurosci. 20, RC83, 2000, Proc. Natl. Acad. Sci. USA 95, 5474–5479, 1998, Biochem. Biophys. Res. Commun. 248, 789–794, 1998),or with HIF2α(HLF or EPAS1) and with the like. Therefore, analyzing the differences between the functions of BMAL1 and BMAL2 is thought to contribute to uncover their unique evolution processes.

EXAMPLE 2

Northern Blot Analysis

Figure 9:
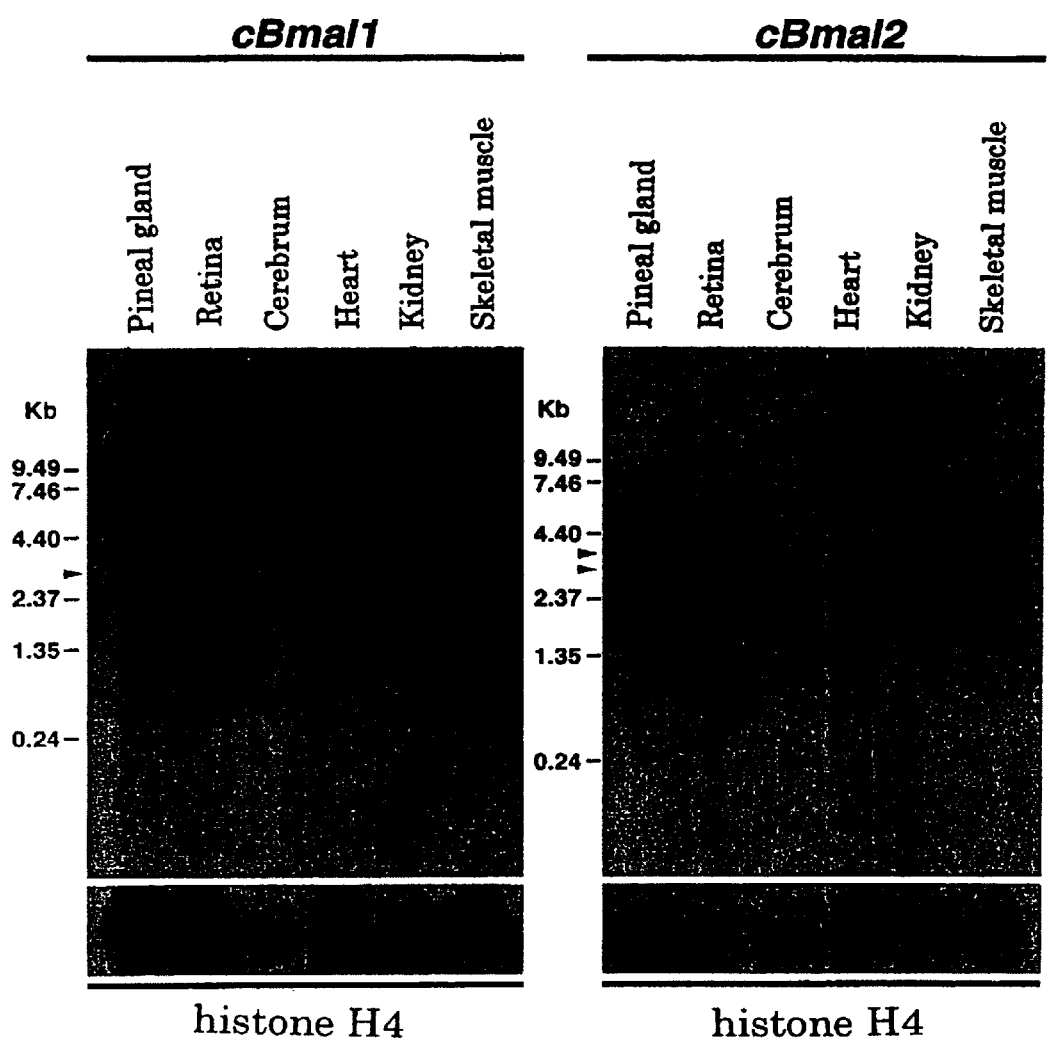
FIG. 9 shows the results of the northern blotting for analyzing the expressions of cBmal2 and cBaml1 genes of the present invention.

Total RNA (7.5 μg) of each tissue from one-week-old chicks (pineal gland, retina, cerebrum, heart, kidney and skeletal muscle) was analyzed by Northern blotting in a manner as described in J. Neurochem. 70, 908–913, 1998. These tissues were harvested at 0, 6, 12 and 18 hr in Zeitgeber time (ZT), frozen with liquid nitrogen and mixed before extracting RNA. Each of total RNA was separated by an agarose gel electrophoresis and blotted on a nitrocellulose membrane. The blotting membrane was hybridized with a cBmal1 probe or a cBmal2 probe and washed (10 min×3 times) in 0.1×SSC at 50° C., then analyzed using a FLA2000 bioimage analyzer (FUJI PHOTO FILM). The membrane was subsequently hybridized with a chicken histone H4cDNA probe and analyzed. The chicken histone H4cDNA probe used was prepared by amplification by PCR with a primer [sense primer 2; 5'-CATGTCTGGCAGAG-GCAAG-3' (Seq. ID No. 37) and antisenseprimer2; 5'-TTAGCCGCCGAAGCCGTAG-3' (Seq. ID No.38)], which was designed from the chicken pineal cDNA based on the sequence (accession no. M74533) deposited in GenBank, and by the subsequent cloning. The results are shown in FIG. 9. These results demonstrate that two cBmal2 genes (3.8 Kb and 3.0 Kb, indicated by arrows) and cBmal1 gene (3.3 Kb) are expressed in all the tissues examined at various intensities. It was confirmed as a result of normalization to histone H4 that heart and kidney exhibited low transcriptional levels of cBmal1 and that no apparent difference was observed in the transcriptional levels of cBmal2 among the tissues examined.

EXAMPLE 3

Expression of Chicken Clock Genes in the Pineal Gland

Figure 10:
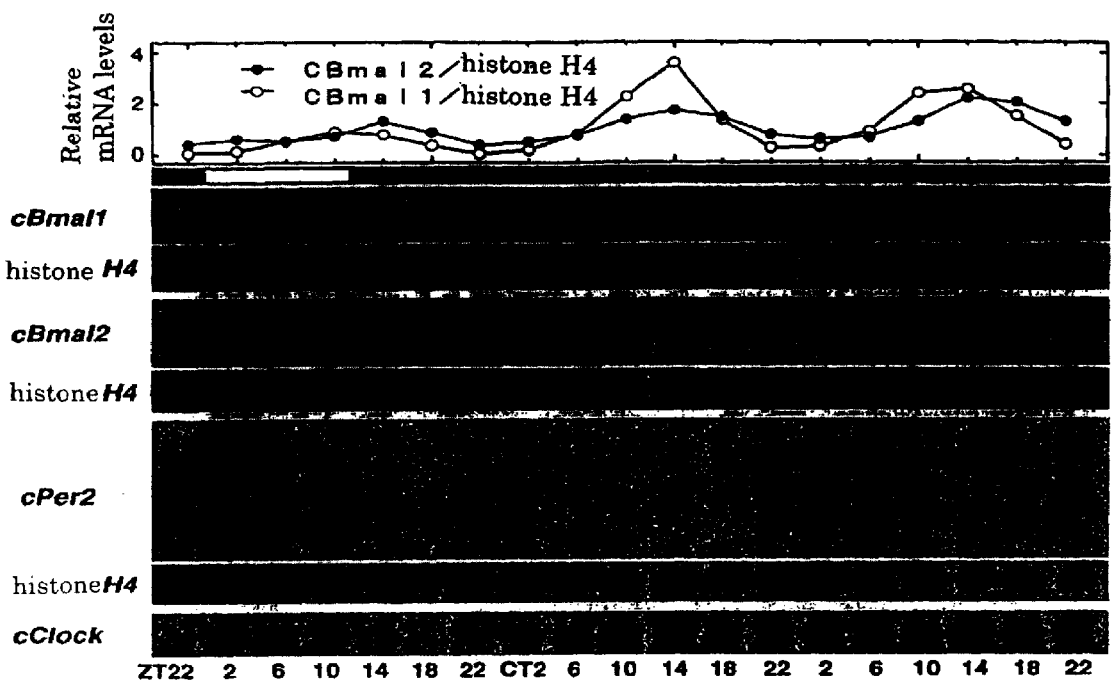
FIG. 10 shows the results of time-course changes in mRNA levels of cBmal1, cBmal2, cPer2 and cClock in the chicken pineal glands of the individuals.

One-day-old chicks were entrained to LD cycle (12 hr with light/12 hr in the dark) for 3 weeks, then placed in DD (constant darkness) condition for 2 days, and the pineal glands were collected every 4 hr over the last 3 days. Total RNA from each pineal gland was analyzed by Northern blotting to detect expression of chicken Clock genes (cBmal1, cBmal2, cPer2 and cClock) in the pineal gland. Total RNA (6 μg) obtained from each pineal gland mentioned above was separated by an agarose gel electrophoresis, blotted on a nitrocellulose membrane. Two such blotting membranes were prepared. A blot was first hybridized with a cBmal2 probe or a cPer2 probe and the blotting membrane was washed in 0.1×SSC at 50° C. (10 min×3 times), which was then analyzed using a FLA2000 bioimage analyzer (FUJI PHOTO FILM). Next, the blot was hybridized with the histone H4cDNA and analyzed in the same way. The aforementioned cDNA fragment P2–5wasusedas the cPer2 probe. For another blotting membrane, the blot was first hybridized with a cBmal1 probe as in the above, then with a histone H4cDNA and finally with a cClock probe, and was analyzed with a FLA2000 bioimage analyzer. These results are shown in FIG. 10 (bottom lane). Signals for cBmal1 (open circles) and cBmal2 (closed circles) were quantified by MacBAS software (FUJI PHOTO FILM), normalized to those for the histone H4 cDNA, and the mean value was set as 1 in each case to analyze the time-course changes in transcriptional levels of the chicken Clock genes. The results are shown in FIG. 10 (top lane). A cross bar above the Northern blotting results in FIG. 10 indicates light and bright cycles. An open region indicates a light cycle, closed regions indicate (subjective) dark cycles and shaded regions indicate subjective light cycles. Three cPer2 transcripts (9.7 Kb, 7.5 Kb and 4.1 Kb) and a single cClock transcript (8.5 Kb) were confirmed by these results.

EXAMPLE 4

Expression of Chicken Clock Genes in the Pineal Cell Culture

Figure 11:
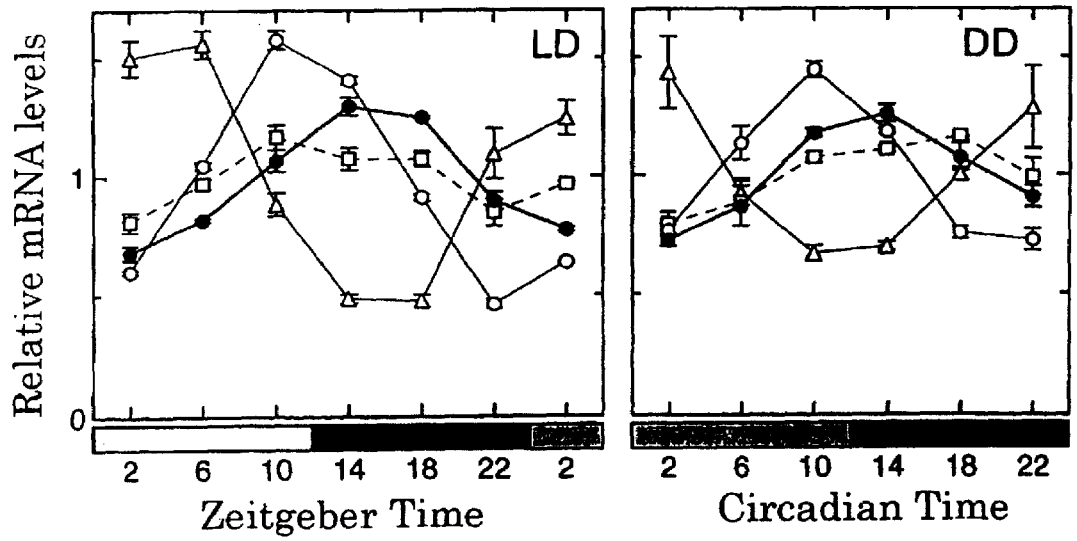
FIG. 11 shows the time-course changes in mRNA levels of cBmal1, cBmal2, cPer2 and cCLOCK in the cultured chicken pineal cells under LD or DD condition.

The time course changes in the transcription amounts of chicken clock genes [cBmal1 (open circle), cBmal2 (closed circle), cPer2 (open triangle) and cClock (open square)] in the pineal cell culture were analyzed by a quantitative RT-PCR method and the results were compared to those in Example 3 above (FIG. 11). Pineal cells from one-day-old chicks were plated on 35 mm dishes (cells from 8 pineal glands per a dish) and cultured for 5 days under LD cycles in Medium 199 (Life Technologies) supplemented with 10% fetal bovine serum. On day 6, part of the cultured cells was shifted to culture under constant darkness (DD, right in FIG. 11). The rest of the cultured cells remained in the culture under the LD condition and subjected to a further culture on day 7 under constant darkness (LD, left in FIG. 11). Then each pineal cell was harvested every 4 hours. The pineal cells harvested were suspended in TRIzol reagent (Life Technologies) and stored at −80° C. until total RNA was isolated. 1 μg each of the total RNA was reverse-transcribed by the SuperScriptII (Life Technologies) reverse transcriptase and a portion of the reaction product was used for PCR analysis. First, an optimal number of PCR cycle was determined for each primer to give linear relationships between the amounts of the template cDNA and amplification products and PCR was carried out under such condition. The PCR products obtained were separated by a 7.5% polyacrylamide gel electrophoresis, stained with SYBR Green I (Molecular Probes), and the transcriptional level of each chicken clock gene was quantified with a FLA2000 bioimage analyzer (FUJI PHOTO FILM). Change in the transcriptional level of GAPDH, as a control, was measured in a similar manner as the above. Intensity of each signal was normalized to that of GAPDH, and the mean value for each gene on day 6 was set to 1. Then all the values (mRNA levels) were obtained from three different culture samples, which were shown by mean±SEM.

The primers and number of PCR cycles mentioned above were set up as follows. For cBmal1, cB1F1600 primer; 5'-TCCAGACATTTCTTCAGCTGG-3' (Seq. ID No. 39)

and cB1REND-primer; 5'-GGATGTTGAAGCAAGGTGC-3' (Seq. ID No. 40) were used and 23 cycles were practiced. For cBmal2, cB2F1270-primer; 5'-ACGAGTACTGCCAT-CAAGATG-3' (Seq. ID No. 41) and cB2REND-primer; 5'-GAGAGCCCATTGGATGTCAC-3' (Seq. ID No. 42) were used and 23 cycles were practiced. For cClock, cqCF862-primer; 5'-TTCTTGGATCACAGGGCAC-3' (Seq. ID No. 43) and cqCR1364-primer; 5'-GGAGT-GCTAGTGTCCACTGTCA-3' (Seq. ID No. 44) were used and 25 cycles were practiced. For cPer2, cP2RTF primer; 5'-GGAAGTCCTTGCAGTGCATAC-3' (Seq. ID No. 45) and cP2RTR-primer; 5'-ACAGGAAGCGGATATGCAG-3' (Seq. ID No. 46) were used and 24 cycles were practiced. For GAPDH (GenBank accession no. K01458), cGAF-primer; 5'-ACCACTGTCCATGCCATCAC-3' (Seq. ID No. 47) and cGAR-primer; 5'-TCCACAACACGGTTGCT-GTA-3' (Seq. ID No. 48) were used and 15 cycles were practiced. Taq-Gold was used as polymerase. The program of PCR thermal cycler for each clock gene was as follows: degeneration for 9 min at 95° C. only for the first time; followed by repetitive cycles each consisting of thermal degeneration for 15 sec at 94° C., annealing for 30 sec at 55° C. and extension for 30 sec at 72° C.; and finally the extension reaction for 7 min at 72° C.

FIG. 11 shows the results of the above. It was confirmed by the result that all four kinds of transcripts that were expressed in the chick pineal cells displayed daily fluctuations in abundance with diverged phases and amplitudes in LD cycles and under DD condition. The fluctuation profiles in vivo in Example 3 (FIG. 10) are very similar to those in vitro in Example 4 (FIG. 11), where the cPer2 mRNA levels had a peak early in the morning and a trough early at night. This result was similar to the fluctuation profile of mPer1 in the mouse SCN (Cell 90, 1003–1011, 1997, Nature 389, 512–516, 1997). A high level expression of cPer2 sustained at the early light phase (Zeitgeber time (ZT) 2–6) under LD condition, as compared with a rapid decline in cPer2 expression at circadian time (CT) 2–6 under DD condition, indicated that the pineal photoreception plays a role in keeping the high level expression of cPer2 in the morning. The mRNA levels of cBmal1 and cBmal2 also exhibited clear oscillations and their phases were opposite to that of cPer2 (FIG. 11). Peak time in the cBmal2 mRNA level was delayed by about 4 hr compared to that in the in vitro cBmal1 mRNA level. This tendency was also observed in the in vivo fluctuation profile. In contrast, the cClock mRNA level showed a relatively low amplitude with a broad peak at ZT 10–18 or CT 10–18, and the peak seems to cover the peaks in expression levels of the two Bmal genes. A similar oscillation of cClock mRNA is observed in the chicken retina (Mol. Brain Res. 70, 253–263, 1999).

EXAMPLE 5

Expression of the Mouse Clock Genes in the Suprachiasmatic Nuclei mRNA levels of mBmal2 and known clock genes (mPer2, mClock and mBmal1) of the mouse suprachiasmatic nuclei under LD cycles were studied as follows. 5-week-old male C57BL/6 mice were subjected to LD cycles at 23° C.±1° C. (about 200 lux of bright cycle under a fluorescent lamp) and bred with free access to feed and water. 3 weeks thereafter, the mice were decapitated and the brains were rapidly isolated, frozen, and sectioned into thin strips with 700 μm thickness. Small tissue sections including SCN on both sides were taken out from the sections by using a 20-gauge needle, and the mRNA expression levels in mBmal2, mPer2, mClock, mBmal1, etc. in the tissue sections were quantified by a quantitative RT-PCR. Three independent RNA samples prepared from six mice (n=3) were respectively quantified and each signal intensity thus obtained was normalized to the signals for mGAPDH and the mean of the three values (mean±SEM) were calculated. p values in FIG. 12 were determined by using Student's t test.

The above-mentioned primers and number of PCR cycle were determined to give linear relationships between the amounts of the template cDNA and amplification products. For mBmal2, mBMAL2-F2 primer; 5'-TGGTTGGATGC-GAAAGAGG-3' (Seq. ID No. 49) and mBMAL2-R4 primer; 5'-AGGTTTCTCTCTTGGTGAACC-3' (Seq. ID No. 50) were used and 28 cycles were practiced. For mBmal1 (GenBank accession no. AB012600), rmBmal1-F1 primer; 5'-TGGTACCAACATGCAATGC-3' (Seq. ID No. 51) and rmBmal1-R1 primer; 5'-AGTGTCCGAGGAA-GATAGCTG-3' (Seq. ID No. 52) are used and 28 cycles were practiced. For mPer2 (GenBank accession no. AB016532), rmPer2-F1 primer; 5'-GCTCACTGCCA-GAACTATCTCC-3' (Seq. ID No. 53) and rmPer2-R1 primer; 5'-CCTCTAGCTGAAGCAGGTTAAG-3' (Seq. ID No. 54) are used and 30 cycles were practiced. For mClock (GenBank accession no. AB019258), rmClock-F1 primer; 5'-CAAGGTCAGCAACTTGTGACC-3' (Seq. ID No. 55) and rmClock-R1 primer; 5'-AGGATGAGCTGTGTC-GAAGG-3' (Seq. ID No. 56) were used and 28 cycles were practiced. For mGAPDH (GenBank accession no. X02231), rmGAPDH-F1 primer; 5'-CATCACCATCTTCCAGGAGC-3' (Seq. ID No. 57) and rmGAPDH-R1 primer; 5'-AT-TGAGAGCAATGCCAGCC-3' (Seq. ID No. 58) were used and 21 cycles were practiced. Programming for the PCR thermal cycler for each clock gene was carried out under the condition described in Example 4.

Figure 12:
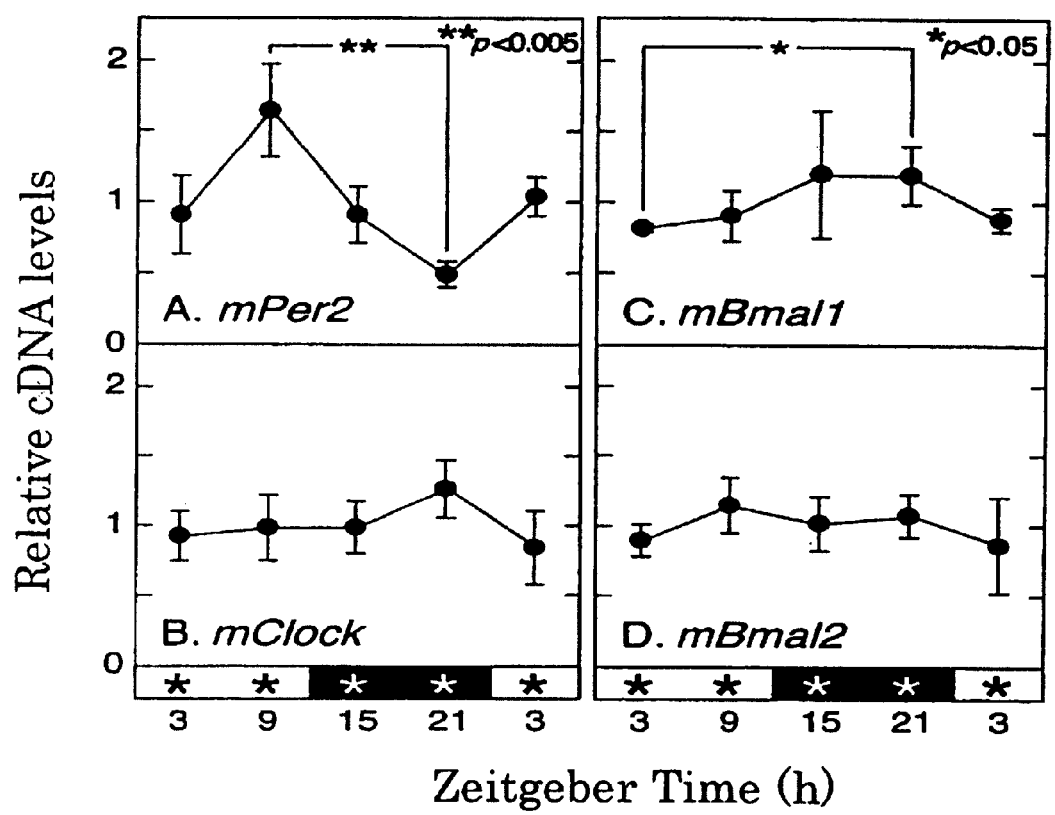
FIG. 12 shows the results of the daily fluctuations under LD condition in mRNA expressions of mPer2, mClock, mBmal1 and mBmal2 in the mouse suprachiasinatic nucleus.

The results of the above are shown in FIG. 12. In these results, the mPer2 mRNA level displayed daily fluctuations in abundance in the SCN region (FIG. 12A) as are reported in the literatures (Genes Cell 3, 167–176, 1998, Science 288, 1013–1019, 2000). Besides, the mBmal1 mRNA level showeda faint oscillation in almost antipahse to mPer2 which is in LD cycles (FIG. 12C). On the contrary, mRNA level of mBmal2 was almost constant all day long which was similar to the case of mClock (FIG. 12B, D), suggesting the difference in transcriptional regulation between mBmal1 and mBmal2 genes.

EXAMPLE 6

Changes in the Photo-Dependency of mRNA Levels in cPer2, cBmal1 and cBmal2 in the Chick Pineal Glands Since the expression level of cBmal1/2 in the early morning was low (FIG. 12), a possible light-dependent down-regulation of cBmal1/2 transcriptions was tested. Chicks were exposed to light for a time period when both cBmal1/2 expression levels were high in the dark (CT14-CT15), as is seen from the results of Example 4, and changes in mRNA levels were evaluated at CT15.5 and CT17. One-day-old chicks were entrained to LD cycle for a week and then placed in DD condition. The chick pineal glands that were exposed to a 1-hr light-pulse (350 lux) (CT14–CT15) on the first day of DD condition (FIG. 13A, below) and the chick pineal glands without exposure to light-pulse (FIG. 13A, top) were respectively isolated at CT15.5 or CT17 and the total RNA (8 μg) obtained from each of the pineal glands were respectively separated by an agarose gel electrophoresis and blotted onto a nitrocellulose membrane.

Figure 13:
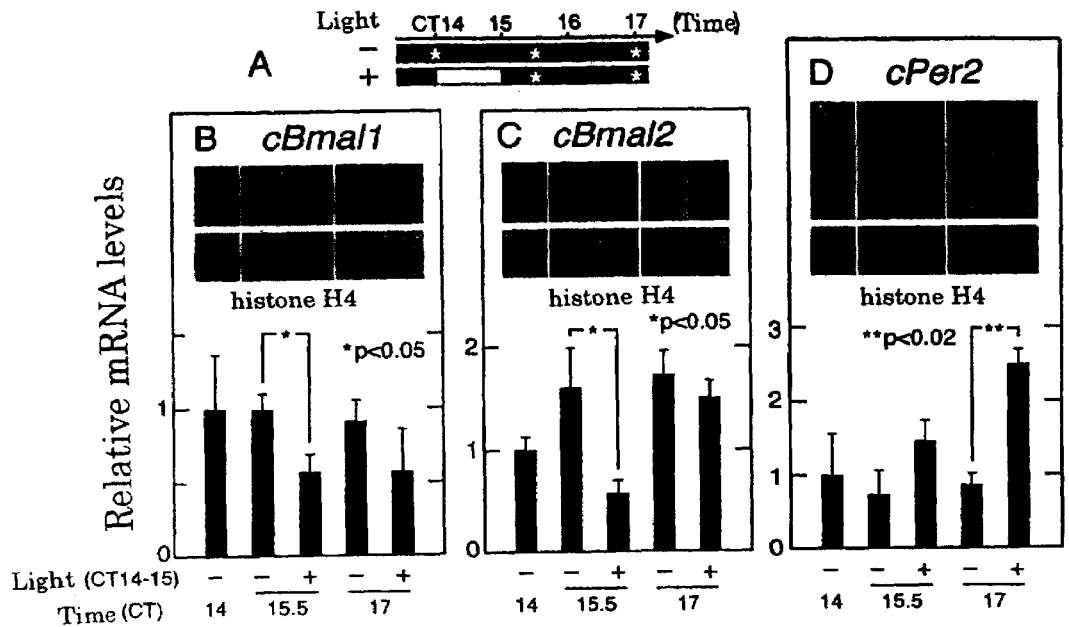
FIG. 13 shows the results of light-dependent changes in mRNA expressions of cPer2, cBmal1 and cBmal2 in the chicken pineal glands.

Each blotting membrane as aforementioned was cut into two pieces and one (containing RNA longer than 2.4 Kb) was hybridized with a cBmal1, cBmal2 or cPer2 probe and another with a histone H4 probe. Then the signals for cBmal1 (FIG. 13B), cBmal2 (FIG. 13C), cPer2 (FIG. 13D) and histone H4 were quantified by MacBAS software (FUJI PHOTO FILM) and the intensity of all the signals were normalized to those for histone H4. The mean value of each gene at CT14 was set to 1 and the mRNA levels were determined. The values were determined from triplicate experiments practiced in a similar way as in the above and shown as mean±SEM. FIG. 13 shows the results. In FIG. 13, "an asterisk" and "double asterisks" mean p <0.05 and p <0.02, respectively. p values were determined using Student's t test. These results demonstrate that mRNA levels of cBmal1 and cBmal2 observed in the pineal glands of chicks exposed to light at CT15.5 were substantially lower than those of the control animals without exposure to light. On the contrary, the light-induced cPer2 expression was confirmed at CT17, two hours after the exposure to light, as was observed for mPer1 and mPer2 in the SCN of the mice exposed to light (Cell 91, 1055–1064, 1997, Neuron 19, 1261–1269, 1997, Genes Cells 3, 167–176, 1998).

EXAMPLE 7

Functional Property of cBMAL2; Pull-Down Assay

A close kinship between BMAL1 and BMAL2 among ARNT-(aryl hydrocarbon receptor nuclear translocator) related proteins (FIG. 5) seems to indicate their functional similarity. Therefore, relationships among cBMAL1, cBMAL2 and cCLOCK were tested by a glutathione-S-transferase (GST) pull-down assay using three kinds of bacterially expressed GST-fusion proteins [GST-cCLOCKΔ (a fusion of GST and $Met^1$-$Ser^{466}$cCLOCK truncated at the carboxy-terminal region), GST-cBMAL1 and GST-cBMAL2], together with [$^{35}$S]-labeled cBMAL1Δ ($Met^1$-$Ser^{449}$) or [$^{35}$S]-labeled cBMAL2Δ ($Met^1$-$Leu^{458}$) that were transcribed and translated in vitro. Because GST-cCLOCK (a fusion protein composed of GST and the full-length cCLOCK) was not solubilized by 2% Triton X-100, GST-cCLOCKΔ mentioned above was used instead.

A DNA fragment encoding GST-cCLOCKΔ, GST-BMAL1, GST-BMAL2 or GST, mentioned above, was introduced into a pGEX5X-1 expression vector and expressed in BL21 E. coli strain. Each E. coli was subjected to lysis in buffer A [10 mM Na-phosphate (pH 7.9), 140 mM NaCl, 1 mM $MgCl_2$, 10 mM EDTA, 5 mM 2-mercaptoethanol, 2 mM PMSF and one tablet of Complete EDTA-free protease inhibitor (Roche Diagnostics) per 50 mL], then each of solubilized fusion proteins or GST was purified by glutathione-Sepharose column (Amersham Pharmacia Biotech). On the other hand, [$^{35}$S]-labeled cBMAL1Δ ($Met^1$-$Ser^{449}$) and [$^{35}$S]-labeled cBMAL2Δ ($Met^1$-$Leu^{458}$) mentioned above were prepared by the in vitro transcription and translation of an expression plasmid containing cDNA fragment of cBMAL1Δ ($Met^1$-$Ser^{449}$) or cBMAL2Δ ($Met^1$-$Leu^{458}$) in the presence of [$^{35}$S] methionine and with the aid of TNT-T7 Quick Coupled Transcription/Translation System (Promega). [$^{35}$S]-labeled luciferase as a control was similarly transcribed and translated in vitro.

8 μL each of the [$^{35}$S]-labeled protein (cBMAL1Δ, cBMAL2Δ or luciferase protein) solutions was mixed with 40 μL of glutathione-sepharose beads, to which GST-cCLOCKA (0.1 μg), GST-cBMAL1 (1.1 μg), GST-cBMAL2 (3.3 μg) or GST (5.6 μg) had been bound. Then the mixtures were incubated in 140 μL of buffer B [20 mM Hepes-NaOH (pH 7.9), 20% (w/v) glycerol, 15 mM KCl, 0.2% Triton X-100, 2.5% skim milk, one tablet of Complete EDTA-free protease inhibitor per 50 mL] on ice for 1 hr with gentle rotation. After the incubation the mixtures were washed four times with buffer C [10 mM Tris-HCl (pH 7.5), 0.2% Triton X-100, 150 mM NaCl, 2 mM EDTA, 1 mM PMSF, one tablet of Complete EDTA-free protease inhibitor] and were separated by a SDS-polyacrylamide (10%) gel electrophoresis, then the gel was analyzed for autoradiograph by using a FLA2000 bioimage analyzer (FUJI PHOTO FILM).

Figure 14:
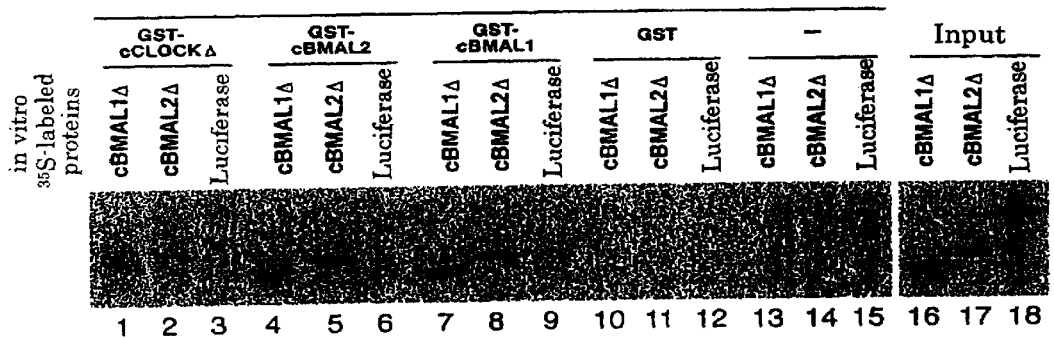
FIG. 14 shows the results of the in vitro physical interactions among cBMAL2 of the present invention, cBMAL1 and cCLOCK proteins.

The results of the above are shown in FIG. 14. Lanes 16–18 is the results of electrophoresis for [$^{35}$S]-labeled cBMAL1Δ, cBMAL2Δ or luciferase (2.5% each of the inputs). A faint signal observed in lane 17 (the upper band) is due to the migration of luciferase from lane 18. These results revealed that GST-cCLOCKΔ specifically bound not only with cBMAL1Δ but also with cBMAL2Δ in vitro (FIG. 14, lanes 1, 2). Interestingly, GST-cBMAL2 bound with both cBMAL proteins (FIG. 14, lanes 4, 5), and GST-cBMAL1 also showed similar binding profiles (FIG. 14, lanes 7, 8), indicating potential activity of cBMAL proteins to form a homodimer as well as a cBMAL1-cBMAL2 heterodimer. It was also demonstrated that a CBMAL protein deficient in the C-terminal bound more efficiently with a GST-fusion protein than with a full-length CBMAL protein.

EXAMPLE 8 an Electrophoretic Mobility Shift Assay Using a cPer2 E-box-Containing Probe

A binding of cBMAL1-cCLOCK or cBMAL2-cCLOCK to the E-box sequence was examined by an electrophoretic mobility shift assay (EMSA) in which an E-box (CACGTG)-containing sequence present in a promoter region of cPer2 gene was used as a probe. For preparation of the probe, oligonucleotides [cP2E1-S: 5'-GTGTCA-CACGTGAGGCTTA-3' (Seq. ID No. 59) and cP2E1-AS: 5'-TAAGCCTCACGTGTGACAC-3' (Seq. ID No. 60)] were synthesized that correspond to the E-box sequence and its flanking sequences within a putative promoter/enhancer region of cPer2 gene. These oligonucleotides synthesized were annealed together and subcloned into a pCR2.1 vector using TOPO-TA cloning kit (Invitrogen, Calif.), from which a 39 bp fragment was excised with a restriction enzyme EcoRI and used. The above-mentioned cBMAL1, cBMAL2 and cCLOCK were prepared by being transcribed and translated in vitro from an expression plasmid containing the cDNA of cBmal1, cBmal2 or cClock with the aid of TNT-T7 Quick Coupled Transcription/Translation System (Promega). A pcDNA3.1/V5/His empty vector, an expression vector, alone was transcribed and translated similarly as in the above and used as a control.

Figure 15:
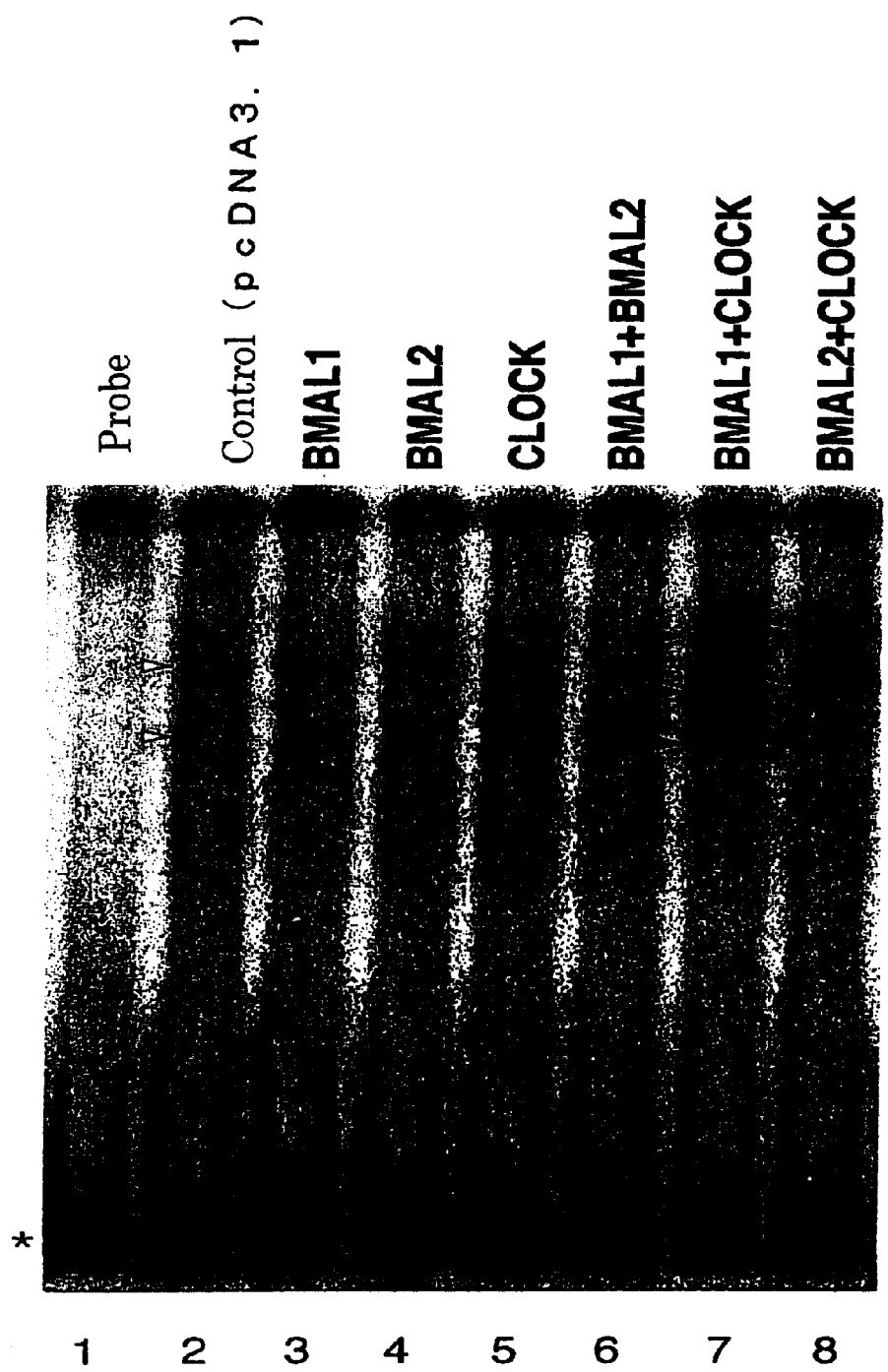
FIG. 15 shows the results of the binding between a E-box sequence and cBMAL1-cCLOCK or cBMAL2-cCLOCK detected by an electrophoretic mobility shift assay (EMSA).

5 μL each of the protein mixtures thus obtained (BMAL1+BMAL2, BMAL1+CLOCK, BMAL2+CLOCK) was added with 32 μL of buffer [25 mM Hepes-KOH (pH 7.6), 100 mM KCl, 0.1 mM EDTA, 10% (v/v) glycerol, 7.5 mM $MgCl_2$, 1 mM DTT and 1 μg denatured salmon sperm DNA] containing a $^{32}$P-labeled probe (33 fmoles, 1.3×10$^5$ cpm) andwas incubated for 20 min at 23° C. After the incubation, each mixture was separated by a 6% polyacrylamide gel electrophoresis and analyzed similarly as in Example 7 using a FLA2000 bioimage analyzer (FUJI PHOTO FILM). FIG. 15 shows the results. In FIG. 15, lane 1 is the result of the labeled probe alone, lanes 2–5 are the results of the reactions between each translation product (control, BMAL1, BMAL2 or CLOCK) and the labeled probe. In the figure, the asterisk denotes the position of the free probe, closed arrowheads represent specific complexes with the bHLH-PAS proteins, and open arrowheads indicate background. It was confirmed from these results that in the presence of cCLOCK, cBMAL2 and cBMAL1 had respectively formed two or three complexes (closed arrowheads in lanes 7 and 8 in FIG. 15). It is unlikely that these complexes represent homodimers of any of the PAS proteins examined (cCLOCK, cBMAL1 or cBMAL2), because no specific bands were observed when cCLOCK, cBMAL1 or cBMAL2 alone was reacted with the probe (lanes 3–6 in FIG. 15). These results suggest that the cPer2 E-box is one of the in vivo targets of cCLOCK-cBMAL1/2 heteromer.

EXAMPLE 9

Transcriptional Regulation by cBMAL1, cBMAL2 and cCLOCK in 293EBNA Cells

Abilities for the transcriptional activation and suppression of cBMAL1, cBMAL2 and cCLOCK were tested with the mPer2 E-box or the mPer1 promoter as a role model in the feed-back-loop and the vasopressin gene E-box as a role model in output pathways. Human embryonic kidney 293EBNA cells (Invitrogen) were cultured in Dulbecco's modified Eagle's medium supplemented with 10% fetal bovine serum (Life Technologies) which cultured cells were then plated at $3+10^5$ cells per well on six-well plates and transfected by using a total of 1.0 μg of various expression plasmids [an expression vector, plasmids containing reporter genes, 0.25 ng of Renilla luciferase reporter (pRL-CMV; Promega), and plasmids containing cDNA of each clock gene (cBmal1, cBmal2, cClock) with the amount indicated in FIG. 16] together with Lipofectamine plus (Life Technologies).

As for the expression vector mentioned above, pcDNA3.1/V5/His empty vector (Invitrogen) was used. As for the reporter genes mentioned above, 25 ng of the firefly luciferase reporter (cPer2 E-box-luc; a derivative of pGL3-Promoter; Promega) containing mPer2 E-box, 25 ng of cPer2 mut.E-box-luc, 50 ng of the firefly luciferase reporter containing mPer1 promoter (mPer1-luc; a derivative of pGL3-Basic; Promega) 25 ng of the firefly luciferase reporter containing the mouse vasopressin E-box (AVP E-box-luc; a derivative of pGL3-Promoter; Promega), 25 ng of AVP mut. E-box-luc, or 25 ng of TRE-luc were used. Two days after the transfection, cell extracts were subjected to dual-luciferase assays by luminometry (Promega) according to the manufacturer's protocol. For each extract, the firefly luciferase activity was normalized by the Renilla luciferase activity and the mean value (means±SEM) was determined from the values of three independent culture extracts.

The aforementioned plasmids containing reporter genes were prepared as follows. The E-box sequence, CACGTG and its flanking sequences within the promoter/enhancer region of cPer2 gene were linked in tandem (5'-GTGTCA-CACGTGAGGCTTAGTGTCACACGTGAG-GCTTAGTGTCACACGTGAGGCTTA-3'), which was then inserted into a luciferase reporter containing SV-40 (pGL3-Promoter, Promega) and thus the cPer2 E-box-luc was constructed. The cPer2 mut.E-box as a reporter plasmid in the control experiment was constructed by mutating the E-box sequences into GGACCT in a similar way as previously reported (Cell 96, 57–68, 1999). mper1-luc was constructed as follows; a 2.2 Kb upstream fragment of mPer1 was amplified by PCR using the DNA templates from the mouse genome [sense primer 3; 5'-TCGAGCTCTTTGG-TACCTGGCCAGCAACC-3' (Seq. ID No. 61) and anti-senseprimer3; 5'-TCACGACACCTGGCCGTTCGAGG-3' (Seq. IDNo. 62)] and LA-Taq polymerase, base sequences for the six clones individually obtained by PCR were determined, and then one clone without PCR error among the six clones was linked to a luciferase reporter (pGL3-Basic, Promega). AVP E-box-luc was constructed by linking E-box sequence (CACGTG) in the promoter/enhancer region in the mouse vasopressin gene and its flanking sequences, and then by inserting the resulting sequence (5'-TCAGGCCCACGTGTCCCA-3') into the luciferase reporter containing SV-40 promoter (pGL3-Promoter, Promega). Further, the AVP mut. E-box-luc (a reporter with a E-box mutation) which is a reporter plasmid for the control experiment was prepared in a way previously described (Cell 96, 57–68, 1999). TRE-luc was prepared as follows; the phorbol ester-responsive element (TRE) and its flanking sequences within human collagenase gene were linked in tandem [5'-CGGCTGACTCATCAAGCTGACTCAT-CAAGCTGACTCATCAA-3' (Seq. ID No. 63)], which was then inserted into the BglII site in a luciferase reporter in which a BglII-HindIII fragment of pRL-TK vector (Promega) was ligated to a pGL3-Basic vector (pGL3-TK-promoter vector).

Figure 16:
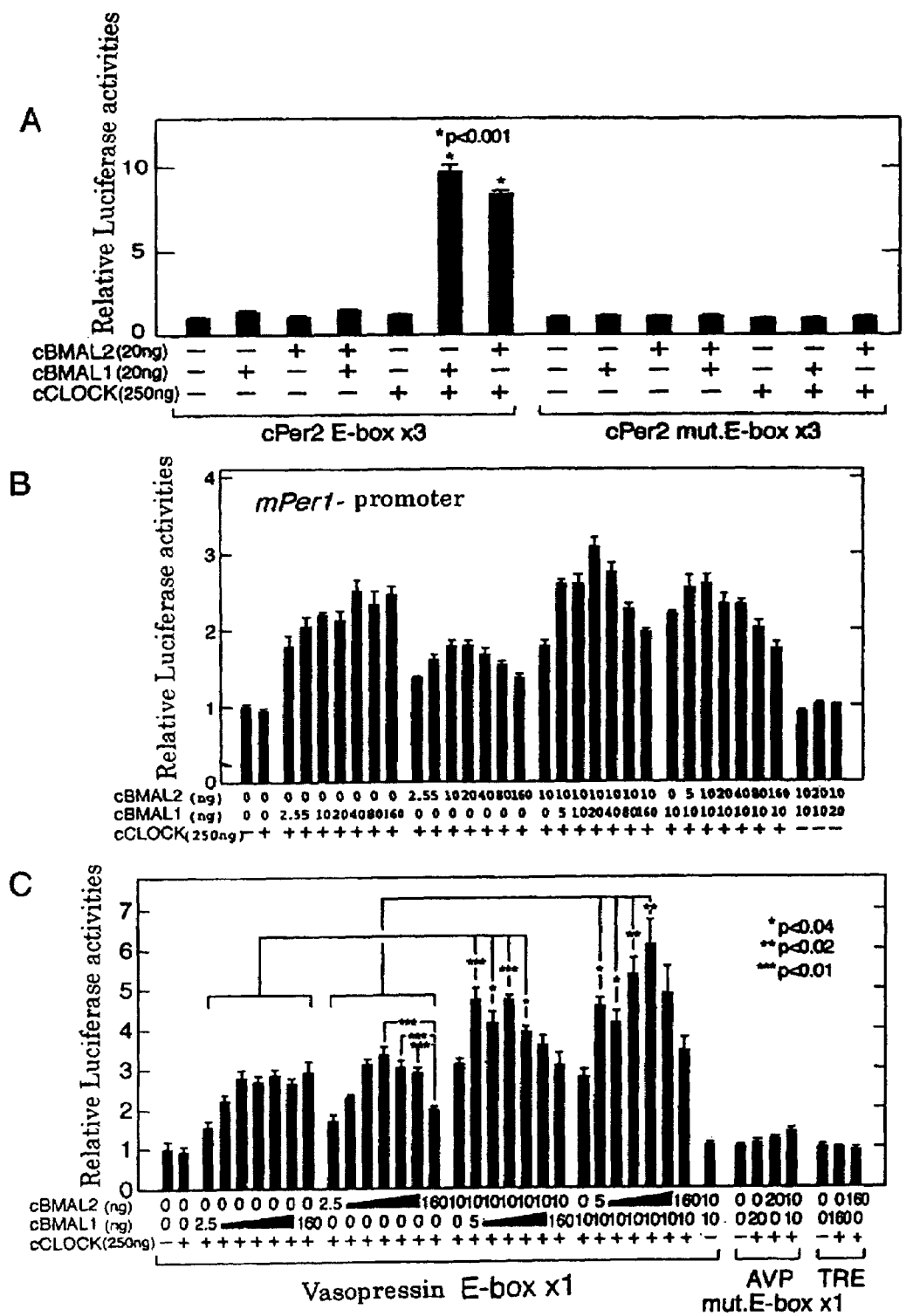
FIG. 16 shows the results of transcriptional regulation in the 293EBNA cells induced by cBMAL1, cBMAL2 and cCLOCK.

These results are shown in FIG. 16. The results show that cCLOCK binds to not only cBMAL1 but cBMAL2 and promotes the transactivation which is medidted by the cPer2 E-box (FIG. 16A). Similar results were obtained by using a 2.2-kb mPer1 promoter harboring three E-box sequences (CACGTG) (FIG. 16B). Interestingly, the transactivation elicited by cBMAL2-cCLOCK showed a clear peak when a relatively low dose (20 ng) of a cBmal2 expression plasmid and cClock plasmid (250 ng) were coexpressed, and a higher dose than the above of cBmal2 plasmid suppressed the transactivation in FIG. 16B (see the left of the figure) and FIG. 16C (see 10th–16th bars from the left of the figure). cBmal1, however, seems to have no such inhibitory effect. Endogenous transactivation neither from the TPA-responsive element (TRE, FIG. 16B) nor from the SV40-promoter was suppressed by application of a high dose (160 ng) of cBmal2, which fact suggests that the suppression is due to the specific effect on E-box or E-box-binding component(s).

Since cBmal1 and cBmal2 had the slightly shifted expression profiles as can be seen in FIGS. 10 and 11, a cooperative effect of cBMAL1 and cBMAL2 on the transcriptional regulation was tested. In the case of a vasopressin gene E-box as a reporter (FIG. 16C), a low level expression (10ng) of cBmal2 notably enhanced cBMAL1-cCLOCK transactivation (see 17th–23rd bars from the left in FIG. 16C). A similar or more pronounced cooperative effect was observed with a low dose of cBmal1 plasmid (10 ng) for cBMAL2-cCLOCK transactivation (see 24th–30th bars from the left in FIG. 16C). Besides, the cooperative activation was considerably suppressed by the application of larger amounts of cBmal2 (80–160 ng) or cBmal1 (40–160 ng). Similar results were also observed in the cases when a cPer2 E-box or a mPer1 promoter was used, albeit with less degrees (FIG. 16B).

EXAMPLE 10

Effect of cPER2 on Transactivation Mediated by E-box Sequences

Figure 17:
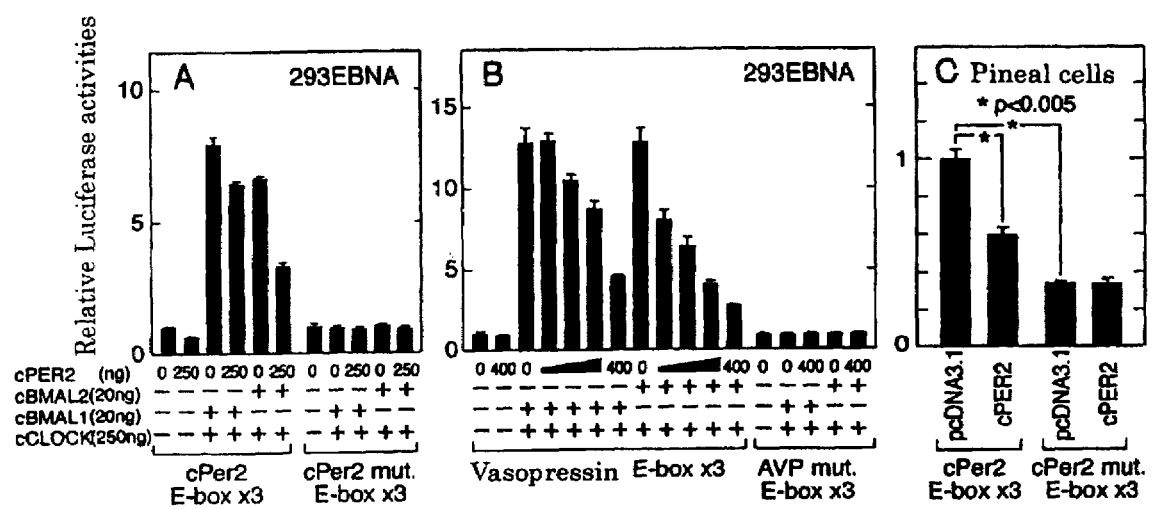
FIG. 17 shows the cPER2 effect on transactivation mediated by E-box sequences.

Next, whether cPER2 negatively acted on the transactivation elicited by the transactivator cBMAL-cCLOCK was examined. The experiment described in this Example 10 was performed in a similar way as in Example 9 except that plasmids containing a cPer2 cDNA were transfected, with the amounts shown in FIGS. 17A and 17B, to the expression plasmids which were to be transfected to the human embryonic kidney293EBNA cells. The results are shown in FIGS. 17A and 17B. The results show that coexpression of cPer2 plasmid (250 ng) in 293EBNA cells inhibited the cBMAL2-cCLOCK-dependent transactivation mediated by cPer2 E-box, and the degree of the inhibitory effect was stronger than that on cBMAL1-cCLOCK-dependent transactivation under the same conditions (FIG. 17A). Similar tendency was also observed in the case of cBMAL-cCLOCK-dependent transactivation mediated by the vasopressin E-box (FIG. 17B), and the higher degree of inhibitory effect was observed with the increase in the cPER2 amount.

Then, intrinsic properties of the cPer2 E-box mediated transactivation were studied in the cultured chick pineal cells. The pineal cells prepared from one-day-old chicks were plated at $4 \times 10^5$ cells per well on 24-well plates and cultured under LD cycle. At ZT9 on Day 3 of the culture, the pineal cells were transfected with 500 ng of either the aforementioned cPer2 expression plasmid or pcDNA3.1/V5/His (control), 250 ng of either the cPer2 E-box-luc or the cPer2 mut.E-box-luc, and 5 ng of pRL-CMV (Promega) by using Lipofectamine plus. At ZT6 on the next day of the transfection, the cell extracts were subjected to a dual-luciferase assay and the results are shown in FIG. 17C. The results demonstrated that the endogenous transactivation mediated by cPer2 E-box was markedly decreased as a result of mutating the E-box sequence and that the inhibitory effect on transactivation induced by forced expression of cPER2 was also E-box-dependent. These facts suggest that the chicken pineal cells express a positive factor acting on the cPer2 E-box and that this factor exhibits an effect on the negative regulation by cPER2.

EXAMPLE 11

Figure 18:
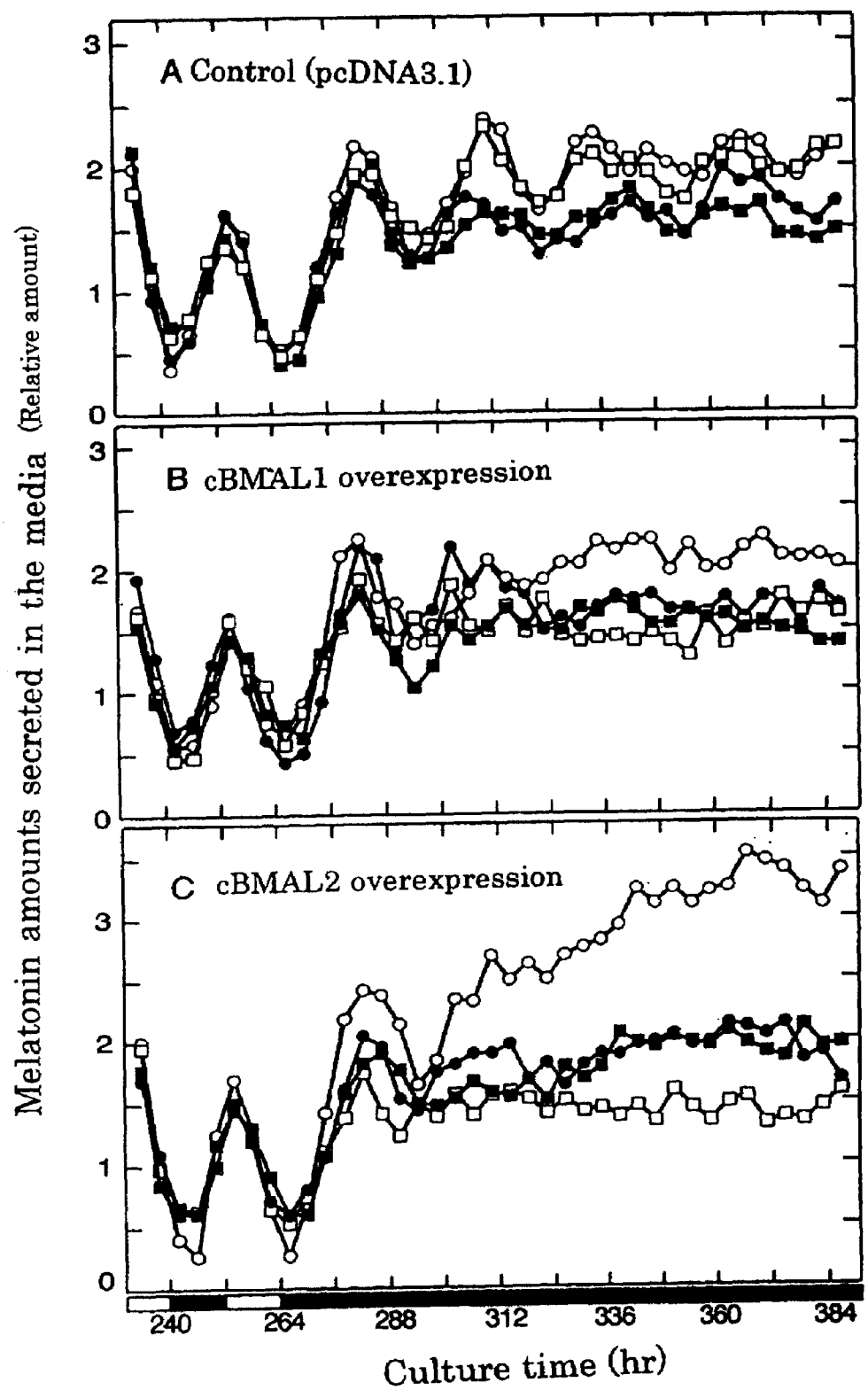
FIG. 18 shows the effect of overexpression of cBMAL1 or cBMAL2 on the melatonin-rhythms of the chicken pineal cells.

Ablation of Melatonin Rhythm by the Overexpression of cBMAL1 and cBMAL2 cBMAL1 or cBMAL2 was overexpressed in the cultured chick pineal cells and its effect on the melatonin rhythm was examined to evaluate the roles of the two PAS proteins in maintenance of the rhythmicity. The chick pineal cells were cultured in 24-well cloning plates (Greiner Labortechnik, Frickenhausen, Germany) for 2 days and transfected with 500 ng of either cBMAL1 or cBMAL2 expression plasmid mentioned above or pcDNA3. 1/V5/His (control) by using a combination of Lipofectamine plus (Life Technologies) and Genefector (VennNova LLc, FL). 2 days after the transfection, the cells were subjected to a 4-day culture in the media containing 200 mg/L G418 (Life Technologies) to select the transfected cells and the cells selected were further cultured in the media containing 50 mg/L G418. The culture media were collected every 4 hours to quantify the released melatonin by the previously described method (Neurosci 20, 986–991, 2000). FIG. 18 shows the results. Four data in each panel are the results obtained from the individual cultures where each value was determined by setting the average of melatonin production levels during the LD cycles to 1. The bar at the bottom of FIG. 18 represents lighting conditions.

A slight phase-delaying was observed upon studying the melatonin rhythm in the pineal gland of each cell. This change was also observed in the untransfected pineal cells, and such clock oscillation was also observed after culturing control cells (FIG. 9A) and cells overexpressing proteins unrelated to clock proteins such as a m1 or m2 acetylcholine receptor, under DD condition for several days. In contrast to these control cells, cBMAL1- or cBMAL2-overexpressing cells displayed only a single oscillation in melatonin production under DD condition, which was thereafter kept at a constant level (FIGS. 18B and 18C). Under the LD cycles, daily melatonin fluctuations in cBMAL1- or cBMAL2-overexpressing cells were quite similar to those of control cells, indicating that cellular mechanisms for light-dependent melatonin production were stably maintained by the overexpressed cBMAL proteins. In spite of this, the ablation of rhythm under DD condition strongly suggests that cBMAL1 and cBMAL2 are both indispensable factors for rhythmic oscillation.

INDUSTRIAL APPLICABILITY

The present invention makes it possible to provide novel clock proteins having the novel BMAL2 activity crucial for the clock oscillation mechanism including photic-input pathway and output pathway, and the gene DNAs encoding the proteins. Further, with the use of these proteins and the gene DNAs, substances useful for prevention and therapy of the circadian rhythm sleep disorders or the like including delayed sleep phase syndrome, non-24-hour sleep-wake syndrome, advanced sleep phase syndrome, time zone change syndrome, shift work sleep disorder, etc. can be screened, in addition to which a molecular mechanism of the circadian oscillation system can also be elucidated. Still further, the proteins of the present invention having the BMAL2 activity have functions both for promoting and suppressing transcription and are thought to be involved in diverse biological functions by binding with partners other than CLOCK. The proteins are therefore expected to be applied to specifically inhibit a group of functions in the transcriptional regulatory regions including that of period genes by gene-introduction of BMAL2 or the BMAL2-dominant negative mutants in an excessive amount from the outside.

The invention claimed is:

1. DNA encoding a protein comprising an amino acid sequence shown by Seq. ID No. 10.

2. DNA containing a base sequence shown by Seq. ID No. 9 or its complementary sequence.

3. DNA which hybridizes with DNA of claim 2 under a stringent condition comprising hybridization at 65° C. and washing at 65° C. in a buffer solution containing 0.1 X SSC, 0.1% SDS, and which encodes a protein having the BMAL2 activity.

4. A host cell comprising an expression system capable of expressing a protein encoded by DNA according to any one of claims 1–3.

5. The host cell according to claim 4, wherein the host cell is further capable of expressing CLOCK and/or BMAL1.

6. The host cell according to claim 4, wherein the expression system at least comprises a promoter having an E-box sequence (CACGTG).

7. The host cell according to claim 6, wherein the promoter having an E-box sequence (CACGTG) is a promoter of Per gene, Tim gene, Cry gene, vasopressin gene or the albumin D-site binding protein gene.

* * * * *

SEQUENCE LISTING

<160> NUMBER OF SEQ ID NOS: 63

<210> SEQ ID NO 1
<211> LENGTH: 1930

```
<212> TYPE: DNA
<213> ORGANISM: Homo sapiens
<220> FEATURE:
<221> NAME/KEY: CDS
<222> LOCATION: (19)..(1926)

<400> SEQUENCE: 1
```

| | | | | | | | | | | | | |
|---|---|---|---|---|---|---|---|---|---|---|---|---|
| gaccaagtgg ctcctgcg | atg<br>Met<br>1 | gcg<br>Ala | gcg<br>Ala | gaa<br>Glu | gag<br>Glu<br>5 | gag<br>Glu | gct<br>Ala | gcg<br>Ala | gcg<br>Ala | gga<br>Gly | ggt<br>Gly<br>10 | 51 |
| aaa<br>Lys | gtg<br>Val | ttg<br>Leu | aga<br>Arg<br>15 | gag<br>Glu | gag<br>Glu | aac<br>Asn | cag<br>Gln | tgc<br>Cys<br>20 | att<br>Ile | gct<br>Ala | cct<br>Pro | gtg<br>Val | gtt<br>Val<br>25 | tcc<br>Ser | agc<br>Ser | 99 |
| cgc<br>Arg | gtg<br>Val | agt<br>Ser<br>30 | cca<br>Pro | ggg<br>Gly | aca<br>Thr | aga<br>Arg | cca<br>Pro<br>35 | aca<br>Thr | gct<br>Ala | atg<br>Met | ggg<br>Gly | tct<br>Ser<br>40 | ttc<br>Phe | agc<br>Ser | tca<br>Ser | 147 |
| cac<br>His | atg<br>Met | aca<br>Thr<br>45 | gag<br>Glu | ttt<br>Phe | cca<br>Pro | cga<br>Arg | aaa<br>Lys<br>50 | cgc<br>Arg | aaa<br>Lys | gga<br>Gly | agt<br>Ser | gat<br>Asp<br>55 | tca<br>Ser | gac<br>Asp | cca<br>Pro | 195 |
| tcc<br>Ser<br>60 | cag<br>Gln | tca<br>Ser | gga<br>Gly | atc<br>Ile | atg<br>Met<br>65 | aca<br>Thr | gaa<br>Glu | aaa<br>Lys | gtg<br>Val | gtg<br>Val<br>70 | gaa<br>Glu | aag<br>Lys | ctt<br>Leu | tct<br>Ser | cag<br>Gln<br>75 | 243 |
| aat<br>Asn | ccc<br>Pro | ctt<br>Leu | acc<br>Thr<br>80 | tat<br>Tyr | ctt<br>Leu | ctt<br>Leu | tca<br>Ser | aca<br>Thr<br>85 | agg<br>Arg | ata<br>Ile | gaa<br>Glu | ata<br>Ile | tca<br>Ser<br>90 | gcc<br>Ala | tcc<br>Ser | 291 |
| agt<br>Ser | ggc<br>Gly | agc<br>Ser | aga<br>Arg<br>95 | gtg<br>Val | gaa<br>Glu | gat<br>Asp | ggt<br>Gly | gaa<br>Glu<br>100 | cac<br>His | caa<br>Gln | gtt<br>Val | aaa<br>Lys | atg<br>Met<br>105 | aag<br>Lys | gcc<br>Ala | 339 |
| ttc<br>Phe | aga<br>Arg | gaa<br>Glu<br>110 | gct<br>Ala | cat<br>His | agc<br>Ser | caa<br>Gln | act<br>Thr<br>115 | gaa<br>Glu | aag<br>Lys | cgg<br>Arg | agg<br>Arg | aga<br>Arg<br>120 | gat<br>Asp | aaa<br>Lys | atg<br>Met | 387 |
| aat<br>Asn | aac<br>Asn<br>125 | ctg<br>Leu | att<br>Ile | gaa<br>Glu | gaa<br>Glu | ctg<br>Leu<br>130 | tct<br>Ser | gca<br>Ala | atg<br>Met | atc<br>Ile | cct<br>Pro<br>135 | cag<br>Gln | tgc<br>Cys | aac<br>Asn | ccc<br>Pro | 435 |
| atg<br>Met<br>140 | gcg<br>Ala | cgt<br>Arg | aaa<br>Lys | ctg<br>Leu | gac<br>Asp<br>145 | aaa<br>Lys | ctt<br>Leu | aca<br>Thr | gtt<br>Val | tta<br>Leu<br>150 | aga<br>Arg | atg<br>Met | gct<br>Ala | gtt<br>Val | caa<br>Gln<br>155 | 483 |
| cac<br>His | ttg<br>Leu | aga<br>Arg | tct<br>Ser | tta<br>Leu<br>160 | aaa<br>Lys | ggc<br>Gly | ttg<br>Leu | aca<br>Thr | aat<br>Asn<br>165 | tct<br>Ser | tat<br>Tyr | gtg<br>Val | gga<br>Gly | agt<br>Ser<br>170 | aat<br>Asn | 531 |
| tat<br>Tyr | aga<br>Arg | cca<br>Pro | tca<br>Ser<br>175 | ttt<br>Phe | ctt<br>Leu | cag<br>Gln | gat<br>Asp | aat<br>Asn<br>180 | gag<br>Glu | ctc<br>Leu | aga<br>Arg | cat<br>His | tta<br>Leu<br>185 | atc<br>Ile | ctt<br>Leu | 579 |
| aag<br>Lys | act<br>Thr | gca<br>Ala<br>190 | gaa<br>Glu | ggc<br>Gly | ttc<br>Phe | tta<br>Leu | ttt<br>Phe<br>195 | gtt<br>Val | gtt<br>Val | gga<br>Gly | tgt<br>Cys | gaa<br>Glu<br>200 | aga<br>Arg | gga<br>Gly | aaa<br>Lys | 627 |
| att<br>Ile | ctc<br>Leu<br>205 | ttc<br>Phe | gtt<br>Val | tct<br>Ser | aag<br>Lys | tca<br>Ser<br>210 | gtc<br>Val | tcc<br>Ser | aaa<br>Lys | ata<br>Ile | ctt<br>Leu<br>215 | aat<br>Asn | tat<br>Tyr | gat<br>Asp | cag<br>Gln | 675 |
| gct<br>Ala<br>220 | agt<br>Ser | ttg<br>Leu | act<br>Thr | gga<br>Gly | caa<br>Gln<br>225 | agc<br>Ser | tta<br>Leu | ttt<br>Phe | gac<br>Asp | ttc<br>Phe<br>230 | tta<br>Leu | cat<br>His | cca<br>Pro | aaa<br>Lys | gat<br>Asp<br>235 | 723 |
| gtt<br>Val | gcc<br>Ala | aaa<br>Lys | gta<br>Val | aag<br>Lys<br>240 | gaa<br>Glu | caa<br>Gln | ctt<br>Leu | tct<br>Ser | tct<br>Ser<br>245 | ttt<br>Phe | gat<br>Asp | att<br>Ile | tca<br>Ser | cca<br>Pro<br>250 | aga<br>Arg | 771 |
| gaa<br>Glu | aag<br>Lys | cta<br>Leu | ata<br>Ile<br>255 | gat<br>Asp | gcc<br>Ala | aaa<br>Lys | act<br>Thr | ggt<br>Gly<br>260 | ttg<br>Leu | caa<br>Gln | gtt<br>Val | cac<br>His | agt<br>Ser<br>265 | aat<br>Asn | ctc<br>Leu | 819 |
| cac<br>His | gct<br>Ala | gga<br>Gly<br>270 | agg<br>Arg | aca<br>Thr | cgt<br>Arg | gtg<br>Val | tat<br>Tyr<br>275 | tct<br>Ser | ggc<br>Gly | tca<br>Ser | aga<br>Arg | cga<br>Arg<br>280 | tct<br>Ser | ttt<br>Phe | ttc<br>Phe | 867 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgt | cgg | ata | aag | agt | tgt | aaa | atc | tct | gtc | aaa | gaa | gag | cat | gga | tgc | 915  |
| Cys | Arg | Ile | Lys | Ser | Cys | Lys | Ile | Ser | Val | Lys | Glu | Glu | His | Gly | Cys |      |
|     | 285 |     |     |     | 290 |     |     |     |     | 295 |     |     |     |     |     |      |
| tta | ccc | aac | tca | aag | aag | aaa | gag | cac | aga | aaa | ttc | tat | act | atc | cat | 963  |
| Leu | Pro | Asn | Ser | Lys | Lys | Lys | Glu | His | Arg | Lys | Phe | Tyr | Thr | Ile | His |      |
| 300 |     |     |     |     | 305 |     |     |     |     | 310 |     |     |     |     | 315 |      |
| tgc | act | ggt | tac | ttg | aga | agc | tgg | cct | cca | aat | att | gtt | gga | atg | gaa | 1011 |
| Cys | Thr | Gly | Tyr | Leu | Arg | Ser | Trp | Pro | Pro | Asn | Ile | Val | Gly | Met | Glu |      |
|     |     |     | 320 |     |     |     |     | 325 |     |     |     |     | 330 |     |     |      |
| gaa | gaa | agg | aac | agt | aag | aaa | gac | aac | agt | aat | ttt | acc | tgc | ctt | gtg | 1059 |
| Glu | Glu | Arg | Asn | Ser | Lys | Lys | Asp | Asn | Ser | Asn | Phe | Thr | Cys | Leu | Val |      |
|     |     |     | 335 |     |     |     |     | 340 |     |     |     |     | 345 |     |     |      |
| gcc | att | gga | aga | tta | cag | cca | tat | att | gtt | cca | cag | aac | agt | gga | gag | 1107 |
| Ala | Ile | Gly | Arg | Leu | Gln | Pro | Tyr | Ile | Val | Pro | Gln | Asn | Ser | Gly | Glu |      |
|     |     |     | 350 |     |     |     |     | 355 |     |     |     |     | 360 |     |     |      |
| att | aat | gtg | aaa | cca | act | gaa | ttt | ata | acc | cgg | ttt | gca | gtg | aat | gga | 1155 |
| Ile | Asn | Val | Lys | Pro | Thr | Glu | Phe | Ile | Thr | Arg | Phe | Ala | Val | Asn | Gly |      |
|     | 365 |     |     |     |     | 370 |     |     |     |     | 375 |     |     |     |     |      |
| aaa | ttt | gtc | tat | gta | gat | caa | agg | gca | aca | gcg | att | tta | gga | tat | ctg | 1203 |
| Lys | Phe | Val | Tyr | Val | Asp | Gln | Arg | Ala | Thr | Ala | Ile | Leu | Gly | Tyr | Leu |      |
| 380 |     |     |     |     | 385 |     |     |     |     | 390 |     |     |     |     | 395 |      |
| cct | cag | gaa | ctt | ttg | gga | act | tct | tgt | tat | gaa | tat | ttt | cat | caa | gat | 1251 |
| Pro | Gln | Glu | Leu | Leu | Gly | Thr | Ser | Cys | Tyr | Glu | Tyr | Phe | His | Gln | Asp |      |
|     |     |     |     | 400 |     |     |     |     | 405 |     |     |     |     | 410 |     |      |
| gac | cac | aat | aat | ttg | act | gac | aag | cac | aaa | gca | gtt | cta | cag | agt | aag | 1299 |
| Asp | His | Asn | Asn | Leu | Thr | Asp | Lys | His | Lys | Ala | Val | Leu | Gln | Ser | Lys |      |
|     |     |     | 415 |     |     |     |     | 420 |     |     |     |     | 425 |     |     |      |
| gag | aaa | ata | ctt | aca | gat | tcc | tac | aaa | ttc | aga | gca | aaa | gat | ggc | tct | 1347 |
| Glu | Lys | Ile | Leu | Thr | Asp | Ser | Tyr | Lys | Phe | Arg | Ala | Lys | Asp | Gly | Ser |      |
|     |     |     | 430 |     |     |     |     | 435 |     |     |     |     | 440 |     |     |      |
| ttt | gta | act | tta | aaa | agc | caa | tgg | ttt | agt | ttc | aca | aat | cct | tgg | aca | 1395 |
| Phe | Val | Thr | Leu | Lys | Ser | Gln | Trp | Phe | Ser | Phe | Thr | Asn | Pro | Trp | Thr |      |
|     | 445 |     |     |     |     | 450 |     |     |     |     | 455 |     |     |     |     |      |
| aaa | gaa | ctg | gaa | tat | att | gta | tct | gtc | aac | act | tta | gtt | ttg | gga | cat | 1443 |
| Lys | Glu | Leu | Glu | Tyr | Ile | Val | Ser | Val | Asn | Thr | Leu | Val | Leu | Gly | His |      |
| 460 |     |     |     |     | 465 |     |     |     |     | 470 |     |     |     |     | 475 |      |
| agt | gag | cct | gga | gaa | gca | tca | ttt | tta | cct | tgt | agc | tct | caa | tca | tca | 1491 |
| Ser | Glu | Pro | Gly | Glu | Ala | Ser | Phe | Leu | Pro | Cys | Ser | Ser | Gln | Ser | Ser |      |
|     |     |     | 480 |     |     |     |     | 485 |     |     |     |     | 490 |     |     |      |
| gaa | gaa | tcc | tct | aga | cag | tcc | tgt | atg | agt | gta | cct | gga | atg | tct | act | 1539 |
| Glu | Glu | Ser | Ser | Arg | Gln | Ser | Cys | Met | Ser | Val | Pro | Gly | Met | Ser | Thr |      |
|     |     |     | 495 |     |     |     |     | 500 |     |     |     |     | 505 |     |     |      |
| gga | aca | gta | ctt | ggt | gct | ggt | agt | att | gga | aca | gat | att | gca | aat | gaa | 1587 |
| Gly | Thr | Val | Leu | Gly | Ala | Gly | Ser | Ile | Gly | Thr | Asp | Ile | Ala | Asn | Glu |      |
|     |     | 510 |     |     |     |     | 515 |     |     |     |     | 520 |     |     |     |      |
| att | ctg | gat | tta | cag | agg | tta | cag | tct | tct | tca | tac | ctt | gat | gat | tcg | 1635 |
| Ile | Leu | Asp | Leu | Gln | Arg | Leu | Gln | Ser | Ser | Ser | Tyr | Leu | Asp | Asp | Ser |      |
|     | 525 |     |     |     |     | 530 |     |     |     |     | 535 |     |     |     |     |      |
| agt | cca | aca | ggt | tta | atg | aaa | gat | act | cat | act | gta | aac | tgc | agg | agt | 1683 |
| Ser | Pro | Thr | Gly | Leu | Met | Lys | Asp | Thr | His | Thr | Val | Asn | Cys | Arg | Ser |      |
| 540 |     |     |     |     | 545 |     |     |     |     | 550 |     |     |     |     | 555 |      |
| atg | tca | aat | aag | gag | ttg | ttt | cca | cca | agt | cct | tct | gaa | atg | ggg | gag | 1731 |
| Met | Ser | Asn | Lys | Glu | Leu | Phe | Pro | Pro | Ser | Pro | Ser | Glu | Met | Gly | Glu |      |
|     |     |     | 560 |     |     |     |     | 565 |     |     |     |     | 570 |     |     |      |
| cta | gag | gct | acc | agg | caa | aac | cag | agt | act | gtt | gct | gtc | cac | agc | cat | 1779 |
| Leu | Glu | Ala | Thr | Arg | Gln | Asn | Gln | Ser | Thr | Val | Ala | Val | His | Ser | His |      |
|     |     |     | 575 |     |     |     |     | 580 |     |     |     |     | 585 |     |     |      |
| gag | cca | ctc | ctc | agt | gat | ggt | gca | cag | ttg | gat | ttc | gat | gcc | cta | tgt | 1827 |
| Glu | Pro | Leu | Leu | Ser | Asp | Gly | Ala | Gln | Leu | Asp | Phe | Asp | Ala | Leu | Cys |      |

```
                590                 595                 600
gac aat gat gac aca gcc atg gct gca ttt atg aat tac tta gaa gca    1875
Asp Asn Asp Asp Thr Ala Met Ala Ala Phe Met Asn Tyr Leu Glu Ala
        605                 610                 615 gag ggg ggc ctg gga gac cct ggg gac ttc agt gac atc cag tgg acc    1923
Glu Gly Gly Leu Gly Asp Pro Gly Asp Phe Ser Asp Ile Gln Trp Thr
620                 625                 630                 635 ctc tagc                                                           1930
Leu

<210> SEQ ID NO 2
<211> LENGTH: 636
<212> TYPE: PRT
<213> ORGANISM: Homo sapiens

<400> SEQUENCE: 2

Met Ala Ala Glu Glu Ala Ala Gly Gly Lys Val Leu Arg Glu
 1               5                  10                  15

Glu Asn Gln Cys Ile Ala Pro Val Val Ser Ser Arg Val Ser Pro Gly
                 20                  25                  30

Thr Arg Pro Thr Ala Met Gly Ser Phe Ser Ser His Met Thr Glu Phe
         35                  40                  45

Pro Arg Lys Arg Lys Gly Ser Asp Ser Asp Pro Ser Gln Ser Gly Ile
     50                  55                  60

Met Thr Glu Lys Val Val Glu Lys Leu Ser Gln Asn Pro Leu Thr Tyr
 65                  70                  75                  80

Leu Leu Ser Thr Arg Ile Glu Ile Ser Ala Ser Ser Gly Ser Arg Val
                 85                  90                  95

Glu Asp Gly Glu His Gln Val Lys Met Lys Ala Phe Arg Glu Ala His
             100                 105                 110

Ser Gln Thr Glu Lys Arg Arg Arg Asp Lys Met Asn Asn Leu Ile Glu
         115                 120                 125

Glu Leu Ser Ala Met Ile Pro Gln Cys Asn Pro Met Ala Arg Lys Leu
     130                 135                 140

Asp Lys Leu Thr Val Leu Arg Met Ala Val Gln His Leu Arg Ser Leu
145                 150                 155                 160

Lys Gly Leu Thr Asn Ser Tyr Val Gly Ser Asn Tyr Arg Pro Ser Phe
                 165                 170                 175

Leu Gln Asp Asn Glu Leu Arg His Leu Ile Leu Lys Thr Ala Glu Gly
             180                 185                 190

Phe Leu Phe Val Val Gly Cys Glu Arg Gly Lys Ile Leu Phe Val Ser
         195                 200                 205

Lys Ser Val Ser Lys Ile Leu Asn Tyr Asp Gln Ala Ser Leu Thr Gly
     210                 215                 220

Gln Ser Leu Phe Asp Phe Leu His Pro Lys Asp Val Ala Lys Val Lys
225                 230                 235                 240

Glu Gln Leu Ser Ser Phe Asp Ile Ser Pro Arg Glu Lys Leu Ile Asp
                 245                 250                 255

Ala Lys Thr Gly Leu Gln Val His Ser Asn Leu His Ala Gly Arg Thr
             260                 265                 270

Arg Val Tyr Ser Gly Ser Arg Arg Ser Phe Phe Cys Arg Ile Lys Ser
         275                 280                 285

Cys Lys Ile Ser Val Lys Glu Glu His Gly Cys Leu Pro Asn Ser Lys
     290                 295                 300

Lys Lys Glu His Arg Lys Phe Tyr Thr Ile His Cys Thr Gly Tyr Leu
```

```
                305                 310                 315                 320
Arg Ser Trp Pro Pro Asn Ile Val Gly Met Glu Glu Arg Asn Ser
                325                 330                 335
Lys Lys Asp Asn Ser Asn Phe Thr Cys Leu Val Ala Ile Gly Arg Leu
                340                 345                 350
Gln Pro Tyr Ile Val Pro Gln Asn Ser Gly Glu Ile Asn Val Lys Pro
                355                 360                 365
Thr Glu Phe Ile Thr Arg Phe Ala Val Asn Gly Lys Phe Val Tyr Val
                370                 375                 380
Asp Gln Arg Ala Thr Ala Ile Leu Gly Tyr Leu Pro Gln Glu Leu Leu
385                 390                 395                 400
Gly Thr Ser Cys Tyr Glu Tyr Phe His Gln Asp Asp Asn Leu
                405                 410                 415
Thr Asp Lys His Lys Ala Val Leu Gln Ser Lys Glu Lys Ile Leu Thr
                420                 425                 430
Asp Ser Tyr Lys Phe Arg Ala Lys Asp Gly Ser Phe Val Thr Leu Lys
                435                 440                 445
Ser Gln Trp Phe Ser Phe Thr Asn Pro Trp Thr Lys Glu Leu Glu Tyr
                450                 455                 460
Ile Val Ser Val Asn Thr Leu Val Leu Gly His Ser Glu Pro Gly Glu
465                 470                 475                 480
Ala Ser Phe Leu Pro Cys Ser Ser Gln Ser Ser Glu Ser Ser Arg
                485                 490                 495
Gln Ser Cys Met Ser Val Pro Gly Met Ser Thr Gly Thr Val Leu Gly
                500                 505                 510
Ala Gly Ser Ile Gly Thr Asp Ile Ala Asn Glu Ile Leu Asp Leu Gln
                515                 520                 525
Arg Leu Gln Ser Ser Ser Tyr Leu Asp Asp Ser Ser Pro Thr Gly Leu
                530                 535                 540
Met Lys Asp Thr His Thr Val Asn Cys Arg Ser Met Ser Asn Lys Glu
545                 550                 555                 560
Leu Phe Pro Pro Ser Pro Ser Glu Met Gly Glu Leu Glu Ala Thr Arg
                565                 570                 575
Gln Asn Gln Ser Thr Val Ala Val His Ser His Glu Pro Leu Leu Ser
                580                 585                 590
Asp Gly Ala Gln Leu Asp Phe Asp Ala Leu Cys Asp Asn Asp Asp Thr
                595                 600                 605
Ala Met Ala Ala Phe Met Asn Tyr Leu Glu Ala Glu Gly Gly Leu Gly
                610                 615                 620
Asp Pro Gly Asp Phe Ser Asp Ile Gln Trp Thr Leu
625                 630                 635

<210> SEQ ID NO 3
<211> LENGTH: 1888
<212> TYPE: DNA
<213> ORGANISM: Homo sapiens
<220> FEATURE:
<221> NAME/KEY: CDS
<222> LOCATION: (19)..(1884)

<400> SEQUENCE: 3
gaccaagtgg ctcctgcg atg gcg gcg gaa gag gag gct gcg gcg gga ggt     51
                    Met Ala Ala Glu Glu Glu Ala Ala Ala Gly Gly
                     1               5                   10 aaa gtg ttg aga gag gag aac cag tgc att gct cct gtg gtt tcc agc    99
Lys Val Leu Arg Glu Glu Asn Gln Cys Ile Ala Pro Val Val Ser Ser
```

|  |  |  |  |  |  |  |  |  |  |  |  |  |  |  |  |
|---|---|---|---|---|---|---|---|---|---|---|---|---|---|---|---|
|  |  |  | 15 |  |  |  |  | 20 |  |  |  |  | 25 |  |  |

```
cgc gtg agt cca ggg aca aga cca aca gct atg ggg tct ttc agc tca       147
Arg Val Ser Pro Gly Thr Arg Pro Thr Ala Met Gly Ser Phe Ser Ser
         30                  35                  40 cac atg aca gag ttt cca cga aaa cgc aaa gga agt gat tca gac cca       195
His Met Thr Glu Phe Pro Arg Lys Arg Lys Gly Ser Asp Ser Asp Pro
     45                  50                  55 tcc cag tca gga atc atg aca gaa aaa gtg gtg gaa aag ctt tct cag       243
Ser Gln Ser Gly Ile Met Thr Glu Lys Val Val Glu Lys Leu Ser Gln
 60                  65                  70                  75 aat ccc ctt acc tat ctt ctt tca aca agg ata gaa ata tca gcc tcc       291
Asn Pro Leu Thr Tyr Leu Leu Ser Thr Arg Ile Glu Ile Ser Ala Ser
                 80                  85                  90 agt ggc agc aga gaa gct cat agc caa act gaa aag cgg agg aga gat       339
Ser Gly Ser Arg Glu Ala His Ser Gln Thr Glu Lys Arg Arg Arg Asp
             95                 100                 105 aaa atg aat aac ctg att gaa gaa ctg tct gca atg atc cct cag tgc       387
Lys Met Asn Asn Leu Ile Glu Glu Leu Ser Ala Met Ile Pro Gln Cys
         110                 115                 120 aac ccc atg gcg cgt aaa ctg gac aaa ctt aca gtt tta aga atg gct       435
Asn Pro Met Ala Arg Lys Leu Asp Lys Leu Thr Val Leu Arg Met Ala
     125                 130                 135 gtt caa cac ttg aga tct tta aaa ggc ttg aca aat tct tat gtg gga       483
Val Gln His Leu Arg Ser Leu Lys Gly Leu Thr Asn Ser Tyr Val Gly
140                 145                 150                 155 agt aat tat aga cca tca ttt ctt cag gat aat gag ctc aga cat tta       531
Ser Asn Tyr Arg Pro Ser Phe Leu Gln Asp Asn Glu Leu Arg His Leu
                 160                 165                 170 atc ctt aag act gca gaa ggc ttc tta ttt gtg gtt gga tgt gaa aga       579
Ile Leu Lys Thr Ala Glu Gly Phe Leu Phe Val Val Gly Cys Glu Arg
             175                 180                 185 gga aaa att ctc ttc gtt tct aag tca gtc tcc aaa ata ctt aat tat       627
Gly Lys Ile Leu Phe Val Ser Lys Ser Val Ser Lys Ile Leu Asn Tyr
         190                 195                 200 gat cag gct agt ttg act gga caa agc tta ttt gac ttc tta cat cca       675
Asp Gln Ala Ser Leu Thr Gly Gln Ser Leu Phe Asp Phe Leu His Pro
     205                 210                 215 aaa gat gtt gcc aaa gta aag gaa caa ctt tct tct ttt gat att tca       723
Lys Asp Val Ala Lys Val Lys Glu Gln Leu Ser Ser Phe Asp Ile Ser
220                 225                 230                 235 cca aga gaa aag cta ata gat gcc aaa act ggt ttg caa gtt cac agt       771
Pro Arg Glu Lys Leu Ile Asp Ala Lys Thr Gly Leu Gln Val His Ser
                 240                 245                 250 aat ctc cac gct gga agg aca cgt gtg tat tct ggc tca aga cga tct       819
Asn Leu His Ala Gly Arg Thr Arg Val Tyr Ser Gly Ser Arg Arg Ser
             255                 260                 265 ttt ttc tgt cgg ata aag agt tgt aaa atc tct gtc aaa gaa gag cat       867
Phe Phe Cys Arg Ile Lys Ser Cys Lys Ile Ser Val Lys Glu Glu His
         270                 275                 280 gga tgc tta ccc aac tca aag aag aaa gag cac aga aaa ttc tat act       915
Gly Cys Leu Pro Asn Ser Lys Lys Lys Glu His Arg Lys Phe Tyr Thr
     285                 290                 295 atc cat tgc act ggt tac ttg aga agc tgg cct cca aat att gtt gga       963
Ile His Cys Thr Gly Tyr Leu Arg Ser Trp Pro Pro Asn Ile Val Gly
300                 305                 310                 315 atg gaa gaa gaa agg aac agt aag aaa gac aac agt aat ttt acc tgc      1011
Met Glu Glu Glu Arg Asn Ser Lys Lys Asp Asn Ser Asn Phe Thr Cys
                 320                 325                 330 ctt gtg gcc att gga aga tta cag cca tat att gtt cca cag aac agt      1059
Leu Val Ala Ile Gly Arg Leu Gln Pro Tyr Ile Val Pro Gln Asn Ser
```

```
Leu Val Ala Ile Gly Arg Leu Gln Pro Tyr Ile Val Pro Gln Asn Ser
                335                 340                 345 gga gag att aat gtg aaa cca act gaa ttt ata acc cgg ttt gca gtg      1107
Gly Glu Ile Asn Val Lys Pro Thr Glu Phe Ile Thr Arg Phe Ala Val
            350                 355                 360 aat gga aaa ttt gtc tat gta gat caa agg gca aca gcg att tta gga      1155
Asn Gly Lys Phe Val Tyr Val Asp Gln Arg Ala Thr Ala Ile Leu Gly
        365                 370                 375 tat ctg cct cag gaa ctt ttg gga act tct tgt tat gaa tat ttt cat      1203
Tyr Leu Pro Gln Glu Leu Leu Gly Thr Ser Cys Tyr Glu Tyr Phe His
380                 385                 390                 395 caa gat gac cac aat aat ttg act gac aag cac aaa gca gtt cta cag      1251
Gln Asp Asp His Asn Asn Leu Thr Asp Lys His Lys Ala Val Leu Gln
                400                 405                 410 agt aag gag aaa ata ctt aca gat tcc tac aaa ttc aga gca aaa gat      1299
Ser Lys Glu Lys Ile Leu Thr Asp Ser Tyr Lys Phe Arg Ala Lys Asp
            415                 420                 425 ggc tct ttt gta act tta aaa agc caa tgg ttt agt ttc aca aat cct      1347
Gly Ser Phe Val Thr Leu Lys Ser Gln Trp Phe Ser Phe Thr Asn Pro
        430                 435                 440 tgg aca aaa gaa ctg gaa tat att gta tct gtc aac act tta gtt ttg      1395
Trp Thr Lys Glu Leu Glu Tyr Ile Val Ser Val Asn Thr Leu Val Leu
    445                 450                 455 gga cat agt gag cct gga gaa gca tca ttt tta cct tgt agc tct caa      1443
Gly His Ser Glu Pro Gly Glu Ala Ser Phe Leu Pro Cys Ser Ser Gln
460                 465                 470                 475 tca tca gaa gaa tcc tct aga cag tcc tgt atg agt gta cct gga atg      1491
Ser Ser Glu Glu Ser Ser Arg Gln Ser Cys Met Ser Val Pro Gly Met
                480                 485                 490 tct act gga aca gta ctt ggt gct ggt agt att gga aca gat att gca      1539
Ser Thr Gly Thr Val Leu Gly Ala Gly Ser Ile Gly Thr Asp Ile Ala
            495                 500                 505 aat gaa att ctg gat tta cag agg tta cag tct tct tca tac ctt gat      1587
Asn Glu Ile Leu Asp Leu Gln Arg Leu Gln Ser Ser Ser Tyr Leu Asp
        510                 515                 520 gat tcg agt cca aca ggt tta atg aaa gat act cat act gta aac tgc      1635
Asp Ser Ser Pro Thr Gly Leu Met Lys Asp Thr His Thr Val Asn Cys
    525                 530                 535 agg agt atg tca aat aag gag ttg ttt cca cca agt cct tct gaa atg      1683
Arg Ser Met Ser Asn Lys Glu Leu Phe Pro Pro Ser Pro Ser Glu Met
540                 545                 550                 555 ggg gag cta gag gct acc agg caa aac cag agt act gtt gct gtc cac      1731
Gly Glu Leu Glu Ala Thr Arg Gln Asn Gln Ser Thr Val Ala Val His
                560                 565                 570 agc cat gag cca ctc ctc agt gat ggt gca cag ttg gat ttc gat gcc      1779
Ser His Glu Pro Leu Leu Ser Asp Gly Ala Gln Leu Asp Phe Asp Ala
            575                 580                 585 cta tgt gac aat gat gac aca gcc atg gct gca ttt atg aat tac tta      1827
Leu Cys Asp Asn Asp Asp Thr Ala Met Ala Ala Phe Met Asn Tyr Leu
        590                 595                 600 gaa gca gag ggg ggc ctg gga gac cct ggg gac ttc agt gac atc cag      1875
Glu Ala Glu Gly Gly Leu Gly Asp Pro Gly Asp Phe Ser Asp Ile Gln
    605                 610                 615 tgg acc ctc tagc                                                     1888
Trp Thr Leu
620

<210> SEQ ID NO 4
<211> LENGTH: 622
<212> TYPE: PRT
```

<213> ORGANISM: Homo sapiens

<400> SEQUENCE: 4

```
Met Ala Ala Glu Glu Ala Ala Gly Gly Lys Val Leu Arg Glu
 1               5                  10                  15
Glu Asn Gln Cys Ile Ala Pro Val Val Ser Ser Arg Val Ser Pro Gly
            20                  25                  30
Thr Arg Pro Thr Ala Met Gly Ser Phe Ser Ser His Met Thr Glu Phe
        35                  40                  45
Pro Arg Lys Arg Lys Gly Ser Asp Ser Asp Pro Ser Gln Ser Gly Ile
    50                  55                  60
Met Thr Glu Lys Val Val Glu Lys Leu Ser Gln Asn Pro Leu Thr Tyr
65                  70                  75                  80
Leu Leu Ser Thr Arg Ile Glu Ile Ser Ala Ser Ser Gly Ser Arg Glu
                85                  90                  95
Ala His Ser Gln Thr Glu Lys Arg Arg Arg Asp Lys Met Asn Asn Leu
            100                 105                 110
Ile Glu Glu Leu Ser Ala Met Ile Pro Gln Cys Asn Pro Met Ala Arg
        115                 120                 125
Lys Leu Asp Lys Leu Thr Val Leu Arg Met Ala Val Gln His Leu Arg
    130                 135                 140
Ser Leu Lys Gly Leu Thr Asn Ser Tyr Val Gly Ser Asn Tyr Arg Pro
145                 150                 155                 160
Ser Phe Leu Gln Asp Asn Glu Leu Arg His Leu Ile Leu Lys Thr Ala
                165                 170                 175
Glu Gly Phe Leu Phe Val Val Gly Cys Glu Arg Gly Lys Ile Leu Phe
            180                 185                 190
Val Ser Lys Ser Val Ser Lys Ile Leu Asn Tyr Asp Gln Ala Ser Leu
        195                 200                 205
Thr Gly Gln Ser Leu Phe Asp Phe Leu His Pro Lys Asp Val Ala Lys
    210                 215                 220
Val Lys Glu Gln Leu Ser Ser Phe Asp Ile Ser Pro Arg Glu Lys Leu
225                 230                 235                 240
Ile Asp Ala Lys Thr Gly Leu Gln Val His Ser Asn Leu His Ala Gly
                245                 250                 255
Arg Thr Arg Val Tyr Ser Gly Ser Arg Arg Ser Phe Phe Cys Arg Ile
            260                 265                 270
Lys Ser Cys Lys Ile Ser Val Lys Glu Glu His Gly Cys Leu Pro Asn
        275                 280                 285
Ser Lys Lys Lys Glu His Arg Lys Phe Tyr Thr Ile His Cys Thr Gly
    290                 295                 300
Tyr Leu Arg Ser Trp Pro Pro Asn Ile Val Gly Met Glu Glu Glu Arg
305                 310                 315                 320
Asn Ser Lys Lys Asp Asn Ser Asn Phe Thr Cys Leu Val Ala Ile Gly
                325                 330                 335
Arg Leu Gln Pro Tyr Ile Val Pro Gln Asn Ser Gly Glu Ile Asn Val
            340                 345                 350
Lys Pro Thr Glu Phe Ile Thr Arg Phe Ala Val Asn Gly Lys Phe Val
        355                 360                 365
Tyr Val Asp Gln Arg Ala Thr Ala Ile Leu Gly Tyr Leu Pro Gln Glu
    370                 375                 380
Leu Leu Gly Thr Ser Cys Tyr Glu Tyr Phe His Gln Asp Asp His Asn
385                 390                 395                 400
```

-continued

| | | | | | | | | | | | |
|---|---|---|---|---|---|---|---|---|---|---|---|
|Asn|Leu|Thr|Asp|Lys|His|Lys|Ala|Val|Leu|Gln|Ser|Lys|Glu|Lys|Ile|
| | | |405| | | |410| | | |415|

Leu Thr Asp Ser Tyr Lys Phe Arg Ala Lys Asp Gly Ser Phe Val Thr
            420                 425                 430

Leu Lys Ser Gln Trp Phe Ser Phe Thr Asn Pro Trp Thr Lys Glu Leu
        435                 440                 445

Glu Tyr Ile Val Ser Val Asn Thr Leu Val Leu Gly His Ser Glu Pro
450                 455                 460

Gly Glu Ala Ser Phe Leu Pro Cys Ser Ser Gln Ser Ser Glu Glu Ser
465                 470                 475                 480

Ser Arg Gln Ser Cys Met Ser Val Pro Gly Met Ser Thr Gly Thr Val
                485                 490                 495

Leu Gly Ala Gly Ser Ile Gly Thr Asp Ile Ala Asn Glu Ile Leu Asp
            500                 505                 510

Leu Gln Arg Leu Gln Ser Ser Tyr Leu Asp Asp Ser Ser Pro Thr
        515                 520                 525

Gly Leu Met Lys Asp Thr His Thr Val Asn Cys Arg Ser Met Ser Asn
530                 535                 540

Lys Glu Leu Phe Pro Pro Ser Pro Ser Glu Met Gly Glu Leu Glu Ala
545                 550                 555                 560

Thr Arg Gln Asn Gln Ser Thr Val Ala Val His Ser His Glu Pro Leu
                565                 570                 575

Leu Ser Asp Gly Ala Gln Leu Asp Phe Asp Ala Leu Cys Asp Asn Asp
            580                 585                 590

Asp Thr Ala Met Ala Ala Phe Met Asn Tyr Leu Glu Ala Glu Gly Gly
        595                 600                 605

Leu Gly Asp Pro Gly Asp Phe Ser Asp Ile Gln Trp Thr Leu
610                 615                 620

<210> SEQ ID NO 5
<211> LENGTH: 1819
<212> TYPE: DNA
<213> ORGANISM: Homo sapiens
<220> FEATURE:
<221> NAME/KEY: CDS
<222> LOCATION: (19)..(1815)

<400> SEQUENCE: 5
gaccaagtgg ctcctgcg atg gcg gcg gaa gag gag gct gcg gcg gga ggt        51
                    Met Ala Ala Glu Glu Glu Ala Ala Ala Gly Gly
                     1               5                   10 gag gtt gcc ggt ggc gag gcg acg gcc cca ggt aaa gtg ttg aga gag       99
Glu Val Ala Gly Gly Glu Ala Thr Ala Pro Gly Lys Val Leu Arg Glu
            15                  20                  25 gag aac cag tgc att gct cct gtg gtt tcc agc cgc gtg agt cca ggg      147
Glu Asn Gln Cys Ile Ala Pro Val Val Ser Ser Arg Val Ser Pro Gly
        30                  35                  40 aca aga cca aca gct atg ggg tct ttc agc tca cac atg aca gag ttt      195
Thr Arg Pro Thr Ala Met Gly Ser Phe Ser Ser His Met Thr Glu Phe
    45                  50                  55 cca cga aaa cgc aaa gga agt gat tca gac cca tcc caa gaa gct cat      243
Pro Arg Lys Arg Lys Gly Ser Asp Ser Asp Pro Ser Gln Glu Ala His
60                  65                  70                  75 agc caa act gaa aag cgg agg aga gat aaa atg aat aac ctg att gaa      291
Ser Gln Thr Glu Lys Arg Arg Arg Asp Lys Met Asn Asn Leu Ile Glu
                80                  85                  90 gaa ctg tct gca atg atc cct cag tgc aac ccc atg gcg cgt aaa ctg      339
Glu Leu Ser Ala Met Ile Pro Gln Cys Asn Pro Met Ala Arg Lys Leu -continued

```
                95                    100                   105
gac aaa ctt aca gtt tta aga atg gct gtt caa cac ttg aga tct tta       387
Asp Lys Leu Thr Val Leu Arg Met Ala Val Gln His Leu Arg Ser Leu
        110                 115                 120 aaa ggc ttg aca aat tct tat gtg gga agt aat tat aga cca tca ttt       435
Lys Gly Leu Thr Asn Ser Tyr Val Gly Ser Asn Tyr Arg Pro Ser Phe
    125                 130                 135 ctt cag gat aat gag ctc aga cat tta atc ctt aag act gca gaa ggc       483
Leu Gln Asp Asn Glu Leu Arg His Leu Ile Leu Lys Thr Ala Glu Gly
140                 145                 150                 155 ttc tta ttt gtg gtt gga tgt gaa aga gga aaa att ctc ttc gtt tct       531
Phe Leu Phe Val Val Gly Cys Glu Arg Gly Lys Ile Leu Phe Val Ser
                160                 165                 170 aag tca gtc tcc aaa ata ctt aat tat gat cag gct agt ttg act gga       579
Lys Ser Val Ser Lys Ile Leu Asn Tyr Asp Gln Ala Ser Leu Thr Gly
            175                 180                 185 caa agc tta ttt gac ttc tta cat cca aaa gat gtt gcc aaa gta aag       627
Gln Ser Leu Phe Asp Phe Leu His Pro Lys Asp Val Ala Lys Val Lys
        190                 195                 200 gaa caa ctt tct tct ttt gat att tca cca aga gaa aag cta ata gat       675
Glu Gln Leu Ser Ser Phe Asp Ile Ser Pro Arg Glu Lys Leu Ile Asp
    205                 210                 215 gcc aaa act ggt ttg caa gtt cac agt aat ctc cac gct gga agg aca       723
Ala Lys Thr Gly Leu Gln Val His Ser Asn Leu His Ala Gly Arg Thr
220                 225                 230                 235 cgt gtg tat tct ggc tca aga cga tct ttt ttc tgt cgg ata aag agt       771
Arg Val Tyr Ser Gly Ser Arg Arg Ser Phe Phe Cys Arg Ile Lys Ser
                240                 245                 250 tgt aaa atc tct gtc aaa gaa gag cat gga tgc tta ccc aac tca aag       819
Cys Lys Ile Ser Val Lys Glu Glu His Gly Cys Leu Pro Asn Ser Lys
            255                 260                 265 aag aaa gag cac aga aaa ttc tat act atc cat tgc act ggt tac ttg       867
Lys Lys Glu His Arg Lys Phe Tyr Thr Ile His Cys Thr Gly Tyr Leu
        270                 275                 280 aga agc tgg cct cca aat att gtt gga atg gaa gaa gaa agg aac agt       915
Arg Ser Trp Pro Pro Asn Ile Val Gly Met Glu Glu Glu Arg Asn Ser
    285                 290                 295 aag aaa gac aac agt aat ttt acc tgc ctt gtg gcc att gga aga tta       963
Lys Lys Asp Asn Ser Asn Phe Thr Cys Leu Val Ala Ile Gly Arg Leu
300                 305                 310                 315 cag cca tat att gtt cca cag aac agt gga gag att aat gtg aaa cca      1011
Gln Pro Tyr Ile Val Pro Gln Asn Ser Gly Glu Ile Asn Val Lys Pro
                320                 325                 330 act gaa ttt ata acc cgg ttt gca gtg aat gga aaa ttt gtc tat gta      1059
Thr Glu Phe Ile Thr Arg Phe Ala Val Asn Gly Lys Phe Val Tyr Val
            335                 340                 345 gat caa agg gca aca gcg att tta gga tat ctg cct cag gaa ctt ttg      1107
Asp Gln Arg Ala Thr Ala Ile Leu Gly Tyr Leu Pro Gln Glu Leu Leu
        350                 355                 360 gga act tct tgt tat gaa tat ttt cat caa gat gac cac aat aat ttg      1155
Gly Thr Ser Cys Tyr Glu Tyr Phe His Gln Asp Asp His Asn Asn Leu
    365                 370                 375 act gac aag cac aaa gca gtt cta cag agt aag gag aaa ata ctt aca      1203
Thr Asp Lys His Lys Ala Val Leu Gln Ser Lys Glu Lys Ile Leu Thr
380                 385                 390                 395 gat tcc tac aaa ttc aga gca aaa gat ggc tct ttt gta act tta aaa      1251
Asp Ser Tyr Lys Phe Arg Ala Lys Asp Gly Ser Phe Val Thr Leu Lys
                400                 405                 410 agc caa tgg ttt agt ttc aca aat cct tgg aca aaa gaa ctg gaa tat      1299
```

```
                Ser Gln Trp Phe Ser Phe Thr Asn Pro Trp Thr Lys Glu Leu Glu Tyr
                                415                 420                 425 att gta tct gtc aac act tta gtt ttg gga cat agt gag cct gga gaa         1347
Ile Val Ser Val Asn Thr Leu Val Leu Gly His Ser Glu Pro Gly Glu
        430                 435                 440 gca tca ttt tta cct tgt agc tct caa tca tca gaa gaa tcc tct aga         1395
Ala Ser Phe Leu Pro Cys Ser Ser Gln Ser Ser Glu Glu Ser Ser Arg
        445                 450                 455 cag tcc tgt atg agt gta cct gga atg tct act gga aca gta ctt ggt         1443
Gln Ser Cys Met Ser Val Pro Gly Met Ser Thr Gly Thr Val Leu Gly
460                 465                 470                 475 gct ggt agt att gga aca gat att gca aat gaa att ctg gat tta cag         1491
Ala Gly Ser Ile Gly Thr Asp Ile Ala Asn Glu Ile Leu Asp Leu Gln
                480                 485                 490 agg tta cag tct tct tca tac ctt gat gat tcg agt cca aca ggt tta         1539
Arg Leu Gln Ser Ser Ser Tyr Leu Asp Asp Ser Ser Pro Thr Gly Leu
            495                 500                 505 atg aaa gat act cat act gta aac tgc agg agt atg tca aat aag gag         1587
Met Lys Asp Thr His Thr Val Asn Cys Arg Ser Met Ser Asn Lys Glu
        510                 515                 520 ttg ttt cca cca agt cct tct gaa atg ggg gag cta gag gct acc agg         1635
Leu Phe Pro Pro Ser Pro Ser Glu Met Gly Glu Leu Glu Ala Thr Arg
    525                 530                 535 caa aac cag agt act gtt gct gtc cac agc cat gag cca ctc ctc agt         1683
Gln Asn Gln Ser Thr Val Ala Val His Ser His Glu Pro Leu Leu Ser
540                 545                 550                 555 gat ggt gca cag ttg gat ttc gat gcc cta tgt gac aat gat gac aca         1731
Asp Gly Ala Gln Leu Asp Phe Asp Ala Leu Cys Asp Asn Asp Asp Thr
                560                 565                 570 gcc atg gct gca ttt atg aat tac tta gaa gca gag ggg ggc ctg gga         1779
Ala Met Ala Ala Phe Met Asn Tyr Leu Glu Ala Glu Gly Gly Leu Gly
            575                 580                 585 gac cct ggg gac ttc agt gac atc cag tgg acc ctc tagc                    1819
Asp Pro Gly Asp Phe Ser Asp Ile Gln Trp Thr Leu
        590                 595

<210> SEQ ID NO 6
<211> LENGTH: 599
<212> TYPE: PRT
<213> ORGANISM: Homo sapiens

<400> SEQUENCE: 6

Met Ala Ala Glu Glu Ala Ala Ala Gly Gly Glu Val Ala Gly Gly
  1               5                  10                  15

Glu Ala Thr Ala Pro Gly Lys Val Leu Arg Glu Glu Asn Gln Cys Ile
                 20                  25                  30

Ala Pro Val Val Ser Ser Arg Val Ser Pro Gly Thr Arg Pro Thr Ala
             35                  40                  45

Met Gly Ser Phe Ser Ser His Met Thr Glu Phe Pro Arg Lys Arg Lys
         50                  55                  60

Gly Ser Asp Ser Asp Pro Ser Gln Glu Ala His Ser Gln Thr Glu Lys
 65                  70                  75                  80

Arg Arg Arg Asp Lys Met Asn Asn Leu Ile Glu Glu Leu Ser Ala Met
                 85                  90                  95

Ile Pro Gln Cys Asn Pro Met Ala Arg Lys Leu Asp Lys Leu Thr Val
            100                 105                 110

Leu Arg Met Ala Val Gln His Leu Arg Ser Leu Lys Gly Leu Thr Asn
        115                 120                 125
```

```
Ser Tyr Val Gly Ser Asn Tyr Arg Pro Ser Phe Leu Gln Asp Asn Glu
    130                 135                 140

Leu Arg His Leu Ile Leu Lys Thr Ala Glu Gly Phe Leu Phe Val Val
145                 150                 155                 160

Gly Cys Glu Arg Gly Lys Ile Leu Phe Val Ser Lys Ser Val Ser Lys
                165                 170                 175

Ile Leu Asn Tyr Asp Gln Ala Ser Leu Thr Gly Gln Ser Leu Phe Asp
                180                 185                 190

Phe Leu His Pro Lys Asp Val Ala Lys Val Lys Glu Gln Leu Ser Ser
            195                 200                 205

Phe Asp Ile Ser Pro Arg Glu Lys Leu Ile Asp Ala Lys Thr Gly Leu
    210                 215                 220

Gln Val His Ser Asn Leu His Ala Gly Arg Thr Arg Val Tyr Ser Gly
225                 230                 235                 240

Ser Arg Arg Ser Phe Phe Cys Arg Ile Lys Ser Cys Lys Ile Ser Val
                245                 250                 255

Lys Glu Glu His Gly Cys Leu Pro Asn Ser Lys Lys Glu His Arg
                260                 265                 270

Lys Phe Tyr Thr Ile His Cys Thr Gly Tyr Leu Arg Ser Trp Pro Pro
        275                 280                 285

Asn Ile Val Gly Met Glu Glu Glu Arg Asn Ser Lys Lys Asp Asn Ser
290                 295                 300

Asn Phe Thr Cys Leu Val Ala Ile Gly Arg Leu Gln Pro Tyr Ile Val
305                 310                 315                 320

Pro Gln Asn Ser Gly Glu Ile Asn Val Lys Pro Thr Glu Phe Ile Thr
                325                 330                 335

Arg Phe Ala Val Asn Gly Lys Phe Val Tyr Val Asp Gln Arg Ala Thr
                340                 345                 350

Ala Ile Leu Gly Tyr Leu Pro Gln Glu Leu Leu Gly Thr Ser Cys Tyr
            355                 360                 365

Glu Tyr Phe His Gln Asp Asp His Asn Asn Leu Thr Asp Lys His Lys
    370                 375                 380

Ala Val Leu Gln Ser Lys Glu Lys Ile Leu Thr Asp Ser Tyr Lys Phe
385                 390                 395                 400

Arg Ala Lys Asp Gly Ser Phe Val Thr Leu Lys Ser Gln Trp Phe Ser
                405                 410                 415

Phe Thr Asn Pro Trp Thr Lys Glu Leu Glu Tyr Ile Val Ser Val Asn
            420                 425                 430

Thr Leu Val Leu Gly His Ser Glu Pro Gly Glu Ala Ser Phe Leu Pro
    435                 440                 445

Cys Ser Ser Gln Ser Ser Glu Glu Ser Ser Arg Gln Ser Cys Met Ser
450                 455                 460

Val Pro Gly Met Ser Thr Gly Thr Val Leu Gly Ala Gly Ser Ile Gly
465                 470                 475                 480

Thr Asp Ile Ala Asn Glu Ile Leu Asp Leu Gln Arg Leu Gln Ser Ser
                485                 490                 495

Ser Tyr Leu Asp Asp Ser Pro Thr Gly Leu Met Lys Asp Thr His
            500                 505                 510

Thr Val Asn Cys Arg Ser Met Ser Asn Lys Glu Leu Phe Pro Pro Ser
        515                 520                 525

Pro Ser Glu Met Gly Glu Leu Glu Ala Thr Arg Gln Asn Gln Ser Thr
    530                 535                 540

Val Ala Val His Ser His Glu Pro Leu Leu Ser Asp Gly Ala Gln Leu
```

```
                    545                 550                 555                 560
             Asp Phe Asp Ala Leu Cys Asp Asn Asp Asp Thr Ala Met Ala Ala Phe
                             565                 570                 575

Met Asn Tyr Leu Glu Ala Glu Gly Gly Leu Gly Asp Pro Gly Asp Phe
                             580                 585                 590

Ser Asp Ile Gln Trp Thr Leu
                             595

<210> SEQ ID NO 7
<211> LENGTH: 1786
<212> TYPE: DNA
<213> ORGANISM: Homo sapiens
<220> FEATURE:
<221> NAME/KEY: CDS
<222> LOCATION: (19)..(1782)

<400> SEQUENCE: 7
gaccaagtgg ctcctgcg atg gcg gcg gaa gag gag gct gcg gcg gga ggt          51
                    Met Ala Ala Glu Glu Glu Ala Ala Ala Gly Gly
                    1               5                   10 aaa gtg ttg aga gag gag aac cag tgc att gct cct gtg gtt tcc agc         99
Lys Val Leu Arg Glu Glu Asn Gln Cys Ile Ala Pro Val Val Ser Ser
            15                  20                  25 cgc gtg agt cca ggg aca aga cca aca gct atg ggg tct ttc agc tca        147
Arg Val Ser Pro Gly Thr Arg Pro Thr Ala Met Gly Ser Phe Ser Ser
        30                  35                  40 cac atg aca gag ttt cca cga aaa cgc aaa gga agt gat tca gac cca        195
His Met Thr Glu Phe Pro Arg Lys Arg Lys Gly Ser Asp Ser Asp Pro
    45                  50                  55 tcc caa gaa gct cat agc caa act gaa aag cgg agg aga gat aaa atg        243
Ser Gln Glu Ala His Ser Gln Thr Glu Lys Arg Arg Arg Asp Lys Met
60                  65                  70                  75 aat aac ctg att gaa gaa ctg tct gca atg atc cct cag tgc aac ccc        291
Asn Asn Leu Ile Glu Glu Leu Ser Ala Met Ile Pro Gln Cys Asn Pro
                80                  85                  90 atg gcg cgt aaa ctg gac aaa ctt aca gtt tta aga atg gct gtt caa        339
Met Ala Arg Lys Leu Asp Lys Leu Thr Val Leu Arg Met Ala Val Gln
            95                  100                 105 cac ttg aga tct tta aaa ggc ttg aca aat tct tat gtg gga agt aat        387
His Leu Arg Ser Leu Lys Gly Leu Thr Asn Ser Tyr Val Gly Ser Asn
        110                 115                 120 tat aga cca tca ttt ctt cag gat aat gag ctc aga cat tta atc ctt        435
Tyr Arg Pro Ser Phe Leu Gln Asp Asn Glu Leu Arg His Leu Ile Leu
    125                 130                 135 aag act gca gaa ggc ttc tta ttt gtg gtt gga tgt gaa aga gga aaa        483
Lys Thr Ala Glu Gly Phe Leu Phe Val Val Gly Cys Glu Arg Gly Lys
140                 145                 150                 155 att ctc ttc gtt tct aag tca gtc tcc aaa ata ctt aat tat gat cag        531
Ile Leu Phe Val Ser Lys Ser Val Ser Lys Ile Leu Asn Tyr Asp Gln
                160                 165                 170 gct agt ttg act gga caa agc tta ttt gac ttc tta cat cca aaa gat        579
Ala Ser Leu Thr Gly Gln Ser Leu Phe Asp Phe Leu His Pro Lys Asp
            175                 180                 185 gtt gcc aaa gta aag gaa caa ctt tct tct ttt gat att tca cca aga        627
Val Ala Lys Val Lys Glu Gln Leu Ser Ser Phe Asp Ile Ser Pro Arg
        190                 195                 200 gaa aag cta ata gat gcc aaa act ggt tgc aag ttc aca gtt atg ctc       675
Glu Lys Leu Ile Asp Ala Lys Thr Gly Leu Gln Val His Ser Asn Leu
    205                 210                 215 cac gct gga agg aca cgt gtg tat tct ggc tca aga cga tct ttt ttc        723
```

```
                                                     -continued

His Ala Gly Arg Thr Arg Val Tyr Ser Gly Ser Arg Ser Phe Phe
220             225                 230             235 tgt cgg ata aag agt tgt aaa atc tct gtc aaa gaa gag cat gga tgc      771
Cys Arg Ile Lys Ser Cys Lys Ile Ser Val Lys Glu Glu His Gly Cys
                240                 245                 250 tta ccc aac tca aag aag aaa gag cac aga aaa ttc tat act atc cat      819
Leu Pro Asn Ser Lys Lys Lys Glu His Arg Lys Phe Tyr Thr Ile His
                255                 260                 265 tgc act ggt tac ttg aga agc tgg cct cca aat att gtt gga atg gaa      867
Cys Thr Gly Tyr Leu Arg Ser Trp Pro Pro Asn Ile Val Gly Met Glu
        270                 275                 280 gaa gaa agg aac agt aag aaa gac aac agt aat ttt acc tgc ctt gtg      915
Glu Glu Arg Asn Ser Lys Lys Asp Asn Ser Asn Phe Thr Cys Leu Val
285                 290                 295 gcc att gga aga tta cag cca tat att gtt cca cag aac agt gga gag      963
Ala Ile Gly Arg Leu Gln Pro Tyr Ile Val Pro Gln Asn Ser Gly Glu
300                 305                 310                 315 att aat gtg aaa cca act gaa ttt ata acc cgg ttt gca gtg aat gga     1011
Ile Asn Val Lys Pro Thr Glu Phe Ile Thr Arg Phe Ala Val Asn Gly
                320                 325                 330 aaa ttt gtc tat gta gat caa agg gca aca gcg att tta gga tat ctg     1059
Lys Phe Val Tyr Val Asp Gln Arg Ala Thr Ala Ile Leu Gly Tyr Leu
                335                 340                 345 cct cag gaa ctt ttg gga act tct tgt tat gaa tat ttt cat caa gat     1107
Pro Gln Glu Leu Leu Gly Thr Ser Cys Tyr Glu Tyr Phe His Gln Asp
        350                 355                 360 gac cac aat aat ttg act gac aag cac aaa gca gtt cta cag agt aag     1155
Asp His Asn Asn Leu Thr Asp Lys His Lys Ala Val Leu Gln Ser Lys
365                 370                 375 gag aaa ata ctt aca gat tcc tac aaa ttc aga gca aaa gat ggc tct     1203
Glu Lys Ile Leu Thr Asp Ser Tyr Lys Phe Arg Ala Lys Asp Gly Ser
380                 385                 390                 395 ttt gta act tta aaa agc caa tgg ttt agt ttc aca aat cct tgg aca     1251
Phe Val Thr Leu Lys Ser Gln Trp Phe Ser Phe Thr Asn Pro Trp Thr
                400                 405                 410 aaa gaa ctg gaa tat att gta tct gtc aac act tta gtt ttg gga cat     1299
Lys Glu Leu Glu Tyr Ile Val Ser Val Asn Thr Leu Val Leu Gly His
                415                 420                 425 agt gag cct gga gaa gca tca ttt tta cct tgt agc tct caa tca tca     1347
Ser Glu Pro Gly Glu Ala Ser Phe Leu Pro Cys Ser Ser Gln Ser Ser
        430                 435                 440 gaa gaa tcc tct aga cag tcc tgt atg agt gta cct gga atg tct act     1395
Glu Glu Ser Ser Arg Gln Ser Cys Met Ser Val Pro Gly Met Ser Thr
445                 450                 455 gga aca gta ctt ggt gct ggt agt att gga aca gat att gca aat gaa     1443
Gly Thr Val Leu Gly Ala Gly Ser Ile Gly Thr Asp Ile Ala Asn Glu
460                 465                 470                 475 att ctg gat tta cag agg tta cag tct tct tca tac ctt gat gat tcg     1491
Ile Leu Asp Leu Gln Arg Leu Gln Ser Ser Ser Tyr Leu Asp Asp Ser
                480                 485                 490 agt cca aca ggt tta atg aaa gat act cat act gta aac tgc agg agt     1539
Ser Pro Thr Gly Leu Met Lys Asp Thr His Thr Val Asn Cys Arg Ser
                495                 500                 505 atg tca aat aag gag ttg ttt cca cca agt cct tct gaa atg ggg gag     1587
Met Ser Asn Lys Glu Leu Phe Pro Pro Ser Pro Ser Glu Met Gly Glu
        510                 515                 520 cta gag gct acc agg caa aac cag agt act gtt gct gtc cac agc cat     1635
Leu Glu Ala Thr Arg Gln Asn Gln Ser Thr Val Ala Val His Ser His
525                 530                 535
```

-continued

```
gag cca ctc ctc agt gat ggt gca cag ttg gat ttc gat gcc cta tgt    1683
Glu Pro Leu Leu Ser Asp Gly Ala Gln Leu Asp Phe Asp Ala Leu Cys
540             545                 550                 555 gac aat gat gac aca gcc atg gct gca ttt atg aat tac tta gaa gca    1731
Asp Asn Asp Asp Thr Ala Met Ala Ala Phe Met Asn Tyr Leu Glu Ala
                560                 565                 570 gag ggg ggc ctg gga gac cct ggg gac ttc agt gac atc cag tgg acc    1779
Glu Gly Gly Leu Gly Asp Pro Gly Asp Phe Ser Asp Ile Gln Trp Thr
        575                 580                 585 ctc tagc                                                            1786
Leu

<210> SEQ ID NO 8
<211> LENGTH: 588
<212> TYPE: PRT
<213> ORGANISM: Homo sapiens

<400> SEQUENCE: 8

Met Ala Ala Glu Glu Ala Ala Gly Gly Lys Val Leu Arg Glu
 1               5                  10                  15

Glu Asn Gln Cys Ile Ala Pro Val Val Ser Ser Arg Val Ser Pro Gly
                20                  25                  30

Thr Arg Pro Thr Ala Met Gly Ser Phe Ser Ser His Met Thr Glu Phe
            35                  40                  45

Pro Arg Lys Arg Lys Gly Ser Asp Ser Asp Pro Ser Gln Glu Ala His
        50                  55                  60

Ser Gln Thr Glu Lys Arg Arg Asp Lys Met Asn Asn Leu Ile Glu
 65                  70                  75                  80

Glu Leu Ser Ala Met Ile Pro Gln Cys Asn Pro Met Ala Arg Lys Leu
                85                  90                  95

Asp Lys Leu Thr Val Leu Arg Met Ala Val Gln His Leu Arg Ser Leu
            100                 105                 110

Lys Gly Leu Thr Asn Ser Tyr Val Gly Ser Asn Tyr Arg Pro Ser Phe
        115                 120                 125

Leu Gln Asp Asn Glu Leu Arg His Leu Ile Leu Lys Thr Ala Glu Gly
    130                 135                 140

Phe Leu Phe Val Val Gly Cys Glu Arg Gly Lys Ile Leu Phe Val Ser
145                 150                 155                 160

Lys Ser Val Ser Lys Ile Leu Asn Tyr Asp Gln Ala Ser Leu Thr Gly
                165                 170                 175

Gln Ser Leu Phe Asp Phe Leu His Pro Lys Asp Val Ala Lys Val Lys
            180                 185                 190

Glu Gln Leu Ser Ser Phe Asp Ile Ser Pro Arg Glu Lys Leu Ile Asp
        195                 200                 205

Ala Lys Thr Gly Leu Gln Val His Ser Asn Leu His Ala Gly Arg Thr
    210                 215                 220

Arg Val Tyr Ser Gly Ser Arg Arg Ser Phe Phe Cys Arg Ile Lys Ser
225                 230                 235                 240

Cys Lys Ile Ser Val Lys Glu Glu His Gly Cys Leu Pro Asn Ser Lys
                245                 250                 255

Lys Lys Glu His Arg Lys Phe Tyr Thr Ile His Cys Thr Gly Tyr Leu
            260                 265                 270

Arg Ser Trp Pro Pro Asn Ile Val Gly Met Glu Glu Arg Asn Ser
        275                 280                 285

Lys Lys Asp Asn Ser Asn Phe Thr Cys Leu Val Ala Ile Gly Arg Leu
    290                 295                 300
```

```
Gln Pro Tyr Ile Val Pro Gln Asn Ser Gly Glu Ile Asn Val Lys Pro
305                 310                 315                 320

Thr Glu Phe Ile Thr Arg Phe Ala Val Asn Gly Lys Phe Val Tyr Val
                325                 330                 335

Asp Gln Arg Ala Thr Ala Ile Leu Gly Tyr Leu Pro Gln Glu Leu Leu
            340                 345                 350

Gly Thr Ser Cys Tyr Glu Tyr Phe His Gln Asp His Asn Asn Leu
        355                 360                 365

Thr Asp Lys His Lys Ala Val Leu Gln Ser Lys Glu Lys Ile Leu Thr
    370                 375                 380

Asp Ser Tyr Lys Phe Arg Ala Lys Asp Gly Ser Phe Val Thr Leu Lys
385                 390                 395                 400

Ser Gln Trp Phe Ser Phe Thr Asn Pro Trp Thr Lys Glu Leu Glu Tyr
                405                 410                 415

Ile Val Ser Val Asn Thr Leu Val Leu Gly His Ser Glu Pro Gly Glu
            420                 425                 430

Ala Ser Phe Leu Pro Cys Ser Ser Gln Ser Ser Glu Glu Ser Ser Arg
        435                 440                 445

Gln Ser Cys Met Ser Val Pro Gly Met Ser Thr Gly Thr Val Leu Gly
    450                 455                 460

Ala Gly Ser Ile Gly Thr Asp Ile Ala Asn Glu Ile Leu Asp Leu Gln
465                 470                 475                 480

Arg Leu Gln Ser Ser Ser Tyr Leu Asp Asp Ser Ser Pro Thr Gly Leu
                485                 490                 495

Met Lys Asp Thr His Thr Val Asn Cys Arg Ser Met Ser Asn Lys Glu
            500                 505                 510

Leu Phe Pro Pro Ser Pro Ser Glu Met Gly Glu Leu Glu Ala Thr Arg
        515                 520                 525

Gln Asn Gln Ser Thr Val Ala Val His Ser His Glu Pro Leu Leu Ser
    530                 535                 540

Asp Gly Ala Gln Leu Asp Phe Asp Ala Leu Cys Asp Asn Asp Asp Thr
545                 550                 555                 560

Ala Met Ala Ala Phe Met Asn Tyr Leu Glu Ala Glu Gly Gly Leu Gly
                565                 570                 575

Asp Pro Gly Asp Phe Ser Asp Ile Gln Trp Thr Leu
            580                 585

<210> SEQ ID NO 9
<211> LENGTH: 1970
<212> TYPE: DNA
<213> ORGANISM: Gallus gallus
<220> FEATURE:
<221> NAME/KEY: CDS
<222> LOCATION: (102)..(1970)

<400> SEQUENCE: 9
cccccgggcc ggcaggacgg gccgttcctt ctcaccttag ttcacctccc gcatgccgcc    60
ggggccgggg gcgctgtgga gcggggctcg ggccgcccgc c atg gcc gag gca gga   116
                                             Met Ala Glu Ala Gly
                                               1               5 gtg ggg agc gcc gag ggg gca gag gag gag cgg cgg gcc gtt gaa gag    164
Val Gly Ser Ala Glu Gly Ala Glu Glu Glu Arg Arg Ala Val Glu Glu
           10                  15                  20 aat ttt cca gta gat gga aac tcg tgc att gct tct gga gtc ccc agc    212
Asn Phe Pro Val Asp Gly Asn Ser Cys Ile Ala Ser Gly Val Pro Ser
       25                  30                  35
```

|     |     |     |     |     |     |     |     |     |     |     |     |     |     |     |     |     |
|---|---|---|---|---|---|---|---|---|---|---|---|---|---|---|---|---|
| ctc | atg | aat | cca | ata | act | aag | cct | gct | acc | act | tct | ttc | aac | aat | tct | 260 |
| Leu | Met | Asn | Pro | Ile | Thr | Lys | Pro | Ala | Thr | Thr | Ser | Phe | Asn | Asn | Ser | |
| | 40 | | | | | 45 | | | | | 50 | | | | | |
| gtg | gtt | gag | att | cca | agg | aag | cgc | aaa | gga | agt | gat | tct | gat | aac | cag | 308 |
| Val | Val | Glu | Ile | Pro | Arg | Lys | Arg | Lys | Gly | Ser | Asp | Ser | Asp | Asn | Gln | |
| 55 | | | | | 60 | | | | | 65 | | | | | | |
| gat | aca | gtt | gaa | gtt | gat | ggg | gat | cct | cag | aaa | agg | aat | gaa | gat | gaa | 356 |
| Asp | Thr | Val | Glu | Val | Asp | Gly | Asp | Pro | Gln | Lys | Arg | Asn | Glu | Asp | Glu | |
| 70 | | | | 75 | | | | | 80 | | | | | 85 | | |
| gaa | cat | ctt | aag | ata | aaa | gat | ttc | aga | gag | gcc | cac | agt | caa | aca | gag | 404 |
| Glu | His | Leu | Lys | Ile | Lys | Asp | Phe | Arg | Glu | Ala | His | Ser | Gln | Thr | Glu | |
| | | | 90 | | | | | 95 | | | | | 100 | | | |
| aaa | cga | aga | aga | gac | aaa | atg | aat | aat | ttg | ata | gag | gaa | ttg | tct | gct | 452 |
| Lys | Arg | Arg | Arg | Asp | Lys | Met | Asn | Asn | Leu | Ile | Glu | Glu | Leu | Ser | Ala | |
| | | | 105 | | | | | 110 | | | | | 115 | | | |
| atg | ata | cct | cag | tgc | aat | cct | atg | gca | cga | aag | cta | gac | aag | ctt | aca | 500 |
| Met | Ile | Pro | Gln | Cys | Asn | Pro | Met | Ala | Arg | Lys | Leu | Asp | Lys | Leu | Thr | |
| | | 120 | | | | | 125 | | | | | 130 | | | | |
| gta | tta | cgg | atg | gca | gtg | caa | cac | tta | aaa | tct | ttg | aaa | ggt | tcc | act | 548 |
| Val | Leu | Arg | Met | Ala | Val | Gln | His | Leu | Lys | Ser | Leu | Lys | Gly | Ser | Thr | |
| 135 | | | | | 140 | | | | | 145 | | | | | | |
| agc | tct | tac | acc | gaa | gtc | cgg | tat | aaa | cct | tcg | ttt | tta | aag | gat | gat | 596 |
| Ser | Ser | Tyr | Thr | Glu | Val | Arg | Tyr | Lys | Pro | Ser | Phe | Leu | Lys | Asp | Asp | |
| 150 | | | | | 155 | | | | | 160 | | | | | 165 | |
| gag | ctc | aga | cag | tta | atc | ctt | agg | gct | gcg | gat | gga | ttc | cta | ttt | gtg | 644 |
| Glu | Leu | Arg | Gln | Leu | Ile | Leu | Arg | Ala | Ala | Asp | Gly | Phe | Leu | Phe | Val | |
| | | | 170 | | | | | 175 | | | | | 180 | | | |
| gtt | gga | tgt | aac | aga | gga | aaa | att | ctg | ttt | gtc | tca | gaa | tca | gtt | tgc | 692 |
| Val | Gly | Cys | Asn | Arg | Gly | Lys | Ile | Leu | Phe | Val | Ser | Glu | Ser | Val | Cys | |
| | | | 185 | | | | | 190 | | | | | 195 | | | |
| aaa | ata | ctt | aat | tat | gat | cag | acc | agt | tta | att | gga | caa | agt | ttg | ttt | 740 |
| Lys | Ile | Leu | Asn | Tyr | Asp | Gln | Thr | Ser | Leu | Ile | Gly | Gln | Ser | Leu | Phe | |
| | | 200 | | | | | 205 | | | | | 210 | | | | |
| gat | tac | ttg | cat | cca | aaa | gat | gtt | gcc | aaa | gtt | aag | gag | caa | ctt | tca | 788 |
| Asp | Tyr | Leu | His | Pro | Lys | Asp | Val | Ala | Lys | Val | Lys | Glu | Gln | Leu | Ser | |
| | | 215 | | | | | 220 | | | | | 225 | | | | |
| tct | tca | gat | gtc | tct | ccc | aga | gaa | aag | ctt | gta | gat | ggc | aaa | act | ggc | 836 |
| Ser | Ser | Asp | Val | Ser | Pro | Arg | Glu | Lys | Leu | Val | Asp | Gly | Lys | Thr | Gly | |
| 230 | | | | | 235 | | | | | 240 | | | | | 245 | |
| ttg | caa | gta | cat | aca | gat | ttt | caa | gct | gga | cca | gct | cga | ctg | aat | tct | 884 |
| Leu | Gln | Val | His | Thr | Asp | Phe | Gln | Ala | Gly | Pro | Ala | Arg | Leu | Asn | Ser | |
| | | | 250 | | | | | 255 | | | | | 260 | | | |
| ggt | gct | cga | cgt | tcc | ttc | ttc | tgt | cgg | ata | aaa | tgt | agt | agg | acc | aca | 932 |
| Gly | Ala | Arg | Arg | Ser | Phe | Phe | Cys | Arg | Ile | Lys | Cys | Ser | Arg | Thr | Thr | |
| | | | 265 | | | | | 270 | | | | | 275 | | | |
| gtc | aaa | gaa | gag | aag | gag | tgc | tta | ccc | aac | cca | aag | aag | aaa | gat | cac | 980 |
| Val | Lys | Glu | Glu | Lys | Glu | Cys | Leu | Pro | Asn | Pro | Lys | Lys | Lys | Asp | His | |
| | | | 280 | | | | | 285 | | | | | 290 | | | |
| aga | aag | tat | tgt | acc | att | cac | tgt | act | gga | tat | atg | aag | aac | tgg | cct | 1028 |
| Arg | Lys | Tyr | Cys | Thr | Ile | His | Cys | Thr | Gly | Tyr | Met | Lys | Asn | Trp | Pro | |
| | 295 | | | | | 300 | | | | | 305 | | | | | |
| cct | agc | gag | gtg | gga | gtg | gaa | gag | gaa | aac | gat | gta | gaa | aag | aac | agt | 1076 |
| Pro | Ser | Glu | Val | Gly | Val | Glu | Glu | Glu | Asn | Asp | Val | Glu | Lys | Asn | Ser | |
| 310 | | | | | 315 | | | | | 320 | | | | | 325 | |
| agt | aac | ttt | aac | tgt | ctc | gtt | gca | att | ggg | agg | tta | cac | cct | tac | att | 1124 |
| Ser | Asn | Phe | Asn | Cys | Leu | Val | Ala | Ile | Gly | Arg | Leu | His | Pro | Tyr | Ile | |
| | | | 330 | | | | | 335 | | | | | 340 | | | |
| gtt | cca | caa | aag | agt | gga | gag | ata | aaa | gtc | aaa | gca | aca | gaa | ttt | gtt | 1172 |
| Val | Pro | Gln | Lys | Ser | Gly | Glu | Ile | Lys | Val | Lys | Ala | Thr | Glu | Phe | Val | |

```
                    345                 350                 355
aca cga ttt gcc atg gat gga aaa ttt gtt tat gta gat cag cgt gca     1220
Thr Arg Phe Ala Met Asp Gly Lys Phe Val Tyr Val Asp Gln Arg Ala
        360                 365                 370 aca gca att tta ggg tat ctg cca caa gag ctt cta gga act tct tgt     1268
Thr Ala Ile Leu Gly Tyr Leu Pro Gln Glu Leu Leu Gly Thr Ser Cys
    375                 380                 385 tac gag tac tgc cat caa gat gat cac aat cat cta gct gaa aaa cat     1316
Tyr Glu Tyr Cys His Gln Asp Asp His Asn His Leu Ala Glu Lys His
390                 395                 400                 405 aaa gaa gtg ctg cag aat aaa gaa aaa gta ttt aca aat tcc tac aaa     1364
Lys Glu Val Leu Gln Asn Lys Glu Lys Val Phe Thr Asn Ser Tyr Lys
                410                 415                 420 ttt aga gca aaa gat gga agt ttt att act tta aag agt caa tgg ttt     1412
Phe Arg Ala Lys Asp Gly Ser Phe Ile Thr Leu Lys Ser Gln Trp Phe
            425                 430                 435 agt ttc atg aat ccc tgg acc aag gaa ctg gag tac att gta tca aac     1460
Ser Phe Met Asn Pro Trp Thr Lys Glu Leu Glu Tyr Ile Val Ser Asn
        440                 445                 450 aac act gta gta tta ggt cac aat gag tct gct gaa gaa cag gtc tcc     1508
Asn Thr Val Val Leu Gly His Asn Glu Ser Ala Glu Glu Gln Val Ser
    455                 460                 465 tat ggt tcc cag cct gca gaa ggt gct gta aaa cag tct tta gtg agt     1556
Tyr Gly Ser Gln Pro Ala Glu Gly Ala Val Lys Gln Ser Leu Val Ser
470                 475                 480                 485 gta cct gga atg tcc tct gga aca gtt ctt ggt gct gga agt ata gga     1604
Val Pro Gly Met Ser Ser Gly Thr Val Leu Gly Ala Gly Ser Ile Gly
                490                 495                 500 act gaa att gca aat gaa ata tta gaa tta caa agg ttg cat tct tca     1652
Thr Glu Ile Ala Asn Glu Ile Leu Glu Leu Gln Arg Leu His Ser Ser
            505                 510                 515 ccg cct ggg gag tta agt cca tca cat ctc ttg aga aag tca cca tct     1700
Pro Pro Gly Glu Leu Ser Pro Ser His Leu Leu Arg Lys Ser Pro Ser
        520                 525                 530 cca gct tta act gta aac tgc agc aat gtg ccg aat aaa gag ttg att     1748
Pro Ala Leu Thr Val Asn Cys Ser Asn Val Pro Asn Lys Glu Leu Ile
    535                 540                 545 cag tta tgt cct tca gaa gca gaa gtt ctg gag act tca gaa caa aac     1796
Gln Leu Cys Pro Ser Glu Ala Glu Val Leu Glu Thr Ser Glu Gln Asn
550                 555                 560                 565 caa ggt gct att cca ttc ccc agt aat gag cct ctc ctc ggt ggt aat     1844
Gln Gly Ala Ile Pro Phe Pro Ser Asn Glu Pro Leu Leu Gly Gly Asn
                570                 575                 580 tct cag ctg gac ttt gca ata tgt gaa aat gat gac act gcc atg act     1892
Ser Gln Leu Asp Phe Ala Ile Cys Glu Asn Asp Asp Thr Ala Met Thr
            585                 590                 595 gct ctt atg aat tac ttg gag gcc gat gga gga ctt ggg gat cca gct     1940
Ala Leu Met Asn Tyr Leu Glu Ala Asp Gly Gly Leu Gly Asp Pro Ala
        600                 605                 610 gaa ctc agt gac atc caa tgg gct ctc tag                             1970
Glu Leu Ser Asp Ile Gln Trp Ala Leu
    615                 620

<210> SEQ ID NO 10
<211> LENGTH: 622
<212> TYPE: PRT
<213> ORGANISM: Gallus gallus

<400> SEQUENCE: 10

Met Ala Glu Ala Gly Val Gly Ser Ala Glu Gly Ala Glu Glu Glu Arg
```

```
                  1               5              10              15
        Arg Ala Val Glu Glu Asn Phe Pro Val Asp Gly Asn Ser Cys Ile Ala
                        20                  25                  30

Ser Gly Val Pro Ser Leu Met Asn Pro Ile Thr Lys Pro Ala Thr Thr
                        35                  40                  45

Ser Phe Asn Asn Ser Val Val Glu Ile Pro Arg Lys Arg Lys Gly Ser
         50                  55                  60

Asp Ser Asp Asn Gln Asp Thr Val Glu Val Asp Gly Asp Pro Gln Lys
         65                  70                  75                  80

Arg Asn Glu Asp Glu Glu His Leu Lys Ile Lys Asp Phe Arg Glu Ala
                        85                  90                  95

His Ser Gln Thr Glu Lys Arg Arg Asp Lys Met Asn Asn Leu Ile
                        100                 105                 110

Glu Glu Leu Ser Ala Met Ile Pro Gln Cys Asn Pro Met Ala Arg Lys
                        115                 120                 125

Leu Asp Lys Leu Thr Val Leu Arg Met Ala Val Gln His Leu Lys Ser
         130                 135                 140

Leu Lys Gly Ser Thr Ser Ser Tyr Thr Glu Val Arg Tyr Lys Pro Ser
        145                 150                 155                 160

Phe Leu Lys Asp Asp Glu Leu Arg Gln Leu Ile Leu Arg Ala Ala Asp
                        165                 170                 175

Gly Phe Leu Phe Val Val Gly Cys Asn Arg Gly Lys Ile Leu Phe Val
                        180                 185                 190

Ser Glu Ser Val Cys Lys Ile Leu Asn Tyr Asp Gln Thr Ser Leu Ile
                        195                 200                 205

Gly Gln Ser Leu Phe Asp Tyr Leu His Pro Lys Asp Val Ala Lys Val
                        210                 215                 220

Lys Glu Gln Leu Ser Ser Ser Asp Val Ser Pro Arg Glu Lys Leu Val
        225                 230                 235                 240

Asp Gly Lys Thr Gly Leu Gln Val His Thr Asp Phe Gln Ala Gly Pro
                        245                 250                 255

Ala Arg Leu Asn Ser Gly Ala Arg Arg Ser Phe Phe Cys Arg Ile Lys
                        260                 265                 270

Cys Ser Arg Thr Thr Val Lys Glu Glu Lys Glu Cys Leu Pro Asn Pro
                        275                 280                 285

Lys Lys Lys Asp His Arg Lys Tyr Cys Thr Ile His Cys Thr Gly Tyr
                        290                 295                 300

Met Lys Asn Trp Pro Pro Ser Glu Val Gly Val Glu Glu Glu Asn Asp
        305                 310                 315                 320

Val Glu Lys Asn Ser Ser Asn Phe Asn Cys Leu Val Ala Ile Gly Arg
                        325                 330                 335

Leu His Pro Tyr Ile Val Pro Gln Lys Ser Gly Glu Ile Lys Val Lys
                        340                 345                 350

Ala Thr Glu Phe Val Thr Arg Phe Ala Met Asp Gly Lys Phe Val Tyr
                        355                 360                 365

Val Asp Gln Arg Ala Thr Ala Ile Leu Gly Tyr Leu Pro Gln Glu Leu
                        370                 375                 380

Leu Gly Thr Ser Cys Tyr Glu Tyr Cys His Gln Asp Asp His Asn His
        385                 390                 395                 400

Leu Ala Glu Lys His Lys Glu Val Leu Gln Asn Lys Glu Lys Val Phe
                        405                 410                 415

Thr Asn Ser Tyr Lys Phe Arg Ala Lys Asp Gly Ser Phe Ile Thr Leu
                        420                 425                 430
```

-continued

```
Lys Ser Gln Trp Phe Ser Phe Met Asn Pro Trp Thr Lys Glu Leu Glu
            435                 440                 445

Tyr Ile Val Ser Asn Asn Thr Val Val Leu Gly His Asn Glu Ser Ala
        450                 455                 460

Glu Glu Gln Val Ser Tyr Gly Ser Gln Pro Ala Glu Gly Ala Val Lys
465                 470                 475                 480

Gln Ser Leu Val Ser Val Pro Gly Met Ser Gly Thr Val Leu Gly
            485                 490                 495

Ala Gly Ser Ile Gly Thr Glu Ile Ala Asn Glu Ile Leu Glu Leu Gln
        500                 505                 510

Arg Leu His Ser Ser Pro Gly Glu Leu Ser Pro Ser His Leu Leu
            515                 520                 525

Arg Lys Ser Pro Ser Pro Ala Leu Thr Val Asn Cys Ser Asn Val Pro
        530                 535                 540

Asn Lys Glu Leu Ile Gln Leu Cys Pro Ser Glu Ala Glu Val Leu Glu
545                 550                 555                 560

Thr Ser Glu Gln Asn Gln Gly Ala Ile Pro Phe Pro Ser Asn Glu Pro
            565                 570                 575

Leu Leu Gly Gly Asn Ser Gln Leu Asp Phe Ala Ile Cys Glu Asn Asp
            580                 585                 590

Asp Thr Ala Met Thr Ala Leu Met Asn Tyr Leu Glu Ala Asp Gly Gly
            595                 600                 605

Leu Gly Asp Pro Ala Glu Leu Ser Asp Ile Gln Trp Ala Leu
            610                 615                 620
```

<210> SEQ ID NO 11
<211> LENGTH: 1752
<212> TYPE: DNA
<213> ORGANISM: Mus musculus
<220> FEATURE:
<221> NAME/KEY: CDS
<222> LOCATION: (12)..(1748)

<400> SEQUENCE: 11

```
ggtcgaccac c atg gag ttt cca agg aaa cgc aga ggc aga gat tcc cag         50
            Met Glu Phe Pro Arg Lys Arg Arg Gly Arg Asp Ser Gln
              1               5                  10 cca ctc cag tca gaa ttc atg aca gac aca aca gtg gaa agt ctt ccc         98
Pro Leu Gln Ser Glu Phe Met Thr Asp Thr Thr Val Glu Ser Leu Pro
     15                  20                  25 cag aat ccc ttt gcc tct ctt ctt tca aca aga aca gga gta tca gcg        146
Gln Asn Pro Phe Ala Ser Leu Leu Ser Thr Arg Thr Gly Val Ser Ala
 30                  35                  40                  45 ccc agt ggc atc agg gaa gct cac agc cag atg gaa aag cgt cgg aga        194
Pro Ser Gly Ile Arg Glu Ala His Ser Gln Met Glu Lys Arg Arg Arg
                 50                  55                  60 gac aag atg aac cat ctg att cag aaa ctg tca tct atg atc cct cca        242
Asp Lys Met Asn His Leu Ile Gln Lys Leu Ser Ser Met Ile Pro Pro
             65                  70                  75 cac atc ccc acg gcc cac aaa ctg gac aag ctc agc gtc ttg agg agg        290
His Ile Pro Thr Ala His Lys Leu Asp Lys Leu Ser Val Leu Arg Arg
         80                  85                  90 gcg gtg cag tac ttg agg tct ctg aga ggc atg aca gag ctt tac tta        338
Ala Val Gln Tyr Leu Arg Ser Leu Arg Gly Met Thr Glu Leu Tyr Leu
     95                 100                 105 gga gaa aac tct aaa cct tca ttt att cag gat aag gaa ctc agt cac        386
Gly Glu Asn Ser Lys Pro Ser Phe Ile Gln Asp Lys Glu Leu Ser His
110                 115                 120                 125
```

| | | |
|---|---|---|
| tta atc ctc aag gca gca gaa ggc ttc ctg ttt gtg gtt gga tgc gaa<br>Leu Ile Leu Lys Ala Ala Glu Gly Phe Leu Phe Val Val Gly Cys Glu<br>130                       135                   140 | | 434 |
| aga ggg aga att ttt tac gtt tct aag tct gtc tcc aaa aca ctg cgt<br>Arg Gly Arg Ile Phe Tyr Val Ser Lys Ser Val Ser Lys Thr Leu Arg<br>        145                   150                 155 | | 482 |
| tat gat cag gct agc ttg ata gga cag aat ttg ttt gac ttc tta cac<br>Tyr Asp Gln Ala Ser Leu Ile Gly Gln Asn Leu Phe Asp Phe Leu His<br>               160                 165               170 | | 530 |
| cca aaa gac gtc gcc aaa gta aag gaa caa ctt tct tgt gat ggt tca<br>Pro Lys Asp Val Ala Lys Val Lys Glu Gln Leu Ser Cys Asp Gly Ser<br>175                     180                   185 | | 578 |
| cca aga gag aaa cct ata gac acc aaa acc tct cag gtt tac agt cac<br>Pro Arg Glu Lys Pro Ile Asp Thr Lys Thr Ser Gln Val Tyr Ser His<br>190                     195                 200               205 | | 626 |
| ccc tac act ggg cga cca cgc atg cat tct ggc tcc aga cga tct ttc<br>Pro Tyr Thr Gly Arg Pro Arg Met His Ser Gly Ser Arg Arg Ser Phe<br>               210                 215               220 | | 674 |
| ttc ttt aga atg aag agc tgt acc gtc cct gtc aaa gaa gag cag cca<br>Phe Phe Arg Met Lys Ser Cys Thr Val Pro Val Lys Glu Glu Gln Pro<br>        225                   230                 235 | | 722 |
| tgc tcg tcc tgc tca aag aag aaa gac cat aga aaa ttc cac acc gtc<br>Cys Ser Ser Cys Ser Lys Lys Lys Asp His Arg Lys Phe His Thr Val<br>240                     245                   250 | | 770 |
| cat tgc act gga tac ttg aga agc tgg cct ctg aat gtt gtt ggc atg<br>His Cys Thr Gly Tyr Leu Arg Ser Trp Pro Leu Asn Val Val Gly Met<br>               255                 260               265 | | 818 |
| gag aaa gag tcg ggt ggt ggg aag gac agc ggt cct ctt acc tgc ctt<br>Glu Lys Glu Ser Gly Gly Gly Lys Asp Ser Gly Pro Leu Thr Cys Leu<br>270                     275                   280               285 | | 866 |
| gtg gct atg gga cgg ttg cat cca tac att gtc cct caa aag agt ggc<br>Val Ala Met Gly Arg Leu His Pro Tyr Ile Val Pro Gln Lys Ser Gly<br>               290                 295               300 | | 914 |
| aag atc aac gtg aga ccg gct gag ttc ata act cgc ttc gca atg aac<br>Lys Ile Asn Val Arg Pro Ala Glu Phe Ile Thr Arg Phe Ala Met Asn<br>        305                   310                 315 | | 962 |
| ggg aaa ttc gtc tat gtt gac caa agg gca acg gca att tta gga tac<br>Gly Lys Phe Val Tyr Val Asp Gln Arg Ala Thr Ala Ile Leu Gly Tyr<br>320                     325                 330 | | 1010 |
| ctg cct cag gaa ctt ttg gga act tca tgt tat gaa tat ttt cat cag<br>Leu Pro Gln Glu Leu Leu Gly Thr Ser Cys Tyr Glu Tyr Phe His Gln<br>        335                   340                 345 | | 1058 |
| gat gac cac agt agt ttg act gac aag cac aaa gca gtt ctg cag agt<br>Asp Asp His Ser Ser Leu Thr Asp Lys His Lys Ala Val Leu Gln Ser<br>350                     355                   360               365 | | 1106 |
| aag gag aaa ata ctt aca gac tca tac aaa ttc aga gtg aag gat ggt<br>Lys Glu Lys Ile Leu Thr Asp Ser Tyr Lys Phe Arg Val Lys Asp Gly<br>               370                 375               380 | | 1154 |
| gcc ttc gtg act ctg aag agt gag tgg ttc agc ttc aca aac cct tgg<br>Ala Phe Val Thr Leu Lys Ser Glu Trp Phe Ser Phe Thr Asn Pro Trp<br>        385                   390                 395 | | 1202 |
| acc aaa gag ctg gag tac att gtg tct gtc aac aca ttg gtt ttg ggg<br>Thr Lys Glu Leu Glu Tyr Ile Val Ser Val Asn Thr Leu Val Leu Gly<br>400                     405                   410 | | 1250 |
| cgc agt gag acc agg ctg tct ttg ctt cat tgc ggc ggc agc agc cag<br>Arg Ser Glu Thr Arg Leu Ser Leu Leu His Cys Gly Gly Ser Ser Gln<br>        415                   420                 425 | | 1298 |
| tcc tcc gaa gac tca ttt aga caa tcc tgc atc aat gtg ccc ggt gta<br>Ser Ser Glu Asp Ser Phe Arg Gln Ser Cys Ile Asn Val Pro Gly Val | | 1346 |

-continued

```
            430                 435                 440                 445
tcc acg ggg acc gtc ctt ggt gct ggg agt att gga aca gat att gca          1394
Ser Thr Gly Thr Val Leu Gly Ala Gly Ser Ile Gly Thr Asp Ile Ala
                    450                 455                 460 aat gag gtt ctg agt tta cag aga tta cac tct tca tcc cca gaa gat          1442
Asn Glu Val Leu Ser Leu Gln Arg Leu His Ser Ser Ser Pro Glu Asp
            465                 470                 475 gca agc cct tca gaa gaa gtg aga gat gac tgc agt gta aat ggt ggg          1490
Ala Ser Pro Ser Glu Glu Val Arg Asp Asp Cys Ser Val Asn Gly Gly
        480                 485                 490 aat gcc tat ggg cct gca tcc act agg gag cct ttt gca gtg agc cct          1538
Asn Ala Tyr Gly Pro Ala Ser Thr Arg Glu Pro Phe Ala Val Ser Pro
    495                 500                 505 tct gaa aca gag gtc ctg gag gct gcc agg caa cac cag agc act gaa          1586
Ser Glu Thr Glu Val Leu Glu Ala Ala Arg Gln His Gln Ser Thr Glu
510                 515                 520                 525 ccc gcc cac cct cac gga cca ctt ccc ggt gac agt gcc cag ctg ggt          1634
Pro Ala His Pro His Gly Pro Leu Pro Gly Asp Ser Ala Gln Leu Gly
                    530                 535                 540 ttt gat gtc ctg tgt gac agt gac agc ata gac atg gct gca ttc atg          1682
Phe Asp Val Leu Cys Asp Ser Asp Ser Ile Asp Met Ala Ala Phe Met
            545                 550                 555 aat tac ctc gaa gca gag ggg ggc ctg ggt gac cct ggg gac ttc agt          1730
Asn Tyr Leu Glu Ala Glu Gly Gly Leu Gly Asp Pro Gly Asp Phe Ser
        560                 565                 570 gac atc cag tgg gca ctc tagc                                             1752
Asp Ile Gln Trp Ala Leu
    575

<210> SEQ ID NO 12
<211> LENGTH: 579
<212> TYPE: PRT
<213> ORGANISM: Mus musculus

<400> SEQUENCE: 12

Met Glu Phe Pro Arg Lys Arg Gly Arg Asp Ser Gln Pro Leu Gln
1               5                   10                  15

Ser Glu Phe Met Thr Asp Thr Thr Val Glu Ser Leu Pro Gln Asn Pro
            20                  25                  30

Phe Ala Ser Leu Leu Ser Thr Arg Thr Gly Val Ser Ala Pro Ser Gly
        35                  40                  45

Ile Arg Glu Ala His Ser Gln Met Glu Lys Arg Arg Asp Lys Met
    50                  55                  60

Asn His Leu Ile Gln Lys Leu Ser Ser Met Ile Pro Pro His Ile Pro
65                  70                  75                  80

Thr Ala His Lys Leu Asp Lys Leu Ser Val Leu Arg Arg Ala Val Gln
                85                  90                  95

Tyr Leu Arg Ser Leu Arg Gly Met Thr Glu Leu Tyr Leu Gly Glu Asn
            100                 105                 110

Ser Lys Pro Ser Phe Ile Gln Asp Lys Glu Leu Ser His Leu Ile Leu
        115                 120                 125

Lys Ala Ala Glu Gly Phe Leu Phe Val Val Gly Cys Glu Arg Gly Arg
    130                 135                 140

Ile Phe Tyr Val Ser Lys Ser Val Ser Lys Thr Leu Arg Tyr Asp Gln
145                 150                 155                 160

Ala Ser Leu Ile Gly Gln Asn Leu Phe Asp Phe Leu His Pro Lys Asp
                165                 170                 175
```

-continued

```
Val Ala Lys Val Lys Glu Gln Leu Ser Cys Asp Gly Ser Pro Arg Glu
            180                 185                 190

Lys Pro Ile Asp Thr Lys Thr Ser Gln Val Tyr Ser His Pro Tyr Thr
        195                 200                 205

Gly Arg Pro Arg Met His Ser Gly Ser Arg Arg Ser Phe Phe Phe Arg
    210                 215                 220

Met Lys Ser Cys Thr Val Pro Val Lys Glu Glu Gln Pro Cys Ser Ser
225                 230                 235                 240

Cys Ser Lys Lys Lys Asp His Arg Lys Phe His Thr Val His Cys Thr
                245                 250                 255

Gly Tyr Leu Arg Ser Trp Pro Leu Asn Val Val Gly Met Glu Lys Glu
            260                 265                 270

Ser Gly Gly Gly Lys Asp Ser Gly Pro Leu Thr Cys Leu Val Ala Met
            275                 280                 285

Gly Arg Leu His Pro Tyr Ile Val Pro Gln Lys Ser Gly Lys Ile Asn
    290                 295                 300

Val Arg Pro Ala Glu Phe Ile Thr Arg Phe Ala Met Asn Gly Lys Phe
305                 310                 315                 320

Val Tyr Val Asp Gln Arg Ala Thr Ala Ile Leu Gly Tyr Leu Pro Gln
                325                 330                 335

Glu Leu Leu Gly Thr Ser Cys Tyr Glu Tyr Phe His Gln Asp Asp His
            340                 345                 350

Ser Ser Leu Thr Asp Lys His Lys Ala Val Leu Gln Ser Lys Glu Lys
        355                 360                 365

Ile Leu Thr Asp Ser Tyr Lys Phe Arg Val Lys Asp Gly Ala Phe Val
    370                 375                 380

Thr Leu Lys Ser Glu Trp Phe Ser Phe Thr Asn Pro Trp Thr Lys Glu
385                 390                 395                 400

Leu Glu Tyr Ile Val Ser Val Asn Thr Leu Val Leu Gly Arg Ser Glu
                405                 410                 415

Thr Arg Leu Ser Leu Leu His Cys Gly Gly Ser Ser Gln Ser Ser Glu
            420                 425                 430

Asp Ser Phe Arg Gln Ser Cys Ile Asn Val Pro Gly Val Ser Thr Gly
        435                 440                 445

Thr Val Leu Gly Ala Gly Ser Ile Gly Thr Asp Ile Ala Asn Glu Val
    450                 455                 460

Leu Ser Leu Gln Arg Leu His Ser Ser Pro Glu Asp Ala Ser Pro
465                 470                 475                 480

Ser Glu Glu Val Arg Asp Cys Ser Val Asn Gly Gly Asn Ala Tyr
                485                 490                 495

Gly Pro Ala Ser Thr Arg Glu Pro Phe Ala Val Ser Pro Ser Glu Thr
            500                 505                 510

Glu Val Leu Glu Ala Ala Arg Gln His Gln Ser Thr Glu Pro Ala His
        515                 520                 525

Pro His Gly Pro Leu Pro Gly Asp Ser Ala Gln Leu Gly Phe Asp Val
    530                 535                 540

Leu Cys Asp Ser Asp Ser Ile Asp Met Ala Ala Phe Met Asn Tyr Leu
545                 550                 555                 560

Glu Ala Glu Gly Gly Leu Gly Asp Pro Gly Asp Phe Ser Asp Ile Gln
                565                 570                 575

Trp Ala Leu
```

<210> SEQ ID NO 13

-continued

```
<211> LENGTH: 1676
<212> TYPE: DNA
<213> ORGANISM: Mus musculus
<220> FEATURE:
<221> NAME/KEY: CDS
<222> LOCATION: (12)..(608)

<400> SEQUENCE: 13
```

| | | |
|---|---|---|
| ggtcgaccac c atg gag ttt cca agg aaa cgc aga ggc aga gat tcc cag<br>     Met Glu Phe Pro Arg Lys Arg Arg Gly Arg Asp Ser Gln<br>      1               5                  10 | | 50 |
| cca ctc cag tca gaa ttc atg aca gac aca aca gtg gaa agt ctt ccc<br>Pro Leu Gln Ser Glu Phe Met Thr Asp Thr Thr Val Glu Ser Leu Pro<br>     15                  20                  25 | | 98 |
| cag aat ccc ttt gcc tct ctt ctt tca aca aga aca gga gta tca gcg<br>Gln Asn Pro Phe Ala Ser Leu Leu Ser Thr Arg Thr Gly Val Ser Ala<br> 30                  35                  40                  45 | | 146 |
| ccc agt ggc atc agg gaa gct cac agc cag atg gaa aag cgt cgg aga<br>Pro Ser Gly Ile Arg Glu Ala His Ser Gln Met Glu Lys Arg Arg Arg<br>                 50                  55                  60 | | 194 |
| gac aag atg aac cat ctg att cag aaa ctg tca tct atg atc cct cca<br>Asp Lys Met Asn His Leu Ile Gln Lys Leu Ser Ser Met Ile Pro Pro<br>             65                  70                  75 | | 242 |
| cac atc ccc acg gcc cac aaa ctg gac aag ctc agc gtc ttg agg agg<br>His Ile Pro Thr Ala His Lys Leu Asp Lys Leu Ser Val Leu Arg Arg<br>         80                  85                  90 | | 290 |
| gcg gtg cag tac ttg agg tct ctg aga ggc atg aca gag ctt tac tta<br>Ala Val Gln Tyr Leu Arg Ser Leu Arg Gly Met Thr Glu Leu Tyr Leu<br>     95                 100                 105 | | 338 |
| gga gaa aac tct aaa cct tca ttt att cag gat aag gaa ctc agt cac<br>Gly Glu Asn Ser Lys Pro Ser Phe Ile Gln Asp Lys Glu Leu Ser His<br>110                 115                 120                 125 | | 386 |
| tta atc ctc aag gca gca gaa ggc ttc ctg ttt gtg gtt gga tgc gaa<br>Leu Ile Leu Lys Ala Ala Glu Gly Phe Leu Phe Val Val Gly Cys Glu<br>                130                 135                 140 | | 434 |
| aga ggg aga att ttt tac gtt tct aag tct gtc tcc aaa aca ctg cgt<br>Arg Gly Arg Ile Phe Tyr Val Ser Lys Ser Val Ser Lys Thr Leu Arg<br>            145                 150                 155 | | 482 |
| tat gat cag gct agc ttg ata gga cag aat ttg ttt gac ttc tta cac<br>Tyr Asp Gln Ala Ser Leu Ile Gly Gln Asn Leu Phe Asp Phe Leu His<br>        160                 165                 170 | | 530 |
| cca aaa gac gtc gcc aaa gta aag gaa caa ctt tct tgt gat ggt tca<br>Pro Lys Asp Val Ala Lys Val Lys Glu Gln Leu Ser Cys Asp Gly Ser<br>    175                 180                 185 | | 578 |
| cca aga gag aaa cct ata gac acc aaa aaa tgaagagctg taccgtccct<br>Pro Arg Glu Lys Pro Ile Asp Thr Lys Lys<br>190                 195 | | 628 |
| gtcaaagaag agcagccatg ctcgtcctgc tcaaagaaga aagaccatag aaaattccac | | 688 |
| accgtccatt gcactggata cttgagaagc tggcctctga atgttgttgg catggagaaa | | 748 |
| gagtcgggtg gtgggaagga cagcggtcct cttacctgcc ttgtggctat gggacggttg | | 808 |
| catccataca ttgtccctca aaagagtggc aagatcaacg tgagaccggc tgagttcata | | 868 |
| actcgcttcg caatgaacgg gaaattcgtc tatgttgacc aaagggcaac ggcaattta | | 928 |
| ggatacctgc ctcaggaact tttgggaact tcatgttatg aatattttca tcaggatgac | | 988 |
| cacagtagtt tgactgacaa gcacaaagca gttctgcaga gtaaggagaa atacttaca | | 1048 |
| gactcataca aattcagagt gaaggatggt gccttcgtga ctctgaagag tgagtggttc | | 1108 |
| agcttcacaa acccttggac caaagagctg gagtacattg tgtctgtcaa cacattggtt | | 1168 |

| ttgggcgca gtgagaccag gctgtctttg cttcattgcg gcggcagcag ccagtcctcc | 1228 |
| gaagactcat ttagacaatc ctgcatcaat gtgcccggtg tatccacggg gaccgtcctt | 1288 |
| ggtgctggga gtattggaac agatattgca aatgaggttc tgagtttaca gagattacac | 1348 |
| tcttcatccc cagaagatgc aagcccttca gaagaagtga gagatgactg cagtgtaaat | 1408 |
| ggtgggaatg cctatgggcc tgcatccact agggagcctt ttgcagtgag cccttctgaa | 1468 |
| acagaggtcc tggaggctgc caggcaacac cagagcactg aacccgccca ccctcacgga | 1528 |
| ccacttcccg gtgacagtgc ccagctgggt tttgatgtcc tgtgtgacag tgacagcata | 1588 |
| gacatggctg cattcatgaa ttacctcgaa gcagaggggg gcctgggtga ccctggggac | 1648 |
| ttcagtgaca tccagtgggc actctagc | 1676 |

<210> SEQ ID NO 14
<211> LENGTH: 199
<212> TYPE: PRT
<213> ORGANISM: Mus musculus

<400> SEQUENCE: 14

```
Met Glu Phe Pro Arg Lys Arg Arg Gly Arg Asp Ser Gln Pro Leu Gln
 1               5                  10                  15

Ser Glu Phe Met Thr Asp Thr Thr Val Glu Ser Leu Pro Gln Asn Pro
             20                  25                  30

Phe Ala Ser Leu Leu Ser Thr Arg Thr Gly Val Ser Ala Pro Ser Gly
         35                  40                  45

Ile Arg Glu Ala His Ser Gln Met Glu Lys Arg Arg Asp Lys Met
     50                  55                  60

Asn His Leu Ile Gln Lys Leu Ser Ser Met Ile Pro Pro His Ile Pro
 65                  70                  75                  80

Thr Ala His Lys Leu Asp Lys Leu Ser Val Leu Arg Arg Ala Val Gln
                 85                  90                  95

Tyr Leu Arg Ser Leu Arg Gly Met Thr Glu Leu Tyr Leu Gly Glu Asn
            100                 105                 110

Ser Lys Pro Ser Phe Ile Gln Asp Lys Glu Leu Ser His Leu Ile Leu
        115                 120                 125

Lys Ala Ala Glu Gly Phe Leu Phe Val Val Gly Cys Glu Arg Gly Arg
    130                 135                 140

Ile Phe Tyr Val Ser Lys Ser Val Ser Lys Thr Leu Arg Tyr Asp Gln
145                 150                 155                 160

Ala Ser Leu Ile Gly Gln Asn Leu Phe Asp Phe Leu His Pro Lys Asp
                165                 170                 175

Val Ala Lys Val Lys Glu Gln Leu Ser Cys Asp Gly Ser Pro Arg Glu
            180                 185                 190

Lys Pro Ile Asp Thr Lys Lys
        195
```

<210> SEQ ID NO 15
<211> LENGTH: 1748
<212> TYPE: DNA
<213> ORGANISM: Rattus norvegicus
<220> FEATURE:
<221> NAME/KEY: CDS
<222> LOCATION: (33)..(1745)

<400> SEQUENCE: 15

| tcacagctcc tggacctgtc agctctcttg ca atg gag ttg cca agg aaa cgt | 53 |
|  | Met Glu Leu Pro Arg Lys Arg |
|  | 1               5 |

-continued

```
aga aga agt gat tca gag ctg ctc cag tca gaa ttc agg aca gat gca      101
Arg Arg Ser Asp Ser Glu Leu Leu Gln Ser Glu Phe Arg Thr Asp Ala
         10                  15                  20 atg gtg gaa aac ctt ccc cgg agt ccc ttt acc tct gtt ctt tca aca      149
Met Val Glu Asn Leu Pro Arg Ser Pro Phe Thr Ser Val Leu Ser Thr
     25                  30                  35 aga aca gga gta gca gtg ccc aat ggc atc agg gaa gct cac agc cag      197
Arg Thr Gly Val Ala Val Pro Asn Gly Ile Arg Glu Ala His Ser Gln
 40                  45                  50                  55 aca gaa aag cgt cgg aga gac aag atg aac cat ctg att tgg aaa ctg      245
Thr Glu Lys Arg Arg Arg Asp Lys Met Asn His Leu Ile Trp Lys Leu
                 60                  65                  70 tca tct atg atc cct cca cac atc ccc aca gcc cac aaa ctg gac aaa      293
Ser Ser Met Ile Pro Pro His Ile Pro Thr Ala His Lys Leu Asp Lys
             75                  80                  85 ctg agc gtc ctg agg agg gca gtg cag tac ttg agg tct cag aga ggc      341
Leu Ser Val Leu Arg Arg Ala Val Gln Tyr Leu Arg Ser Gln Arg Gly
         90                  95                 100 atg aca gag ttt tat tta gga gaa aat gct aaa cct tca ttt att cag      389
Met Thr Glu Phe Tyr Leu Gly Glu Asn Ala Lys Pro Ser Phe Ile Gln
    105                 110                 115 gat aag gaa ctc agc cac tta atc ctc aag gca gca gaa ggc ttc cta      437
Asp Lys Glu Leu Ser His Leu Ile Leu Lys Ala Ala Glu Gly Phe Leu
120                 125                 130                 135 ctt gtg gtt gga tgt gaa gga ggg aga att ctt ttc gtt tct aag tct      485
Leu Val Val Gly Cys Glu Gly Gly Arg Ile Leu Phe Val Ser Lys Ser
                140                 145                 150 gtc tcc aaa acg ctg cat tat gat cag gct agt ttg atg gga cag aac      533
Val Ser Lys Thr Leu His Tyr Asp Gln Ala Ser Leu Met Gly Gln Asn
            155                 160                 165 ttg ttt gac ttc tta cac cca aaa gat gtc gcc aaa gta aag gaa caa      581
Leu Phe Asp Phe Leu His Pro Lys Asp Val Ala Lys Val Lys Glu Gln
        170                 175                 180 ctt tct tgt gat gtt tca ctg aga gag aaa ccc ata ggc acc aaa acc      629
Leu Ser Cys Asp Val Ser Leu Arg Glu Lys Pro Ile Gly Thr Lys Thr
    185                 190                 195 tct cct cag gtt cac agt cac tcc cat att ggg cga tca cgc gtg cat      677
Ser Pro Gln Val His Ser His Ser His Ile Gly Arg Ser Arg Val His
200                 205                 210                 215 tct ggc tcc aga cga tct ttc ttc ttt aga atg aag agc agc tgt aca      725
Ser Gly Ser Arg Arg Ser Phe Phe Phe Arg Met Lys Ser Ser Cys Thr
                220                 225                 230 gtc ccc gtc aaa gaa gag caa cga tgc tcg tcc tgt tca aag aag aaa      773
Val Pro Val Lys Glu Glu Gln Arg Cys Ser Ser Cys Ser Lys Lys Lys
            235                 240                 245 gac cag aga aaa ttc cac acc atc cat tgc act gga tac ttg aga agc      821
Asp Gln Arg Lys Phe His Thr Ile His Cys Thr Gly Tyr Leu Arg Ser
        250                 255                 260 tgg cca ccg aat gtt gtg ggc acg gag aaa gag atg ggc agt ggg aaa      869
Trp Pro Pro Asn Val Val Gly Thr Glu Lys Glu Met Gly Ser Gly Lys
    265                 270                 275 gac agt ggt cct ctt acc tgc ctt gtg gct atg gga cgg tta cag cca      917
Asp Ser Gly Pro Leu Thr Cys Leu Val Ala Met Gly Arg Leu Gln Pro
280                 285                 290                 295 tat act gtc ccc ccg aag aat ggc aag atc aac gtg aga ccg gct gag      965
Tyr Thr Val Pro Pro Lys Asn Gly Lys Ile Asn Val Arg Pro Ala Glu
                300                 305                 310 ttc ata acc cga ttc gca atg aac ggg aaa ttc gtc tac gtc gac caa     1013
Phe Ile Thr Arg Phe Ala Met Asn Gly Lys Phe Val Tyr Val Asp Gln
```

```
agg gca aca gca att tta gga tac ctg cct cag gaa ctt ttg gga act    1061
Arg Ala Thr Ala Ile Leu Gly Tyr Leu Pro Gln Glu Leu Leu Gly Thr
        330                 335                 340 tcg tgt tat gaa tat ttt cat cag gat gac cac agt aat ttg agt gac    1109
Ser Cys Tyr Glu Tyr Phe His Gln Asp Asp His Ser Asn Leu Ser Asp
345                 350                 355 aag cac aaa gca gtt ctg cag agt aag gag aaa ata ctt aca gat tca    1157
Lys His Lys Ala Val Leu Gln Ser Lys Glu Lys Ile Leu Thr Asp Ser
360                 365                 370                 375 tac aaa ttc aga gtg aag gat ggc tcc ttt gtg act ctg aag agc aag    1205
Tyr Lys Phe Arg Val Lys Asp Gly Ser Phe Val Thr Leu Lys Ser Lys
                380                 385                 390 tgg ttc agc ttc act aac cct tgg acc aaa aag ctg gag tac atc gtg    1253
Trp Phe Ser Phe Thr Asn Pro Trp Thr Lys Lys Leu Glu Tyr Ile Val
            395                 400                 405 tct gtc aac acg ctg gtt ttg ggg cgc agt gag acc gca gta tcc gtg    1301
Ser Val Asn Thr Leu Val Leu Gly Arg Ser Glu Thr Ala Val Ser Val
        410                 415                 420 cct cag tgc cgc agc agc cag tcc tct gaa gac tca ttt aga caa ccc    1349
Pro Gln Cys Arg Ser Ser Gln Ser Ser Glu Asp Ser Phe Arg Gln Pro
    425                 430                 435 tgc gtc agt gtg ccg ggc ata tcc aca ggg acc tta ctt ggc act ggg    1397
Cys Val Ser Val Pro Gly Ile Ser Thr Gly Thr Leu Leu Gly Thr Gly
440                 445                 450                 455 agt att gga aca gat att gca aat gag gtt ctg agt tta cag agg tca    1445
Ser Ile Gly Thr Asp Ile Ala Asn Glu Val Leu Ser Leu Gln Arg Ser
                460                 465                 470 cac tct tca tcc cca gaa gac gca aac cct tca gga gta gtg aga gat    1493
His Ser Ser Ser Pro Glu Asp Ala Asn Pro Ser Gly Val Val Arg Asp
            475                 480                 485 aag cac agt gta aac ttc ggg agc gcc cct gtg ccc gtg tcc act ggg    1541
Lys His Ser Val Asn Phe Gly Ser Ala Pro Val Pro Val Ser Thr Gly
        490                 495                 500 gag ctc ttt gca ctg agt cct gaa aca gag ggc ctg gag gct gcc agg    1589
Glu Leu Phe Ala Leu Ser Pro Glu Thr Glu Gly Leu Glu Ala Ala Arg
    505                 510                 515 caa cac cag agt tct gag ccc gcc cac tgt cac aaa cca ctc ctc agt    1637
Gln His Gln Ser Ser Glu Pro Ala His Cys His Lys Pro Leu Leu Ser
520                 525                 530                 535 gac agt acc cag ttg ggt ttt gat gcc ctg tgt gac agc gac gac aca    1685
Asp Ser Thr Gln Leu Gly Phe Asp Ala Leu Cys Asp Ser Asp Asp Thr
                540                 545                 550 gcc atg gct aca ttc atg aat tac ctc gaa gca gag ggt ggc ctg ggt    1733
Ala Met Ala Thr Phe Met Asn Tyr Leu Glu Ala Glu Gly Gly Leu Gly
            555                 560                 565 gac cct ggg gac ttc                                                1748
Asp Pro Gly Asp
        570

<210> SEQ ID NO 16
<211> LENGTH: 571
<212> TYPE: PRT
<213> ORGANISM: Rattus norvegicus

<400> SEQUENCE: 16

Met Glu Leu Pro Arg Lys Arg Arg Ser Asp Ser Glu Leu Leu Gln
1               5                   10                  15

Ser Glu Phe Arg Thr Asp Ala Met Val Glu Asn Leu Pro Arg Ser Pro
            20                  25                  30
```

```
Phe Thr Ser Val Leu Ser Thr Arg Thr Gly Val Ala Val Pro Asn Gly
        35                  40                  45

Ile Arg Glu Ala His Ser Gln Thr Glu Lys Arg Arg Arg Asp Lys Met
 50                  55                  60

Asn His Leu Ile Trp Lys Leu Ser Ser Met Ile Pro Pro His Ile Pro
 65                  70                  75                  80

Thr Ala His Lys Leu Asp Lys Leu Ser Val Leu Arg Arg Ala Val Gln
                 85                  90                  95

Tyr Leu Arg Ser Gln Arg Gly Met Thr Glu Phe Tyr Leu Gly Glu Asn
            100                 105                 110

Ala Lys Pro Ser Phe Ile Gln Asp Lys Glu Leu Ser His Leu Ile Leu
        115                 120                 125

Lys Ala Ala Glu Gly Phe Leu Leu Val Val Gly Cys Glu Gly Gly Arg
    130                 135                 140

Ile Leu Phe Val Ser Lys Ser Val Ser Lys Thr Leu His Tyr Asp Gln
145                 150                 155                 160

Ala Ser Leu Met Gly Gln Asn Leu Phe Asp Phe Leu His Pro Lys Asp
                165                 170                 175

Val Ala Lys Val Lys Glu Gln Leu Ser Cys Asp Val Ser Leu Arg Glu
            180                 185                 190

Lys Pro Ile Gly Thr Lys Thr Ser Pro Gln Val His Ser His Ser His
        195                 200                 205

Ile Gly Arg Ser Arg Val His Ser Gly Ser Arg Arg Ser Phe Phe Phe
    210                 215                 220

Arg Met Lys Ser Ser Cys Thr Val Pro Val Lys Glu Glu Gln Arg Cys
225                 230                 235                 240

Ser Ser Cys Ser Lys Lys Asp Gln Arg Lys Phe His Thr Ile His
                245                 250                 255

Cys Thr Gly Tyr Leu Arg Ser Trp Pro Pro Asn Val Val Gly Thr Glu
            260                 265                 270

Lys Glu Met Gly Ser Gly Lys Asp Ser Gly Pro Leu Thr Cys Leu Val
        275                 280                 285

Ala Met Gly Arg Leu Gln Pro Tyr Thr Val Pro Pro Lys Asn Gly Lys
    290                 295                 300

Ile Asn Val Arg Pro Ala Glu Phe Ile Thr Arg Phe Ala Met Asn Gly
305                 310                 315                 320

Lys Phe Val Tyr Val Asp Gln Arg Ala Thr Ala Ile Leu Gly Tyr Leu
                325                 330                 335

Pro Gln Glu Leu Leu Gly Thr Ser Cys Tyr Glu Tyr Phe His Gln Asp
            340                 345                 350

Asp His Ser Asn Leu Ser Asp Lys His Lys Ala Val Leu Gln Ser Lys
        355                 360                 365

Glu Lys Ile Leu Thr Asp Ser Tyr Lys Phe Arg Val Lys Asp Gly Ser
    370                 375                 380

Phe Val Thr Leu Lys Ser Lys Trp Phe Ser Phe Thr Asn Pro Trp Thr
385                 390                 395                 400

Lys Lys Leu Glu Tyr Ile Val Ser Val Asn Thr Val Leu Gly Arg
                405                 410                 415

Ser Glu Thr Ala Val Ser Val Pro Gln Cys Arg Ser Ser Gln Ser Ser
            420                 425                 430

Glu Asp Ser Phe Arg Gln Pro Cys Val Ser Val Pro Gly Ile Ser Thr
        435                 440                 445
```

```
Gly Thr Leu Leu Gly Thr Gly Ser Ile Gly Thr Asp Ile Ala Asn Glu
    450                 455                 460

Val Leu Ser Leu Gln Arg Ser His Ser Ser Pro Glu Asp Ala Asn
465                 470                 475                 480

Pro Ser Gly Val Val Arg Asp Lys His Ser Val Asn Phe Gly Ser Ala
                485                 490                 495

Pro Val Pro Val Ser Thr Gly Glu Leu Phe Ala Leu Ser Pro Glu Thr
            500                 505                 510

Glu Gly Leu Glu Ala Ala Arg Gln His Gln Ser Ser Glu Pro Ala His
        515                 520                 525

Cys His Lys Pro Leu Leu Ser Asp Ser Thr Gln Leu Gly Phe Asp Ala
    530                 535                 540

Leu Cys Asp Ser Asp Asp Thr Ala Met Ala Thr Phe Met Asn Tyr Leu
545                 550                 555                 560

Glu Ala Glu Gly Gly Leu Gly Asp Pro Gly Asp
                565                 570
```

<210> SEQ ID NO 17
<211> LENGTH: 1646
<212> TYPE: DNA
<213> ORGANISM: Rattus norvegicus
<220> FEATURE:
<221> NAME/KEY: CDS
<222> LOCATION: (33)..(1646)

<400> SEQUENCE: 17

```
tcacagctcc tggacctgtc agctctcttg ca atg gag ttg cca agg aaa cgt        53
                                   Met Glu Leu Pro Arg Lys Arg
                                    1               5 aga aga agt gat tca gag ctg ctc cag gaa gct cac agc cag aca gaa      101
Arg Arg Ser Asp Ser Glu Leu Leu Gln Glu Ala His Ser Gln Thr Glu
           10                  15                  20 aag cgt cgg aga gac aag atg aac cat ctg att tgg aaa ctg tca tct      149
Lys Arg Arg Arg Asp Lys Met Asn His Leu Ile Trp Lys Leu Ser Ser
 25                  30                  35 atg atc cct cca cac atc ccc aca gcc cac aaa ctg gac aaa ctg agc      197
Met Ile Pro Pro His Ile Pro Thr Ala His Lys Leu Asp Lys Leu Ser
 40                  45                  50                  55 gtc ctg agg agg gca gtg cag tac ttg agg tct cag aga ggc atg aca      245
Val Leu Arg Arg Ala Val Gln Tyr Leu Arg Ser Gln Arg Gly Met Thr
                 60                  65                  70 gag ttt tat tta gga gaa aat gct aaa cct tca ttt att cag gat aag      293
Glu Phe Tyr Leu Gly Glu Asn Ala Lys Pro Ser Phe Ile Gln Asp Lys
             75                  80                  85 gaa ctc agc cac tta atc ctc aag gca gca gaa ggc ttc cta ctt gtg      341
Glu Leu Ser His Leu Ile Leu Lys Ala Ala Glu Gly Phe Leu Leu Val
         90                  95                 100 gtt gga tgt gaa gga ggg aga att ctt ttc gtt tct aag tct gtc tcc      389
Val Gly Cys Glu Gly Gly Arg Ile Leu Phe Val Ser Lys Ser Val Ser
     105                 110                 115 aaa acg ctg cat tat gat cag gct agt ttg atg gga cag aac ttg ttt      437
Lys Thr Leu His Tyr Asp Gln Ala Ser Leu Met Gly Gln Asn Leu Phe
120                 125                 130                 135 gac ttc tta cac cca aaa gat gtc gcc aaa gta aag gaa caa ctt tct      485
Asp Phe Leu His Pro Lys Asp Val Ala Lys Val Lys Glu Gln Leu Ser
                140                 145                 150 tgt gat gtt tca ctg aga gag aaa ccc ata ggc acc aaa acc tct cct      533
Cys Asp Val Ser Leu Arg Glu Lys Pro Ile Gly Thr Lys Thr Ser Pro
            155                 160                 165
```

-continued

| | |
|---|---|
| cag gtt cac agt cac tcc cat att ggg cga tca cgc gtg cat tct ggc<br>Gln Val His Ser His Ser His Ile Gly Arg Ser Arg Val His Ser Gly<br>     170                  175                  180 | 581 |
| tcc aga cga tct ttc ttc ttt aga atg aag agc agc tgt aca gtc ccc<br>Ser Arg Arg Ser Phe Phe Phe Arg Met Lys Ser Ser Cys Thr Val Pro<br>185                   190                  195 | 629 |
| gtc aaa gaa gag caa cga tgc tcg tcc tgt tca aag aag aaa gac cag<br>Val Lys Glu Glu Gln Arg Cys Ser Ser Cys Ser Lys Lys Lys Asp Gln<br>200                 205                 210                215 | 677 |
| aga aaa ttc cac acc atc cat tgc act gga tac ttg aga agc tgg cca<br>Arg Lys Phe His Thr Ile His Cys Thr Gly Tyr Leu Arg Ser Trp Pro<br>                  220                  225                  230 | 725 |
| ccg aat gtt gtg ggc acg gag aaa gag atg ggc agt ggg aaa gac agt<br>Pro Asn Val Val Gly Thr Glu Lys Glu Met Gly Ser Gly Lys Asp Ser<br>                  235                  240                  245 | 773 |
| ggt cct ctt acc tgc ctt gtg gct atg gga cgg tta cag cca tat act<br>Gly Pro Leu Thr Cys Leu Val Ala Met Gly Arg Leu Gln Pro Tyr Thr<br>         250                  255                  260 | 821 |
| gtc ccc ccg aag aat ggc aag atc aac gtg aga ccg gct gag ttc ata<br>Val Pro Pro Lys Asn Gly Lys Ile Asn Val Arg Pro Ala Glu Phe Ile<br>265                   270                  275 | 869 |
| acc cga ttc gca atg aac ggg aaa ttc gtc tac gtc gac caa agg gca<br>Thr Arg Phe Ala Met Asn Gly Lys Phe Val Tyr Val Asp Gln Arg Ala<br>280                   285                  290                295 | 917 |
| aca gca att tta gga tac ctg cct cag gaa ctt ttg gga act tcg tgt<br>Thr Ala Ile Leu Gly Tyr Leu Pro Gln Glu Leu Leu Gly Thr Ser Cys<br>                  300                  305                  310 | 965 |
| tat gaa tat ttt cat cag gat gac cac agt aat ttg agt gac aag cac<br>Tyr Glu Tyr Phe His Gln Asp Asp His Ser Asn Leu Ser Asp Lys His<br>                  315                  320                  325 | 1013 |
| aaa gca gtt ctg cag agt aag gag aaa ata ctt aca gat tca tac aaa<br>Lys Ala Val Leu Gln Ser Lys Glu Lys Ile Leu Thr Asp Ser Tyr Lys<br>                  330                  335                  340 | 1061 |
| ttc aga gtg aag gat ggc tcc ttt gtg act ctg aag agc aag tgg ttc<br>Phe Arg Val Lys Asp Gly Ser Phe Val Thr Leu Lys Ser Lys Trp Phe<br>345                   350                  355 | 1109 |
| agc ttc act aac cct tgg acc aaa aag ctg gag tac atc gtg tct gtc<br>Ser Phe Thr Asn Pro Trp Thr Lys Lys Leu Glu Tyr Ile Val Ser Val<br>360                   365                  370                375 | 1157 |
| aac acg ctg gtt ttg ggg cgc agt gag acc gca gta tcc gtg cct cag<br>Asn Thr Leu Val Leu Gly Arg Ser Glu Thr Ala Val Ser Val Pro Gln<br>                  380                  385                  390 | 1205 |
| tgc cgc agc agc cag tcc tct gaa gac tca ttt aga caa ccc tgc gtc<br>Cys Arg Ser Ser Gln Ser Ser Glu Asp Ser Phe Arg Gln Pro Cys Val<br>395                   400                  405 | 1253 |
| agt gtg ccg ggc ata tcc aca ggg acc tta ctt ggc act ggg agt att<br>Ser Val Pro Gly Ile Ser Thr Gly Thr Leu Leu Gly Thr Gly Ser Ile<br>         410                  415                  420 | 1301 |
| gga aca gat att gca aat gag gtt ctg agt tta cag agg tca cac tct<br>Gly Thr Asp Ile Ala Asn Glu Val Leu Ser Leu Gln Arg Ser His Ser<br>425                   430                  435 | 1349 |
| tca tcc cca gaa gac gca aac cct tca gga gta gtg aga gat aag cac<br>Ser Ser Pro Glu Asp Ala Asn Pro Ser Gly Val Val Arg Asp Lys His<br>440                   445                  450                455 | 1397 |
| agt gta aac ttc ggg agc gcc cct gtg ccc gtg tcc act ggg gag ctc<br>Ser Val Asn Phe Gly Ser Ala Pro Val Pro Val Ser Thr Gly Glu Leu<br>                  460                  465                  470 | 1445 |
| ttt gca ctg agt cct gaa aca gag ggc ctg gag gct gcc agg caa cac<br>Phe Ala Leu Ser Pro Glu Thr Glu Gly Leu Glu Ala Ala Arg Gln His<br>                  475                  480                485 | 1493 |

```
cag agt tct gag ccc gcc cac tgt cac aaa cca ctc ctc agt gac agt      1541
Gln Ser Ser Glu Pro Ala His Cys His Lys Pro Leu Leu Ser Asp Ser
        490                 495                 500 acc cag ttg ggt ttt gat gcc ctg tgt gac agc gac gac aca gcc atg      1589
Thr Gln Leu Gly Phe Asp Ala Leu Cys Asp Ser Asp Asp Thr Ala Met
505                 510                 515 gct aca ttc atg aat tac ctc gaa gca gag ggt ggc ctg ggt gac cct      1637
Ala Thr Phe Met Asn Tyr Leu Glu Ala Glu Gly Gly Leu Gly Asp Pro
520                 525                 530                 535 ggg gac ttc                                                          1646
Gly Asp Phe <210> SEQ ID NO 18
<211> LENGTH: 538
<212> TYPE: PRT
<213> ORGANISM: Rattus norvegicus

<400> SEQUENCE: 18

Met Glu Leu Pro Arg Lys Arg Arg Ser Asp Ser Glu Leu Leu Gln
 1               5                  10                  15

Glu Ala His Ser Gln Thr Glu Lys Arg Arg Asp Lys Met Asn His
            20                  25                  30

Leu Ile Trp Lys Leu Ser Ser Met Ile Pro Pro His Ile Pro Thr Ala
                35                  40                  45

His Lys Leu Asp Lys Leu Ser Val Leu Arg Arg Ala Val Gln Tyr Leu
        50                  55                  60

Arg Ser Gln Arg Gly Met Thr Glu Phe Tyr Leu Gly Glu Asn Ala Lys
 65                 70                  75                  80

Pro Ser Phe Ile Gln Asp Lys Glu Leu Ser His Leu Ile Leu Lys Ala
                85                  90                  95

Ala Glu Gly Phe Leu Leu Val Val Gly Cys Glu Gly Gly Arg Ile Leu
            100                 105                 110

Phe Val Ser Lys Ser Val Ser Lys Thr Leu His Tyr Asp Gln Ala Ser
        115                 120                 125

Leu Met Gly Gln Asn Leu Phe Asp Phe Leu His Pro Lys Asp Val Ala
    130                 135                 140

Lys Val Lys Glu Gln Leu Ser Cys Asp Val Ser Leu Arg Glu Lys Pro
145                 150                 155                 160

Ile Gly Thr Lys Thr Ser Pro Gln Val His Ser His Ser His Ile Gly
                165                 170                 175

Arg Ser Arg Val His Ser Gly Ser Arg Arg Ser Phe Phe Arg Met
            180                 185                 190

Lys Ser Ser Cys Thr Val Pro Val Lys Glu Glu Gln Arg Cys Ser Ser
        195                 200                 205

Cys Ser Lys Lys Asp Gln Arg Lys Phe His Thr Ile His Cys Thr
    210                 215                 220

Gly Tyr Leu Arg Ser Trp Pro Pro Asn Val Val Gly Thr Glu Lys Glu
225                 230                 235                 240

Met Gly Ser Gly Lys Asp Ser Gly Pro Leu Thr Cys Leu Val Ala Met
                245                 250                 255

Gly Arg Leu Gln Pro Tyr Thr Val Pro Pro Lys Asn Gly Lys Ile Asn
            260                 265                 270

Val Arg Pro Ala Glu Phe Ile Thr Arg Phe Ala Met Asn Gly Lys Phe
        275                 280                 285

Val Tyr Val Asp Gln Arg Ala Thr Ala Ile Leu Gly Tyr Leu Pro Gln
```

-continued

```
                    290                 295                 300
Glu Leu Leu Gly Thr Ser Cys Tyr Glu Tyr Phe His Gln Asp Asp His
305                 310                 315                 320

Ser Asn Leu Ser Asp Lys His Lys Ala Val Leu Gln Ser Lys Glu Lys
                325                 330                 335

Ile Leu Thr Asp Ser Tyr Lys Phe Arg Val Lys Asp Gly Ser Phe Val
            340                 345                 350

Thr Leu Lys Ser Lys Trp Phe Ser Phe Thr Asn Pro Trp Thr Lys Lys
        355                 360                 365

Leu Glu Tyr Ile Val Ser Val Asn Thr Leu Val Leu Gly Arg Ser Glu
    370                 375                 380

Thr Ala Val Ser Val Pro Gln Cys Arg Ser Ser Gln Ser Ser Glu Asp
385                 390                 395                 400

Ser Phe Arg Gln Pro Cys Val Ser Val Pro Gly Ile Ser Thr Gly Thr
                405                 410                 415

Leu Leu Gly Thr Gly Ser Ile Gly Thr Asp Ile Ala Asn Glu Val Leu
            420                 425                 430

Ser Leu Gln Arg Ser His Ser Ser Pro Glu Asp Ala Asn Pro Ser
        435                 440                 445

Gly Val Val Arg Asp Lys His Ser Val Asn Phe Gly Ser Ala Pro Val
    450                 455                 460

Pro Val Ser Thr Gly Glu Leu Phe Ala Leu Ser Pro Glu Thr Glu Gly
465                 470                 475                 480

Leu Glu Ala Ala Arg Gln His Gln Ser Ser Glu Pro Ala His Cys His
                485                 490                 495

Lys Pro Leu Leu Ser Asp Ser Thr Gln Leu Gly Phe Asp Ala Leu Cys
            500                 505                 510

Asp Ser Asp Asp Thr Ala Met Ala Thr Phe Met Asn Tyr Leu Glu Ala
        515                 520                 525

Glu Gly Gly Leu Gly Asp Pro Gly Asp Phe
    530                 535
```

```
<210> SEQ ID NO 19
<211> LENGTH: 1655
<212> TYPE: DNA
<213> ORGANISM: Rattus norvegicus
<220> FEATURE:
<221> NAME/KEY: CDS
<222> LOCATION: (33)..(1655)

<400> SEQUENCE: 19
```

```
tcacagctcc tggacctgtc agctctcttg ca atg gag ttg cca agg aaa cgt      53
                                   Met Glu Leu Pro Arg Lys Arg
                                     1               5 aga aga agt gat tca gag ctg ctc cag tca gaa ttc agg aca gat gca     101
Arg Arg Ser Asp Ser Glu Leu Leu Gln Ser Glu Phe Arg Thr Asp Ala
         10                  15                  20 atg gtg gaa aac ctt ccc cgg agt ccc ttt acc tct gtt ctt tca aca     149
Met Val Glu Asn Leu Pro Arg Ser Pro Phe Thr Ser Val Leu Ser Thr
     25                  30                  35 aga aca gga gta gca gtg ccc aat ggc atc agg gaa gct cac agc cag     197
Arg Thr Gly Val Ala Val Pro Asn Gly Ile Arg Glu Ala His Ser Gln
 40                  45                  50                  55 aca gaa aag cgt cgg aga gac aag atg aac cat ctg att tgg aaa ctg     245
Thr Glu Lys Arg Arg Arg Asp Lys Met Asn His Leu Ile Trp Lys Leu
                 60                  65                  70 tca tct atg atc cct cca cac atc ccc aca gcc cac aaa ctg gac aaa     293
```

-continued

| | |
|---|---|
| Ser Ser Met Ile Pro Pro His Ile Pro Thr Ala His Lys Leu Asp Lys<br>     75       80       85 | |
| ctg agc gtc ctg agg agg gca gtg cag tac ttg agg tct cag aga ggc<br>Leu Ser Val Leu Arg Arg Ala Val Gln Tyr Leu Arg Ser Gln Arg Gly<br>    90       95      100 | 341 |
| atg aca gag ttt tat tta gga gaa aat gct aaa cct tca ttt att cag<br>Met Thr Glu Phe Tyr Leu Gly Glu Asn Ala Lys Pro Ser Phe Ile Gln<br>105       110       115 | 389 |
| gat aag gaa ctc agc cac tta atc ctc aag gct agt ttg atg gga cag<br>Asp Lys Glu Leu Ser His Leu Ile Leu Lys Ala Ser Leu Met Gly Gln<br>120       125       130      135 | 437 |
| aac ttg ttt gac ttc tta cac cca aaa gat gtc gcc aaa gta aag gaa<br>Asn Leu Phe Asp Phe Leu His Pro Lys Asp Val Ala Lys Val Lys Glu<br>      140      145      150 | 485 |
| caa ctt tct tgt gat gtt tca ctg aga gag aaa ccc ata ggc acc aaa<br>Gln Leu Ser Cys Asp Val Ser Leu Arg Glu Lys Pro Ile Gly Thr Lys<br>    155       160      165 | 533 |
| acc tct cct cag gtt cac agt cac tcc cat att ggg cga tca cgc gtg<br>Thr Ser Pro Gln Val His Ser His Ser His Ile Gly Arg Ser Arg Val<br>      170      175      180 | 581 |
| cat tct ggc tcc aga cga tct ttc ttc ttt aga atg aag agc agc tgt<br>His Ser Gly Ser Arg Arg Ser Phe Phe Phe Arg Met Lys Ser Ser Cys<br>    185       190      195 | 629 |
| aca gtc ccc gtc aaa gaa gag caa cga tgc tcg tcc tgt tca aag aag<br>Thr Val Pro Val Lys Glu Glu Gln Arg Cys Ser Ser Cys Ser Lys Lys<br>200       205       210      215 | 677 |
| aaa gac cag aga aaa ttc cac acc atc cat tgc act gga tac ttg aga<br>Lys Asp Gln Arg Lys Phe His Thr Ile His Cys Thr Gly Tyr Leu Arg<br>      220      225      230 | 725 |
| agc tgg cca ccg aat gtt gtg ggc acg gag aaa gag atg ggc agt ggg<br>Ser Trp Pro Pro Asn Val Val Gly Thr Glu Lys Glu Met Gly Ser Gly<br>    235       240      245 | 773 |
| aaa gac agt ggt cct ctt acc tgc ctt gtg gct atg gga cgg tta cag<br>Lys Asp Ser Gly Pro Leu Thr Cys Leu Val Ala Met Gly Arg Leu Gln<br>250       255       260 | 821 |
| cca tat act gtc ccc ccg aag aat ggc aag atc aac gtg aga ccg gct<br>Pro Tyr Thr Val Pro Pro Lys Asn Gly Lys Ile Asn Val Arg Pro Ala<br>265       270       275 | 869 |
| gag ttc ata acc cga ttc gca atg aac ggg aaa ttc gtc tac gtc gac<br>Glu Phe Ile Thr Arg Phe Ala Met Asn Gly Lys Phe Val Tyr Val Asp<br>280       285       290      295 | 917 |
| caa agg gca aca gca att tta gga tac ctg cct cag gaa ctt ttg gga<br>Gln Arg Ala Thr Ala Ile Leu Gly Tyr Leu Pro Gln Glu Leu Leu Gly<br>      300      305      310 | 965 |
| act tcg tgt tat gaa tat ttt cat cag gat gac cac agt aat ttg agt<br>Thr Ser Cys Tyr Glu Tyr Phe His Gln Asp Asp His Ser Asn Leu Ser<br>    315       320      325 | 1013 |
| gac aag cac aaa gca gtt ctg cag agt aag gag aaa ata ctt aca gat<br>Asp Lys His Lys Ala Val Leu Gln Ser Lys Glu Lys Ile Leu Thr Asp<br>330       335       340 | 1061 |
| tca tac aaa ttc aga gtg aag gat ggc tcc ttt gtg act ctg aag agc<br>Ser Tyr Lys Phe Arg Val Lys Asp Gly Ser Phe Val Thr Leu Lys Ser<br>345       350       355 | 1109 |
| aag tgg ttc agc ttc act aac cct tgg acc aaa aag ctg gag tac atc<br>Lys Trp Phe Ser Phe Thr Asn Pro Trp Thr Lys Lys Leu Glu Tyr Ile<br>360       365       370      375 | 1157 |
| gtg tct gtc aac acg ctg gtt ttg ggg cgc agt gag acc gca gta tcc<br>Val Ser Val Asn Thr Leu Val Leu Gly Arg Ser Glu Thr Ala Val Ser<br>      380      385      390 | 1205 |

-continued

```
gtg cct cag tgc cgc agc agc cag tcc tct gaa gac tca ttt aga caa    1253
Val Pro Gln Cys Arg Ser Ser Gln Ser Ser Glu Asp Ser Phe Arg Gln
        395                 400                 405 ccc tgc gtc agt gtg ccg ggc ata tcc aca ggg acc tta ctt ggc act    1301
Pro Cys Val Ser Val Pro Gly Ile Ser Thr Gly Thr Leu Leu Gly Thr
    410                 415                 420 ggg agt att gga aca gat att gca aat gag gtt ctg agt tta cag agg    1349
Gly Ser Ile Gly Thr Asp Ile Ala Asn Glu Val Leu Ser Leu Gln Arg
425                 430                 435 tca cac tct tca tcc cca gaa gac gca aac cct tca gga gta gtg aga    1397
Ser His Ser Ser Ser Pro Glu Asp Ala Asn Pro Ser Gly Val Val Arg
440                 445                 450                 455 gat aag cac agt gta aac ttc ggg agc gcc cct gtg ccc gtg tcc act    1445
Asp Lys His Ser Val Asn Phe Gly Ser Ala Pro Val Pro Val Ser Thr
            460                 465                 470 ggg gag ctc ttt gca ctg agt cct gaa aca gag ggc ctg gag gct gcc    1493
Gly Glu Leu Phe Ala Leu Ser Pro Glu Thr Glu Gly Leu Glu Ala Ala
        475                 480                 485 agg caa cac cag agt tct gag ccc gcc cac tgt cac aaa cca ctc ctc    1541
Arg Gln His Gln Ser Ser Glu Pro Ala His Cys His Lys Pro Leu Leu
    490                 495                 500 agt gac agt acc cag ttg ggt ttt gat gcc ctg tgt gac agc gac gac    1589
Ser Asp Ser Thr Gln Leu Gly Phe Asp Ala Leu Cys Asp Ser Asp Asp
505                 510                 515 aca gcc atg gct aca ttc atg aat tac ctc gaa gca gag ggt ggc ctg    1637
Thr Ala Met Ala Thr Phe Met Asn Tyr Leu Glu Ala Glu Gly Gly Leu
520                 525                 530                 535 ggt gac cct ggg gac ttc                                            1655
Gly Asp Pro Gly Asp Phe
            540
```

<210> SEQ ID NO 20
<211> LENGTH: 541
<212> TYPE: PRT
<213> ORGANISM: Rattus norvegicus

<400> SEQUENCE: 20

```
Met Glu Leu Pro Arg Lys Arg Arg Ser Asp Ser Glu Leu Leu Gln
1               5                   10                  15

Ser Glu Phe Arg Thr Asp Ala Met Val Glu Asn Leu Pro Arg Ser Pro
            20                  25                  30

Phe Thr Ser Val Leu Ser Thr Arg Thr Gly Val Ala Val Pro Asn Gly
        35                  40                  45

Ile Arg Glu Ala His Ser Gln Thr Glu Lys Arg Arg Asp Lys Met
    50                  55                  60

Asn His Leu Ile Trp Lys Leu Ser Ser Met Ile Pro Pro His Ile Pro
65                  70                  75                  80

Thr Ala His Lys Leu Asp Lys Leu Ser Val Leu Arg Arg Ala Val Gln
                85                  90                  95

Tyr Leu Arg Ser Gln Arg Gly Met Thr Glu Phe Tyr Leu Gly Glu Asn
            100                 105                 110

Ala Lys Pro Ser Phe Ile Gln Asp Lys Glu Leu Ser His Leu Ile Leu
        115                 120                 125

Lys Ala Ser Leu Met Gly Gln Asn Leu Phe Asp Phe Leu His Pro Lys
    130                 135                 140

Asp Val Ala Lys Val Lys Glu Gln Leu Ser Cys Asp Val Ser Leu Arg
145                 150                 155                 160

Glu Lys Pro Ile Gly Thr Lys Thr Ser Pro Gln Val His Ser His Ser
```

```
                    165                 170                 175
His Ile Gly Arg Ser Arg Val His Ser Gly Ser Arg Ser Phe Phe
            180                 185                 190
Phe Arg Met Lys Ser Ser Cys Thr Val Pro Val Lys Glu Glu Gln Arg
        195                 200                 205
Cys Ser Cys Ser Lys Lys Lys Asp Gln Arg Lys Phe His Thr Ile
210                 215                 220
His Cys Thr Gly Tyr Leu Arg Ser Trp Pro Pro Asn Val Val Gly Thr
225                 230                 235                 240
Glu Lys Glu Met Gly Ser Gly Lys Asp Ser Gly Pro Leu Thr Cys Leu
            245                 250                 255
Val Ala Met Gly Arg Leu Gln Pro Tyr Thr Val Pro Pro Lys Asn Gly
            260                 265                 270
Lys Ile Asn Val Arg Pro Ala Glu Phe Ile Thr Arg Phe Ala Met Asn
        275                 280                 285
Gly Lys Phe Val Tyr Val Asp Gln Arg Ala Thr Ala Ile Leu Gly Tyr
        290                 295                 300
Leu Pro Gln Glu Leu Leu Gly Thr Ser Cys Tyr Glu Tyr Phe His Gln
305                 310                 315                 320
Asp Asp His Ser Asn Leu Ser Asp Lys His Lys Ala Val Leu Gln Ser
                325                 330                 335
Lys Glu Lys Ile Leu Thr Asp Ser Tyr Lys Phe Arg Val Lys Asp Gly
            340                 345                 350
Ser Phe Val Thr Leu Lys Ser Lys Trp Phe Ser Phe Thr Asn Pro Trp
            355                 360                 365
Thr Lys Lys Leu Glu Tyr Ile Val Ser Val Asn Thr Leu Val Leu Gly
370                 375                 380
Arg Ser Glu Thr Ala Val Ser Val Pro Gln Cys Arg Ser Ser Gln Ser
385                 390                 395                 400
Ser Glu Asp Ser Phe Arg Gln Pro Cys Val Ser Val Pro Gly Ile Ser
                405                 410                 415
Thr Gly Thr Leu Leu Gly Thr Gly Ser Ile Gly Thr Asp Ile Ala Asn
            420                 425                 430
Glu Val Leu Ser Leu Gln Arg Ser His Ser Ser Ser Pro Glu Asp Ala
            435                 440                 445
Asn Pro Ser Gly Val Val Arg Asp Lys His Ser Val Asn Phe Gly Ser
        450                 455                 460
Ala Pro Val Pro Val Ser Thr Gly Glu Leu Phe Ala Leu Ser Pro Glu
465                 470                 475                 480
Thr Glu Gly Leu Glu Ala Ala Arg Gln His Gln Ser Ser Glu Pro Ala
            485                 490                 495
His Cys His Lys Pro Leu Leu Ser Asp Ser Thr Gln Leu Gly Phe Asp
                500                 505                 510
Ala Leu Cys Asp Ser Asp Asp Thr Ala Met Ala Thr Phe Met Asn Tyr
            515                 520                 525
Leu Glu Ala Glu Gly Gly Leu Gly Asp Pro Gly Asp Phe
530                 535                 540

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:Sense
      primer 1
```

```
<400> SEQUENCE: 21
actagtcgac ttatgttttt taccataagc acc                                    33

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:Antisense
      primer 1

<400> SEQUENCE: 22
gtcgacctgc gctactgtgg ctgagctttg                                        30

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:per-F
<220> FEATURE:
<221> NAME/KEY: modified_base
<222> LOCATION: (16)
<223> OTHER INFORMATION: i
<220> FEATURE:
<221> NAME/KEY: modified_base
<222> LOCATION: (19)
<223> OTHER INFORMATION: i

<400> SEQUENCE: 23
cagcagatsa rctgyntsng acagyrtcmt cag                                    33

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:per-R
<220> FEATURE:
<221> NAME/KEY: modified_base
<222> LOCATION: (19)
<223> OTHER INFORMATION: i

<400> SEQUENCE: 24
gctrcactgr ctgrtgmsng acrccacrct c                                      31

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:cPer2-R1
      primer

<400> SEQUENCE: 25
ttgctgtacc aggcacatta caac                                              24

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:YK-F1
<220> FEATURE:
<221> NAME/KEY: modified_base
<222> LOCATION: (3)
<223> OTHER INFORMATION: i
<220> FEATURE:
```

```
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (24)
<223> OTHER INFORMATION: i
<220> FEATURE:
<221> NAME/KEY: modified_base
<222> LOCATION: (27)
<223> OTHER INFORMATION: i
<220> FEATURE:
<221> NAME/KEY: modified_base
<222> LOCATION: (30)
<223> OTHER INFORMATION: i

<400> SEQUENCE: 26
rtncaytcng gntaycargc nccnmgnatn cc                                  32

<210> SEQ ID NO 27
<211> LENGTH: 4035
<212> TYPE: DNA
<213> ORGANISM: Gallus gallus
<220> FEATURE:
<221> NAME/KEY: CDS
<222> LOCATION: (1)..(4035)

<400> SEQUENCE: 27 atg gac tgt atc gag gtc agg ggg ttc tac tct agc act gag gag cag     48
Met Asp Cys Ile Glu Val Arg Gly Phe Tyr Ser Ser Thr Glu Glu Gln
 1               5                  10                  15 aac cct gag cag caa gct gat atc agt gaa aac att tct tca ttg ttc     96
Asn Pro Glu Gln Gln Ala Asp Ile Ser Glu Asn Ile Ser Ser Leu Phe
             20                  25                  30 tct tta aaa gag caa cag aaa atg agt gag tat tct gga ctt gca agt    144
Ser Leu Lys Glu Gln Gln Lys Met Ser Glu Tyr Ser Gly Leu Ala Ser
         35                  40                  45 aac cat agc cag atg att gct gaa gat tct gaa att cag cca aaa cct    192
Asn His Ser Gln Met Ile Ala Glu Asp Ser Glu Ile Gln Pro Lys Pro
     50                  55                  60 gaa cac tct ccc gaa gtc ctt cag gaa gat att gag atg agc agc gga    240
Glu His Ser Pro Glu Val Leu Gln Glu Asp Ile Glu Met Ser Ser Gly
 65                  70                  75                  80 tcc agt gga aat gac ttc agt gga aat gag acg aat gaa aac tac tcc    288
Ser Ser Gly Asn Asp Phe Ser Gly Asn Glu Thr Asn Glu Asn Tyr Ser
                 85                  90                  95 agt gga cat gat tct cat ggc cac gaa tct gat gaa aat ggg aaa gat    336
Ser Gly His Asp Ser His Gly His Glu Ser Asp Glu Asn Gly Lys Asp
            100                 105                 110 tca gca atg ctc atg gaa tct tca gac tgt cat aaa agt tca agc tca    384
Ser Ala Met Leu Met Glu Ser Ser Asp Cys His Lys Ser Ser Ser Ser
        115                 120                 125 aat gca ttt agt ctg atg att gcg aac tct gaa cac aat cag tct agc    432
Asn Ala Phe Ser Leu Met Ile Ala Asn Ser Glu His Asn Gln Ser Ser
    130                 135                 140 agt gga tgc agc agc gag cag tct act aaa gcc aaa acg caa aag gaa    480
Ser Gly Cys Ser Ser Glu Gln Ser Thr Lys Ala Lys Thr Gln Lys Glu
145                 150                 155                 160
```

```
ttg ttg aag aca ttg caa gag ctg aaa gct cac ctt cct gct gaa aaa      528
Leu Leu Lys Thr Leu Gln Glu Leu Lys Ala His Leu Pro Ala Glu Lys
            165                 170                 175 aga att aaa ggc aaa tcc agt gtc cta aca aca ctg aaa tat gcc ctt      576
Arg Ile Lys Gly Lys Ser Ser Val Leu Thr Thr Leu Lys Tyr Ala Leu
        180                 185                 190 aaa agc att aaa caa gtt aaa gcc aat gag gaa tat tac caa ttg ttg      624
Lys Ser Ile Lys Gln Val Lys Ala Asn Glu Glu Tyr Tyr Gln Leu Leu
    195                 200                 205 atg att aat gaa tcc cag cct tct gga ctc aat gtg tca tct tat aca      672
Met Ile Asn Glu Ser Gln Pro Ser Gly Leu Asn Val Ser Ser Tyr Thr
210                 215                 220 gtg gaa gaa gtt gag act ata acc tca gaa tac atc atg aaa aat gca      720
Val Glu Glu Val Glu Thr Ile Thr Ser Glu Tyr Ile Met Lys Asn Ala
225                 230                 235                 240 gat atg ttt gct gta gct gtt tct ttg att act ggg aaa att gtg tac      768
Asp Met Phe Ala Val Ala Val Ser Leu Ile Thr Gly Lys Ile Val Tyr
                245                 250                 255 atc tct gat caa gct gct gct att ctg cgc tgt aag agg agt tat ttt      816
Ile Ser Asp Gln Ala Ala Ala Ile Leu Arg Cys Lys Arg Ser Tyr Phe
            260                 265                 270 aaa aat gcc aaa ttt gtg gag tta ttg gca cct caa gat gtc agt gtt      864
Lys Asn Ala Lys Phe Val Glu Leu Leu Ala Pro Gln Asp Val Ser Val
        275                 280                 285 ttc tat act tct act acc cca tac aga tta cca tct tgg aat att tgc      912
Phe Tyr Thr Ser Thr Thr Pro Tyr Arg Leu Pro Ser Trp Asn Ile Cys
    290                 295                 300 agc aga gct gag tct tcc acc cag gat tgc atg gaa gag aaa tcc ttt      960
Ser Arg Ala Glu Ser Ser Thr Gln Asp Cys Met Glu Glu Lys Ser Phe
305                 310                 315                 320 ttc tgt cgc atc agt gca gga aag gag cgt gaa aat gag att tgc tat     1008
Phe Cys Arg Ile Ser Ala Gly Lys Glu Arg Glu Asn Glu Ile Cys Tyr
                325                 330                 335 cac cca ttt cgg atg act cct tac ctt atc aaa gta caa gat cca gaa     1056
His Pro Phe Arg Met Thr Pro Tyr Leu Ile Lys Val Gln Asp Pro Glu
            340                 345                 350 gta gca gag gac caa ctt tgt tgt gtg ctc ctt gca gaa aaa gtg cac     1104
Val Ala Glu Asp Gln Leu Cys Cys Val Leu Leu Ala Glu Lys Val His
        355                 360                 365 tct ggt tat gaa gca ccc aga att cct cca gac aaa aga att ttt aca     1152
Ser Gly Tyr Glu Ala Pro Arg Ile Pro Pro Asp Lys Arg Ile Phe Thr
    370                 375                 380 aca aca cac aca cca acc tgt ttg ttc cag gat gta gat gag aga gct     1200
Thr Thr His Thr Pro Thr Cys Leu Phe Gln Asp Val Asp Glu Arg Ala
385                 390                 395                 400 gta cct ctg ttg gga tac cta cct cag gac tta ata gga acg cct gtt     1248
Val Pro Leu Leu Gly Tyr Leu Pro Gln Asp Leu Ile Gly Thr Pro Val
                405                 410                 415 ttg gtg cat ctt cac cca aat gac aga ccc tta atg cta gca att cac     1296
Leu Val His Leu His Pro Asn Asp Arg Pro Leu Met Leu Ala Ile His
            420                 425                 430 aaa aaa ata ctt caa tat gga gga cag cct ttt gac tat tca cca atc     1344
Lys Lys Ile Leu Gln Tyr Gly Gly Gln Pro Phe Asp Tyr Ser Pro Ile
        435                 440                 445 agg ttt tgc act aga aat gga gat tat ata acc atg gac act agc tgg     1392
Arg Phe Cys Thr Arg Asn Gly Asp Tyr Ile Thr Met Asp Thr Ser Trp
    450                 455                 460 tcc agt ttc atc aat cct tgg agt cga aag gtt tca ttt atc att gga     1440
Ser Ser Phe Ile Asn Pro Trp Ser Arg Lys Val Ser Phe Ile Ile Gly
465                 470                 475                 480
```

-continued

| | |
|---|---|
| aga cac aaa gtt agg acg ggt ccc tta aat gaa gat gtt ttt gcc gct<br>Arg His Lys Val Arg Thr Gly Pro Leu Asn Glu Asp Val Phe Ala Ala<br>                        485                    490                    495 | 1488 |
| ccc aac tat acg gag gac aga atc ctt cac ccc agt gtt cag gag atc<br>Pro Asn Tyr Thr Glu Asp Arg Ile Leu His Pro Ser Val Gln Glu Ile<br>            500                    505                    510 | 1536 |
| aca gag caa ata tat cgg ctg tta cta cag cct gta cac aac agt gga<br>Thr Glu Gln Ile Tyr Arg Leu Leu Leu Gln Pro Val His Asn Ser Gly<br>                515                    520                    525 | 1584 |
| tcc agt ggc tat gga agt cta ggt agc aat ggc tca cac gaa cac tta<br>Ser Ser Gly Tyr Gly Ser Leu Gly Ser Asn Gly Ser His Glu His Leu<br>530                      535                    540 | 1632 |
| atg agt gtg gca tcc tcc agt gac agc aca gga aat aat aat gat gac<br>Met Ser Val Ala Ser Ser Ser Asp Ser Thr Gly Asn Asn Asn Asp Asp<br>545                    550                    555                    560 | 1680 |
| aca caa aag gat aaa aca ata agt caa gat gcc cgt aag gtc aaa act<br>Thr Gln Lys Asp Lys Thr Ile Ser Gln Asp Ala Arg Lys Val Lys Thr<br>                        565                    570                    575 | 1728 |
| aaa gga cag cat att ttc act gag aat aaa gga aaa ctg gaa tat aaa<br>Lys Gly Gln His Ile Phe Thr Glu Asn Lys Gly Lys Leu Glu Tyr Lys<br>                580                    585                    590 | 1776 |
| aga gag cct tct gca gaa aaa caa aat ggt cct ggt ggt cag gtg aaa<br>Arg Glu Pro Ser Ala Glu Lys Gln Asn Gly Pro Gly Gly Gln Val Lys<br>            595                    600                    605 | 1824 |
| gat gtg ata gga aag gat acc aca gct aca gct gct cct aaa aat gtg<br>Asp Val Ile Gly Lys Asp Thr Thr Ala Thr Ala Ala Pro Lys Asn Val<br>610                    615                    620 | 1872 |
| gct act gaa gag ttg gca tgg aaa gaa caa cct gta tat tct tat caa<br>Ala Thr Glu Glu Leu Ala Trp Lys Glu Gln Pro Val Tyr Ser Tyr Gln<br>625                    630                    635                    640 | 1920 |
| cag att agc tgc ttg gat agt gtc atc agg tat ttg gag agt tgt aat<br>Gln Ile Ser Cys Leu Asp Ser Val Ile Arg Tyr Leu Glu Ser Cys Asn<br>                        645                    650                    655 | 1968 |
| gtg cct ggt aca gca aaa aga aaa tgt gaa cct tca tca agt gtg aat<br>Val Pro Gly Thr Ala Lys Arg Lys Cys Glu Pro Ser Ser Ser Val Asn<br>                660                    665                    670 | 2016 |
| tct agt gtt cac gag caa aaa gca tct gtt aat gct ata caa ccc tta<br>Ser Ser Val His Glu Gln Lys Ala Ser Val Asn Ala Ile Gln Pro Leu<br>            675                    680                    685 | 2064 |
| gga gac tct act gtg ttg aag tca tct ggt aaa tca agt ggt ccc cca<br>Gly Asp Ser Thr Val Leu Lys Ser Ser Gly Lys Ser Ser Gly Pro Pro<br>690                    695                    700 | 2112 |
| gta gtt ggt gct cac tta act tct ttg gcc tta cct ggc aag cct gaa<br>Val Val Gly Ala His Leu Thr Ser Leu Ala Leu Pro Gly Lys Pro Glu<br>705                    710                    715                    720 | 2160 |
| agt gtt gta tcg ctc acc agt cag tgc agc tac agt agc acc att gtt<br>Ser Val Val Ser Leu Thr Ser Gln Cys Ser Tyr Ser Ser Thr Ile Val<br>                        725                    730                    735 | 2208 |
| cat gtt gga gac aaa aaa cca caa cct gaa tta gaa atg ata gaa gat<br>His Val Gly Asp Lys Lys Pro Gln Pro Glu Leu Glu Met Ile Glu Asp<br>            740                    745                    750 | 2256 |
| ggt cca agt gga gca gaa gtc tta gat act caa ctt cct gcc cct cca<br>Gly Pro Ser Gly Ala Glu Val Leu Asp Thr Gln Leu Pro Ala Pro Pro<br>            755                    760                    765 | 2304 |
| ccc agc tct acg cat gta aat cag gaa aag gag tca ttt aaa aaa ctg<br>Pro Ser Ser Thr His Val Asn Gln Glu Lys Glu Ser Phe Lys Lys Leu<br>770                    775                    780 | 2352 |
| gga ctt aca aag gaa gtc ctt gca gtg cat aca caa aaa gaa gag caa<br>Gly Leu Thr Lys Glu Val Leu Ala Val His Thr Gln Lys Glu Glu Gln | 2400 |

```
                                                              -continued
      785                790                795                800
agc ttt ttg aat aag ttc aaa gaa atc aag aga ttc aat att ttc cag    2448
Ser Phe Leu Asn Lys Phe Lys Glu Ile Lys Arg Phe Asn Ile Phe Gln
                 805                810                815 tcc cac tgc aat tac tac tta caa gat aaa cct aaa gga agg cct ggt    2496
Ser His Cys Asn Tyr Tyr Leu Gln Asp Lys Pro Lys Gly Arg Pro Gly
             820                825                830 gaa cgt ggt ggc cgc gga caa cga aat gga act tct gga atg gat cag    2544
Glu Arg Gly Gly Arg Gly Gln Arg Asn Gly Thr Ser Gly Met Asp Gln
         835                840                845 cct tgg aag aaa agt ggg aaa aac agg aaa tca aaa cgc att aaa cca    2592
Pro Trp Lys Lys Ser Gly Lys Asn Arg Lys Ser Lys Arg Ile Lys Pro
     850                855                860 cag gag tct tca gac agt aca act tct gga act aaa ttc ccc cat cgc    2640
Gln Glu Ser Ser Asp Ser Thr Thr Ser Gly Thr Lys Phe Pro His Arg
865                870                875                880 ttt cct ctt cag ggt tta aat act acc gct tgg tca ccg tca gac act    2688
Phe Pro Leu Gln Gly Leu Asn Thr Thr Ala Trp Ser Pro Ser Asp Thr
                 885                890                895 tca caa gca agc tac tca gcg atg tct ttt cca act gtt atg cct gca    2736
Ser Gln Ala Ser Tyr Ser Ala Met Ser Phe Pro Thr Val Met Pro Ala
             900                905                910 tat ccg ctt cct gtt ttt cca gca gca gca gga act gtg cca cca gct    2784
Tyr Pro Leu Pro Val Phe Pro Ala Ala Ala Gly Thr Val Pro Pro Ala
         915                920                925 cct gag act tca gtc tct ggt ttt aat cag ctg cca gac tcg gga aat    2832
Pro Glu Thr Ser Val Ser Gly Phe Asn Gln Leu Pro Asp Ser Gly Asn
     930                935                940 act tgc tct atg caa cca tcc cag ttt tct gcc cct ctt atg aca ccc    2880
Thr Cys Ser Met Gln Pro Ser Gln Phe Ser Ala Pro Leu Met Thr Pro
945                950                955                960 gtt gta gct ctt gtg ctc ccc aac tat gtc tac cca gaa atg aac aat    2928
Val Val Ala Leu Val Leu Pro Asn Tyr Val Tyr Pro Glu Met Asn Asn
                 965                970                975 agc tta cct caa aca ctt tac cac agc caa gcc aat ttt ccc acc cat    2976
Ser Leu Pro Gln Thr Leu Tyr His Ser Gln Ala Asn Phe Pro Thr His
             980                985                990 cct gct ttc tct tca cag aca gta ttt cca gcg cag cct cca ttc act    3024
Pro Ala Phe Ser Ser Gln Thr Val Phe Pro Ala Gln Pro Pro Phe Thr
         995                1000               1005 acc cct agc cct ttc cca caa cag gcg ttt ttt cca atg caa cca ttc    3072
Thr Pro Ser Pro Phe Pro Gln Gln Ala Phe Phe Pro Met Gln Pro Phe
     1010               1015               1020 cat tat aat cca cca gca gaa att gaa aag gtt cct gtc aca gag aca    3120
His Tyr Asn Pro Pro Ala Glu Ile Glu Lys Val Pro Val Thr Glu Thr
1025               1030               1035               1040 cga aac gag cca tcc cgt tcc tgc act cca cag tca gtg ggt cct caa    3168
Arg Asn Glu Pro Ser Arg Ser Cys Thr Pro Gln Ser Val Gly Pro Gln
                 1045               1050               1055 gac cag gct tca ccg cct ttg ttc caa tca agg tgt agt tct cct ctg    3216
Asp Gln Ala Ser Pro Pro Leu Phe Gln Ser Arg Cys Ser Ser Pro Leu
             1060               1065               1070 aat ctt cta cag ttg gaa gaa aac aca aaa act gtg gaa agt gga gct    3264
Asn Leu Leu Gln Leu Glu Glu Asn Thr Lys Thr Val Glu Ser Gly Ala
         1075               1080               1085 cct gca ggt ttg cat gga gct tta aat gag gaa gga acc ata ggc aaa    3312
Pro Ala Gly Leu His Gly Ala Leu Asn Glu Glu Gly Thr Ile Gly Lys
     1090               1095               1100 atc atg aca act gat gct ggt agt gga aag gga tcc cta cca gct gag    3360
```

```
Ile Met Thr Thr Asp Ala Gly Ser Gly Lys Gly Ser Leu Pro Ala Glu
1105                1110                1115                1120 tct cca atg gat gct caa aat agc gat gca ctc tcc atg tcc agt gtc     3408
Ser Pro Met Asp Ala Gln Asn Ser Asp Ala Leu Ser Met Ser Ser Val
            1125                1130                1135 ctg ctt gac att tta ctt caa gaa gat gca tgc tca ggc act ggc tca     3456
Leu Leu Asp Ile Leu Leu Gln Glu Asp Ala Cys Ser Gly Thr Gly Ser
        1140                1145                1150 gct tcc tca ggg agc ggt gta tct gca gct gct gaa tct ctc ggg tct     3504
Ala Ser Ser Gly Ser Gly Val Ser Ala Ala Ala Glu Ser Leu Gly Ser
    1155                1160                1165 gga tct aac ggc tgt gac atg tca ggg agc aga aca ggc agt agt gaa     3552
Gly Ser Asn Gly Cys Asp Met Ser Gly Ser Arg Thr Gly Ser Ser Glu
1170                1175                1180 act agt cat acc agc aaa tac ttt ggg agt atc gat tct tca gaa aac     3600
Thr Ser His Thr Ser Lys Tyr Phe Gly Ser Ile Asp Ser Ser Glu Asn
1185                1190                1195                1200 cat cat aaa aca aaa atg aag gca gaa ata gaa gaa agt gag cac ttc     3648
His His Lys Thr Lys Met Lys Ala Glu Ile Glu Glu Ser Glu His Phe
            1205                1210                1215 att aaa tat gtt ctt cag gat cct ata tgg ctt ttg atg gca aac aca     3696
Ile Lys Tyr Val Leu Gln Asp Pro Ile Trp Leu Leu Met Ala Asn Thr
        1220                1225                1230 gat gac acc gtt atg atg act tac cag tta ccc tct aga gat ttg gaa     3744
Asp Asp Thr Val Met Met Thr Tyr Gln Leu Pro Ser Arg Asp Leu Glu
    1235                1240                1245 aca gtt tta aaa gaa gat aag ctg aaa cta aag caa atg cag aaa cta     3792
Thr Val Leu Lys Glu Asp Lys Leu Lys Leu Lys Gln Met Gln Lys Leu
1250                1255                1260 caa cca aaa ttt act gaa gac caa aaa aga gag ctt att gaa gtt cat     3840
Gln Pro Lys Phe Thr Glu Asp Gln Lys Arg Glu Leu Ile Glu Val His
1265                1270                1275                1280 cca tgg atc cag caa ggt gga ctg cca aag act gtt gct aac tct gaa     3888
Pro Trp Ile Gln Gln Gly Gly Leu Pro Lys Thr Val Ala Asn Ser Glu
            1285                1290                1295 tgt att ttt tgt gag gac aat ata cag agc aat ttt tat aca tcg tac     3936
Cys Ile Phe Cys Glu Asp Asn Ile Gln Ser Asn Phe Tyr Thr Ser Tyr
        1300                1305                1310 gat gaa gaa atc cat gaa atg gac ctt aat gaa atg att gaa gac agt     3984
Asp Glu Glu Ile His Glu Met Asp Leu Asn Glu Met Ile Glu Asp Ser
    1315                1320                1325 ggg gag aac aat ttg gtt cct ctg agt caa gtc aat gaa gaa caa aca     4032
Gly Glu Asn Asn Leu Val Pro Leu Ser Gln Val Asn Glu Glu Gln Thr
1330                1335                1340 tag                                                                 4035

<210> SEQ ID NO 28
<211> LENGTH: 1344
<212> TYPE: PRT
<213> ORGANISM: Gallus gallus

<400> SEQUENCE: 28

Met Asp Cys Ile Glu Val Arg Gly Phe Tyr Ser Ser Thr Glu Glu Gln
1               5                   10                  15

Asn Pro Glu Gln Gln Ala Asp Ile Ser Glu Asn Ile Ser Ser Leu Phe
            20                  25                  30

Ser Leu Lys Glu Gln Gln Lys Met Ser Glu Tyr Ser Gly Leu Ala Ser
        35                  40                  45

Asn His Ser Gln Met Ile Ala Glu Asp Ser Glu Ile Gln Pro Lys Pro
```

-continued

```
             50                  55                  60
Glu His Ser Pro Glu Val Leu Gln Glu Asp Ile Glu Met Ser Ser Gly
 65                  70                  75                  80

Ser Ser Gly Asn Asp Phe Ser Gly Asn Glu Thr Asn Glu Asn Tyr Ser
                 85                  90                  95

Ser Gly His Asp Ser His Gly His Glu Ser Asp Glu Asn Gly Lys Asp
                100                 105                 110

Ser Ala Met Leu Met Glu Ser Asp Cys His Lys Ser Ser Ser Ser
            115                 120                 125

Asn Ala Phe Ser Leu Met Ile Ala Asn Ser Glu His Asn Gln Ser Ser
130                 135                 140

Ser Gly Cys Ser Ser Glu Gln Ser Thr Lys Ala Lys Thr Gln Lys Glu
145                 150                 155                 160

Leu Leu Lys Thr Leu Gln Glu Leu Lys Ala His Leu Pro Ala Glu Lys
                165                 170                 175

Arg Ile Lys Gly Lys Ser Ser Val Leu Thr Thr Leu Lys Tyr Ala Leu
                180                 185                 190

Lys Ser Ile Lys Gln Val Lys Ala Asn Glu Glu Tyr Tyr Gln Leu Leu
                195                 200                 205

Met Ile Asn Glu Ser Gln Pro Ser Gly Leu Asn Val Ser Ser Tyr Thr
            210                 215                 220

Val Glu Glu Val Glu Thr Ile Thr Ser Glu Tyr Ile Met Lys Asn Ala
225                 230                 235                 240

Asp Met Phe Ala Val Ala Val Ser Leu Ile Thr Gly Lys Ile Val Tyr
                245                 250                 255

Ile Ser Asp Gln Ala Ala Ala Ile Leu Arg Cys Lys Arg Ser Tyr Phe
            260                 265                 270

Lys Asn Ala Lys Phe Val Glu Leu Leu Ala Pro Gln Asp Val Ser Val
            275                 280                 285

Phe Tyr Thr Ser Thr Thr Pro Tyr Arg Leu Pro Ser Trp Asn Ile Cys
            290                 295                 300

Ser Arg Ala Glu Ser Ser Thr Gln Asp Cys Met Glu Glu Lys Ser Phe
305                 310                 315                 320

Phe Cys Arg Ile Ser Ala Gly Lys Glu Arg Glu Asn Glu Ile Cys Tyr
                325                 330                 335

His Pro Phe Arg Met Thr Pro Tyr Leu Ile Lys Val Gln Asp Pro Glu
            340                 345                 350

Val Ala Glu Asp Gln Leu Cys Cys Val Leu Leu Ala Glu Lys Val His
            355                 360                 365

Ser Gly Tyr Glu Ala Pro Arg Ile Pro Pro Asp Lys Arg Ile Phe Thr
            370                 375                 380

Thr Thr His Thr Pro Thr Cys Leu Phe Gln Asp Val Asp Glu Arg Ala
385                 390                 395                 400

Val Pro Leu Leu Gly Tyr Leu Pro Gln Asp Leu Ile Gly Thr Pro Val
                405                 410                 415

Leu Val His Leu His Pro Asn Asp Arg Pro Leu Met Leu Ala Ile His
                420                 425                 430

Lys Lys Ile Leu Gln Tyr Gly Gly Gln Pro Phe Asp Tyr Ser Pro Ile
            435                 440                 445

Arg Phe Cys Thr Arg Asn Gly Asp Tyr Ile Thr Met Asp Thr Ser Trp
            450                 455                 460

Ser Ser Phe Ile Asn Pro Trp Ser Arg Lys Val Ser Phe Ile Ile Gly
465                 470                 475                 480
```

-continued

```
Arg His Lys Val Arg Thr Gly Pro Leu Asn Glu Asp Val Phe Ala Ala
            485                 490                 495
Pro Asn Tyr Thr Glu Asp Arg Ile Leu His Pro Ser Val Gln Glu Ile
            500                 505                 510
Thr Glu Gln Ile Tyr Arg Leu Leu Leu Gln Pro Val His Asn Ser Gly
            515                 520                 525
Ser Ser Gly Tyr Gly Ser Leu Gly Ser Asn Gly Ser His Glu His Leu
            530                 535                 540
Met Ser Val Ala Ser Ser Asp Ser Thr Gly Asn Asn Asn Asp Asp
545                 550                 555                 560
Thr Gln Lys Asp Lys Thr Ile Ser Gln Asp Ala Arg Lys Val Lys Thr
            565                 570                 575
Lys Gly Gln His Ile Phe Thr Glu Asn Lys Gly Lys Leu Glu Tyr Lys
            580                 585                 590
Arg Glu Pro Ser Ala Glu Lys Gln Asn Gly Pro Gly Gln Val Lys
            595                 600                 605
Asp Val Ile Gly Lys Asp Thr Thr Ala Thr Ala Pro Lys Asn Val
            610                 615                 620
Ala Thr Glu Glu Leu Ala Trp Lys Glu Gln Pro Val Tyr Ser Tyr Gln
625                 630                 635                 640
Gln Ile Ser Cys Leu Asp Ser Val Ile Arg Tyr Leu Glu Ser Cys Asn
            645                 650                 655
Val Pro Gly Thr Ala Lys Arg Lys Cys Glu Pro Ser Ser Val Asn
            660                 665                 670
Ser Ser Val His Glu Gln Lys Ala Ser Val Asn Ala Ile Gln Pro Leu
            675                 680                 685
Gly Asp Ser Thr Val Leu Lys Ser Ser Gly Lys Ser Ser Gly Pro Pro
            690                 695                 700
Val Val Gly Ala His Leu Thr Ser Leu Ala Leu Pro Gly Lys Pro Glu
705                 710                 715                 720
Ser Val Val Ser Leu Thr Ser Gln Cys Ser Tyr Ser Ser Thr Ile Val
            725                 730                 735
His Val Gly Asp Lys Lys Pro Gln Pro Glu Leu Glu Met Ile Glu Asp
            740                 745                 750
Gly Pro Ser Gly Ala Glu Val Leu Asp Thr Gln Leu Pro Ala Pro Pro
            755                 760                 765
Pro Ser Ser Thr His Val Asn Gln Glu Lys Glu Ser Phe Lys Lys Leu
            770                 775                 780
Gly Leu Thr Lys Glu Val Leu Ala Val His Thr Gln Lys Glu Glu Gln
785                 790                 795                 800
Ser Phe Leu Asn Lys Phe Lys Glu Ile Lys Arg Phe Asn Ile Phe Gln
            805                 810                 815
Ser His Cys Asn Tyr Tyr Leu Gln Asp Lys Pro Lys Gly Arg Pro Gly
            820                 825                 830
Glu Arg Gly Gly Arg Gly Gln Arg Asn Gly Thr Ser Gly Met Asp Gln
            835                 840                 845
Pro Trp Lys Lys Ser Gly Lys Asn Arg Lys Ser Lys Arg Ile Lys Pro
850                 855                 860
Gln Glu Ser Ser Asp Ser Thr Thr Ser Gly Thr Lys Phe Pro His Arg
865                 870                 875                 880
Phe Pro Leu Gln Gly Leu Asn Thr Thr Ala Trp Ser Pro Ser Asp Thr
            885                 890                 895
```

```
Ser Gln Ala Ser Tyr Ser Ala Met Ser Phe Pro Thr Val Met Pro Ala
            900                 905                 910
Tyr Pro Leu Pro Val Phe Pro Ala Ala Gly Thr Val Pro Pro Ala
            915                 920             925
Pro Glu Thr Ser Val Ser Gly Phe Asn Gln Leu Pro Asp Ser Gly Asn
            930                 935                 940
Thr Cys Ser Met Gln Pro Ser Gln Phe Ser Ala Pro Leu Met Thr Pro
945                 950                 955                 960
Val Val Ala Leu Val Leu Pro Asn Tyr Val Tyr Pro Glu Met Asn Asn
            965                 970                 975
Ser Leu Pro Gln Thr Leu Tyr His Ser Gln Ala Asn Phe Pro Thr His
            980                 985                 990
Pro Ala Phe Ser Ser Gln Thr Val Phe Pro Ala Gln Pro Pro Phe Thr
            995                 1000                1005
Thr Pro Ser Pro Phe Pro Gln Gln Ala Phe Phe Pro Met Gln Pro Phe
            1010                1015                1020
His Tyr Asn Pro Pro Ala Glu Ile Glu Lys Val Pro Val Thr Glu Thr
1025                1030                1035                1040
Arg Asn Glu Pro Ser Arg Ser Cys Thr Pro Gln Ser Val Gly Pro Gln
            1045                1050                1055
Asp Gln Ala Ser Pro Pro Leu Phe Gln Ser Arg Cys Ser Ser Pro Leu
            1060                1065                1070
Asn Leu Leu Gln Leu Glu Glu Asn Thr Lys Thr Val Glu Ser Gly Ala
            1075                1080                1085
Pro Ala Gly Leu His Gly Ala Leu Asn Glu Glu Gly Thr Ile Gly Lys
            1090                1095                1100
Ile Met Thr Thr Asp Ala Gly Ser Gly Lys Gly Ser Leu Pro Ala Glu
1105                1110                1115                1120
Ser Pro Met Asp Ala Gln Asn Ser Asp Ala Leu Ser Met Ser Ser Val
            1125                1130                1135
Leu Leu Asp Ile Leu Leu Gln Glu Asp Ala Cys Ser Gly Thr Gly Ser
            1140                1145                1150
Ala Ser Ser Gly Ser Gly Val Ser Ala Ala Ala Glu Ser Leu Gly Ser
            1155                1160                1165
Gly Ser Asn Gly Cys Asp Met Ser Gly Ser Arg Thr Gly Ser Ser Glu
            1170                1175                1180
Thr Ser His Thr Ser Lys Tyr Phe Gly Ser Ile Asp Ser Ser Glu Asn
1185                1190                1195                1200
His His Lys Thr Lys Met Lys Ala Glu Ile Glu Ser Glu His Phe
            1205                1210                1215
Ile Lys Tyr Val Leu Gln Asp Pro Ile Trp Leu Leu Met Ala Asn Thr
            1220                1225                1230
Asp Asp Thr Val Met Met Thr Tyr Gln Leu Pro Ser Arg Asp Leu Glu
1235                1240                1245
Thr Val Leu Lys Glu Asp Lys Leu Lys Leu Lys Gln Met Gln Lys Leu
            1250                1255                1260
Gln Pro Lys Phe Thr Glu Asp Gln Lys Arg Glu Leu Ile Glu Val His
1265                1270                1275                1280
Pro Trp Ile Gln Gln Gly Gly Leu Pro Lys Thr Val Ala Asn Ser Glu
            1285                1290                1295
Cys Ile Phe Cys Glu Asp Asn Ile Gln Ser Asn Phe Tyr Thr Ser Tyr
            1300                1305                1310
Asp Glu Glu Ile His Glu Met Asp Leu Asn Glu Met Ile Glu Asp Ser
```

```
              1315                1320                1325
       Gly Glu Asn Asn Leu Val Pro Leu Ser Gln Val Asn Glu Glu Gln Thr
            1330                1335                1340
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:BMAL-F

<400> SEQUENCE: 29
gtgctmmgga tggcwgtkca gc            22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:BMAL-R

<400> SEQUENCE: 30
gcgyccratt gcvacraggc ag            22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:hB2F1

<400> SEQUENCE: 31
gaccaagtgg ctcctgcgat               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:hB2R1

<400> SEQUENCE: 32
gctagagggt ccactggatg               20

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:hBMAL2-F4

<400> SEQUENCE: 33
gtgctggtag tattggaaca gatattg       27

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:hBMAL2-R1

<400> SEQUENCE: 34
gctagagggt ccactggatg               20

<210> SEQ ID NO 35

<211> LENGTH: 32
<212> TYPE: DNA
<213> ORGANISM: Artificial Sequence
<220> FEATURE:
<223> OTHER INFORMATION: Description of Artificial Sequence:mBMAL2-F1

<400> SEQUENCE: 35
ggtcgaccac catggagttt ccaaggaaa cg                        32

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:mBMAL2-R1

<400> SEQUENCE: 36
gctagagtgc ccactggatg tcac                                24

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence:
      Sense primer 2

<400> SEQUENCE: 37
catgtctggc agaggcaag                                      19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence:Antisense
      primer 2

<400> SEQUENCE: 38
ttagccgccg aagccgtag                                      19

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      cB1F1600-primer

<400> SEQUENCE: 39
tccagacatt tcttcagctg g                                   21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:
      cB1REND-primer

<400> SEQUENCE: 40
ggatgttgaa gcaaggtgc                                      19

<210> SEQ ID NO 41
<211> LENGTH: 21
<212> TYPE: DNA
<213> ORGANISM: Artificial Sequence

```
<220> FEATURE:
<223> OTHER INFORMATION: Description of Artificial Sequence:
      cB2F1270-primer

<400> SEQUENCE: 41
acgagtactg ccatcaagat g                                            21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:
      cB2REND-primer

<400> SEQUENCE: 42
gagagcccat tggatgtcac                                              20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:
      cqCF862-primer

<400> SEQUENCE: 43
ttcttggatc acagggcac                                               19

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence:
      cqCR1364-primer

<400> SEQUENCE: 44
ggagtgctag tgtccactgt ca                                           22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:
      cP2RTF-primer

<400> SEQUENCE: 45
ggaagtcctt gcagtgcata c                                            21

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:
      cP2RTR-primer

<400> SEQUENCE: 46
acaggaagcg gatatgcag                                               19

<210> SEQ ID NO 47
<211> LENGTH: 20
<212> TYPE: DNA
<213> ORGANISM: Artificial Sequence
<220> FEATURE:
```

```
<223> OTHER INFORMATION: Description of Artificial Sequence:cGAF-primer

<400> SEQUENCE: 47
accactgtcc atgccatcac                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:cGAR-primer

<400> SEQUENCE: 48
tccacaacac ggttgctgta                                               20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence:mBMAL2-F2
      primer

<400> SEQUENCE: 49
tggttggatg cgaaagagg                                                19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence:mBMAL2-R4
      primer

<400> SEQUENCE: 50
aggtttctct cttggtgaac c                                             21

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence:rmBmal1-F1
      primer

<400> SEQUENCE: 51
tggtaccaac atgcaatgc                                                19

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence:rmBmal1-R1
      primer

<400> SEQUENCE: 52
agtgtccgag gaagatagct g                                             21

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence:rmPer2-F1
      primer
```

```
-continued

<400> SEQUENCE: 53
gctcactgcc agaactatct cc                                              22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence:rmPer2-R1
      primer

<400> SEQUENCE: 54
cctctagctg aagcaggtta ag                                              22

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence:rmClock-F1
      primer

<400> SEQUENCE: 55
caaggtcagc aacttgtgac c                                               21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:rmClock-R1
      primer

<400> SEQUENCE: 56
aggatgagct gtgtcgaagg                                                 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:mGAPDH F1
      primer

<400> SEQUENCE: 57
catcaccatc ttccaggagc                                                 20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:mGAPDH-R1
      primer

<400> SEQUENCE: 58
attgagagca atgccagcc                                                  19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence:cP2E1-S

<400> SEQUENCE: 59
```

```
gtgtcacacg tgaggctta                                             19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:cP2E1-AS

<400> SEQUENCE: 60
taagcctcac gtgtgacac                                             19

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence:Sense
      primer 3

<400> SEQUENCE: 61
tcgagctctt tggtacctgg ccagcaacc                                  29

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:Antisense
      primer 3

<400> SEQUENCE: 62
tcacgacacc tggccgttcg agg                                        23

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence:TRE and
      flanking sequence

<400> SEQUENCE: 63
cggctgactc atcaagctga ctcatcaagc tgactcatca a                    41
```